US007674811B2

(12) United States Patent
Verma et al.

(10) Patent No.: US 7,674,811 B2
(45) Date of Patent: Mar. 9, 2010

(54) 5-LIPOXYGENASE INHIBITORS

(75) Inventors: Ashwani Kumar Verma, Delhi (IN); Sanjay Malhotra, Delhi (IN); Abhijit Ray, Delhi (IN); Shirumalla Raj Kumar, Delhi (IN)

(73) Assignee: Ranbaxy Laboratories Limited, New Delhi (IN)

(*) Notice: Subject to any disclaimer, the term of this patent is extended or adjusted under 35 U.S.C. 154(b) by 256 days.

(21) Appl. No.: 11/685,892

(22) Filed: Mar. 14, 2007

(65) Prior Publication Data

US 2008/0021080 A1 Jan. 24, 2008

(30) Foreign Application Priority Data

Mar. 14, 2006 (IN) .......................... 699/DEL/2006

(51) Int. Cl.
*C07D 249/08* (2006.01)
*A61K 31/4196* (2006.01)
(52) U.S. Cl. .................. 514/383; 548/266.2; 548/262.2
(58) Field of Classification Search ................. 514/383; 548/262.2, 266.2
See application file for complete search history.

(56) References Cited

U.S. PATENT DOCUMENTS 5,883,106 A * 3/1999 Stevens et al. .............. 514/277

FOREIGN PATENT DOCUMENTS

| EP | 1 029 865 | 8/2000 |
|---|---|---|
| EP | 1 081 143 | 3/2001 |
| EP | 1 081 144 | 3/2001 |
| WO | WO 96/31485 | 10/1996 |
| WO | WO 96/40660 | 12/1996 |
| WO | WO 98/03492 | 1/1998 |
| WO | WO 98/03494 | 1/1998 |

OTHER PUBLICATIONS

Patini et al., Chem Rev, 1996, vol. 96, No. 8, pp. 3147-3176, see Table 2 on p. 3148, Table 9 on p. 3152, and Table 12 on p. 3153.*
Reiss et al., "Clinical efficacy of montelukast in adults and children", *Clinical and Experimental Allergy Reviews*, 1(30):264-273 (2001).
Creticos, "Clinical considerations of leukotriene modifiers in the treatment of rhinitis", *Clinical and Experimental Allergy Reviews*, 1(3):235-243 (2001).
Friedmann et al., "CysLT$_1$ antagonists in the treatment of atopic dermatitis and urticaria", *Clinical and Experimental Allergy Reviews*, 1(3):305-308 (2001).
Zühlke et al., "Montelukast attenuates the airway response to hypertonic saline in moderate-to-severe COPD", *European Respiratory Journal*, 22:926-930 (2003).
Imani, "Emerging therapeutic targets in asthma and allergy: modulation of IgE", *Expert Opinion on Therapeutic Targets*, 3(2):229-240 (1999).

Giembycz, "Cilomilast: a second generation phosphodiesterase 4 inhibitor for asthma and chronic obstructive pulmonary disease", *Expert Opinion on Investigational Drugs*, 10(7):1361-1379 (2001).
Werz, "5-Lipoxygenase: Cellular Biology and Molecular Pharmacology", *Current Drug Targets—Inflammation & Allergy*, 1(1):23-44 (2002).
Garcia-Marcos et al., "Benefit-Risk Assessment of Antileukotrienes in the Management of Asthma", *Drug Safety*, 26(7):483-518 (2003).
Busse, "Leukotrienes and Inflammation", *American Journal of Respiratory and Critical Care Medicine*, 157(6):S210-S213 (1998).
Leff, "Role of leukotrienes in bronchial hyperresponsiveness and cellular responses in airways", *Thorax*, 55(Suppl 2):S32-S37 (2000).
Sampson, "Leukotriene generation", *Clinical and Experimental Allergy Reviews*, 1(3):196-201 (2001).
Howarth, "Methods of assessing LTRA efficacy in humans", *Clinical and Experimental Allergy Reviews*, 1(3):220-228 (2001).
Aharony, "Pharmacology of Leukotriene Receptor Antagonists", *American Journal of Respiratory and Critical Care Medicine*, 157(6):S214-S219 (1998).
Drazen et al., "Treatment of Asthma with Drugs Modifying the Leukotriene Pathway", *The New England Journal of Medicine*, 340(3):197-206 (1999).
Birke et al., "In Vitro and in Vivo Pharmacological Characterization of BIIL 284, a Novel and Potent Leukotriene B$_4$ Receptor Antagonist", *The Journal of Pharmacology and Experimental Therapeutics*, 297(1):458-466 (2001).
Evans et al., "Effect of a leukotriene B$_4$ receptor antagonist, LY293111, on allergen induced responses in asthma", *Thorax*, 51:1178-1184 (1996).
Showell et al., "The Preclinical Pharmacological Profile of the Potent and Selective Leukotriene B$_4$ Antagonist CP-195543", *The Journal of Pharmacology and Experimental Therapeutics*, 285(3):946-954 (1998).
Poff and Balazy, "Drugs that Target Lipoxygenases and Leukotrienes as Emerging Therapies for Asthma and Cancer", *Current Drug Targets—Inflammation & Allergy*, 3(1):19-33 (2004).
O'Sullivan et al., "Urinary excretion of inflammatory mediators during allergen-induced early and late phase asthmatic reactions", *Clinical and Experimental Allergy*, 28(11):1332-1339 (1998).
Krein et al., "Roles for Insulin-Like Growth Factor I and Transforming Growth Factor-β in Fibrotic Lung Disease", *Chest*, 122(6):289S-293S (2002).
Cuzzocrea et al., "5-Lipoxygenase modulates colitis through the regulation of adhesion molecule expression and neutrophil migration", *Laboratory Investigation*, 85:808-822 (2005).
Singh et al., "Effect of 5-lipoxygenase inhibition on events associated with inflammatory bowel disease in rats", *Indian Journal of Experimental Biology*, 42(2):667-673 (2004).

(Continued)

*Primary Examiner*—Kamal A Saeed
*Assistant Examiner*—Michael Barker
(74) *Attorney, Agent, or Firm*—James J. DeYonker

(57) ABSTRACT

The present invention relates to 5-lipoxygenase inhibitors. Compounds disclosed herein can be useful in the treatment of bronchial asthma, chronic obstructive pulmonary disorder, arthritis, type I diabetes, multiple sclerosis, allograft rejection, psoriasis, inflammatory bowel disease, ulcerative colitis, acne, atherosclerosis, cancer, pruritis, urticaria, atopic dermatitis, allergic rhinitis, other inflammatory, and autoimmune diseases. Processes for the preparation of disclosed compounds, pharmaceutical compositions containing the disclosed compounds and their use as 5-lipoxygenase inhibitors are also provided.

11 Claims, No Drawings

OTHER PUBLICATIONS

Zouboulis et al., "Zileuton, an Oral 5-Lipoxygenase Inhibitor, Directly Reduces Sebum Production", *Dermatology*, 210(1):36-38 (2005).

Zouboulis et al., "A New Concept for Acne Therapy: A Pilot Study with Zileuton, an Oral 5-Lipoxygenase Inhibitor", *Archives of Dermatology*, 139:668-670 (2003).

Andoh et al., "Involvement of Leukotriene $B_4$ in Substance P-Induced Itch-Associated Response in Mice", *The Journal of Investigative Dermatology*, 117(6):1621-1626 (2001).

Dwyer et al., "Arachidonate 5-Lipoxygenase Promoter Genotype, Dietary Arachidonic Acid, and Atherosclerosis", *The New England Journal of Medicine*, 350(1):29-37 (2004).

De Caterina and Zampolli, "From Asthma to Atherosclerosis—5-Lipoxygenase, Leukotrienes, and Inflammation", *The New England Journal of Medicine*, 350(1):4-7 (2004).

Vila, "Cyclooxygenase and 5-Lipoxygenase Pathways in the Vessel Wall: Role in Atherosclerosis", *Medicinal Research Reviews*, 24(4):399-424 (2004).

Taylor et al., "Urinary Leukotriene $E_4$ After Antigen Challenge and in Acute Asthma and Allergic Rhinitis", *The Lancet*, 333(8638):584-588 (1989).

Emami et al., "(E)- and (Z)-1,2,4,-Triazolylchromanone oxime ethers as conformationally constrained antifungals", *Bioorganic and Medicinal Chemistry*, 12:3971-3976 (2004).

* cited by examiner

5-LIPOXYGENASE INHIBITORS

FIELD OF THE INVENTION

The present invention relates to 5-lipoxygenase inhibitors. Compounds disclosed herein can be useful in the treatment of bronchial asthma, chronic obstructive pulmonary disorder, arthritis, type I diabetes, multiple sclerosis, allograft rejection, psoriasis, inflammatory bowel disease, ulcerative colitis, acne, atherosclerosis, cancer, pruritis, urticaria, atopic dermatitis, allergic rhinitis, other inflammatory and autoimmune diseases.

Processes for preparing compounds described herein, pharmaceutical compositions thereof and their use as 5-lipoxygenase inhibitors are also provided.

BACKGROUND OF THE INVENTION

Lipoxygenases are non-heme, non-sulfur iron dioxygenases that act on lipid substrates containing one or more 1,4-pentadiene moieties to form hydroperoxides. 5-Lipoxygenase is a key enzyme that catalyses the first two steps in the oxygenation of arachidonic acid, which is converted to biologically active leukotrienes, namely leukotriene B4 (Clinical & Experimental Allergy Reviews, Volume 1, Number 3, November 2001, pp. 196-201(6)) and cysteinyl leukotrienes. Leukotrienes play important role in the pathophysiology of inflammatory/allergic diseases including bronchial asthma (Clinical & Experimental Allergy Reviews, Volume 1, Number 3, November 2001, pp. 264-273(10)), allergic rhinitis (Clinical & Experimental Allergy Reviews, Volume 1, Number 3, November 2001, pp. 235-243(9)), urticaria, atopic dermatitis (Clinical & Experimental Allergy Reviews, Volume 1, Number 3, November 2001, pp. 305-308(4)), chronic obstructive pulmonary disease (Eur. Respir. J., 2003, 22: 926-930). Incidence of allergic/inflammatory diseases are on the rise world over (Expert Opinion on Therapeutic Targets, Volume 3, Number 2, June 1999, pp. 229-240(12); Expert Opinion on Investigational Drugs, Volume 10, Number 7, 1 July 2001, pp. 1361-1379(19)).

A variety of stimuli, namely antigen-antibody reaction, cold or hypeosmotic shock etc, that elevates intracellular calcium level, can cause arachidonic acid release from cell membranes under the influence of cytosolic phospholipase A2. Arachidonic acid is transferred to nuclear membrane by 5-lipoxygenase binding protein (FLAP) and acted upon by 5-lipoxygenase enzyme to generate 5-hydroperoxyeicosatetraenoic acid (HPETE). HPETE is converted to LTA4 by 5-lipoxygenase. Depending upon cell type, LTA4 is converted to either cysteinyl leukotrienes and/or leukotriene B4 (Clinical & Experimental Allergy Reviews, Volume 1, Number 3, November 2001, pp. 196-201(6); Current Drug Targets—Inflammation & Allergy, Volume 1, Number 1, March 2002, pp. 23-44(22); Drug Safety, Volume 26, Number 7, 2003, pp. 483-518(36)).

Leukotrienes are generated by a variety of inflammatory cell types. Neutrophils and monocytes generate LTB4 whereas mast cells, basophils, eosinophils and bronchial epithelial cells produce cysteinyl leukotrienes. LTB4 acts as a chemo attractant for neutrophils through specific cell surface receptors. Cysteinyl leukotrienes, which include LTC4, LTD4 and LTE4, act on CysLT1 and CysLT2 receptors and increase bronchial smooth muscle contractility, promote mucosal secretion, increase vascular permeability and encourage eosinophils recruitment. (Am. J. Respir. Crit. Care Med., Volume 157, Number 6, June 1998, S210-S213; Thorax 2000, 55S32-S37; Clinical & Experimental Allergy Reviews, Volume 1, Number 3, November 2001, pp. 196-201(6); Clinical & Experimental Allergy Reviews, Volume 1, Number 3, November 2001, pp. 220-228(9); Drug Safety, Volume 26, Number 7, 2003, pp. 483-518(36)).

There is evidence suggesting that cysteinyl leukotrienes can increase airway smooth muscle contractility in preclinical studies (Am. J. Respir. Crit. Care Med., Volume 157, Number 6, June 1998, S214-S219) and clinical studies (Clinical & Experimental Allergy Reviews, Volume 1, Number 3, November 2001, pp. 220-228(9)). Inhalation of leukotrienes also increases influx of inflammatory cells in the airway of animals (Clinical & Experimental Allergy Reviews, Volume 1, Number 3, November 2001, pp. 220-228(9)) and humans (Am. J. Respir. Crit. Care Med., Volume 157, Number 6, June 1998, S210-S213). In patients with asthma, urinary excretion of LTE4 correlates with exercise or cold air induced bronchoconstriction (Lancet, 1, 584, 1989) allergen induced early and late phase response (Clinical & Experimental Allergy, Volume 28, Number 11, 1 Nov. 1998, pp. 1332-1339(8); Am. J. Respir. Crit. Care Med., Volume 157, Number 6, June 1998, S210-S213), as well as with reduction of $FEV_1$ in patients with nocturnal asthma (Am. J. Respir. Crit. Care Med., Volume 157, Number 6, June 1998, S233-S237). Efficacy of leukotriene biosynthesis inhibitors and leukotriene receptor antagonists have been tested in numerous trails involving asthma patients (Clinical & Experimental Allergy Reviews, Volume 1, Number 3, November 2001, pp. 254-260(7); Drug Safety, Volume 26, Number 7, 2003, pp. 483-518(36); The New England Journal of Medicine, Volume 340:197-206, 1999; Am. J. Respir. Crit. Care Med., Volume 157, Number 6, June 1998, S233-S237).

Emerging evidence shows that leukotrienes also contribute towards pathophysiology of COPD. Two major cell types, neutrophils and macrophages, generate LTB4 and are modulated by the same; these cell types are believed to participate in the pathogenesis of COPD (Am. J. Respir. Crit. Care Med., Volume 157, Number 6, June 1998, S210-S213). Patients with COPD exhibit elevated sputum neutrophilia and LTB4 levels (Chest. 2002; 121:197S-200S0. Elevated levels of LTB4 were shown to be present in the exhaled breath condensate of COPD patients (Thorax 2003; 58: 585-588) as well as in patients experiencing exacerbation of COPD (Thorax 2003; 58: 294-298). Inhibitors of leukotriene biosynthesis as well as LTB4 receptor antagonists have shown to reduce airway reactivity, airway inflammation and airway neutrophilia in animals (J. Clin. Exp. Aller. 91, 917, 1992; J. Pharmacol. Exp. Ther., 2001, 297: 458-466) as well as in human subjects (Thorax, 1996, 51: 1178-1184; Chest. 2002; 122: 289S-293S). Cysteinyl leukotriene antagonists, such as Montelukast, has shown protective effect in hypertonic saline induced bronchoconstriction in COPD patients (Eur. Respir. J., 2003, 22: 926-930).

Similarly, evidence is emerging based on animal and human data that leukotriene pathway modulators can play role in arthritis (J. Pharmacol. Exp. Ther., 1998, 285: 946-954), allergic rhinitis and urticaria (Clinical & Experimental Allergy Reviews, Volume 1, Number 3, November 2001, pp. 235-243(9)), cancer (Current Drug Targets—Inflammation & Allergy, Volume 3, Number 1, March 2004, pp. 19-33(15)), inflammatory bowel disease (Laboratory Investigation, 2005, 85, 808-822; Indian Journal of Experimental Biology Vol. 42, July 2004, pp. 667-673), acne (Dermatology 210(1), 36-38, 2005; Arch. Dermatol. 2003;139: 668-670), pruritis (J. Invest. Dermatol. 117, 1621, 2001), as well as atherosclerosis (N. Engl. J. Med. 2004, 350, 29-37; N. Engl. J. Med. 2004, 350, 4-7, Med. Res. Rev. 24, 399, 2004).

WO 96/14307, WO 96/40660, WO 98/03492 and WO 98/03494 disclose substituted benzylamine derivatives, which have been said to be useful in the diagnosis and treatment of feeding disorders such as obesity, bulimia and cardiovascular diseases such as essential hypertension and congestive heart failure due to the binding of these compounds to human Neuropeptide Y1 receptors.

WO 96/31485 discloses 1,3-dihydro-1-(phenylalkyl)-2H-imidazol-2-one derivatives, which have been said to have PDE IV and cytokine activity.

U.S. Pat. No. 5,883,106 discloses compounds, which have been described to have the ability to inhibit 5-lipoxygenase enzyme.

Several leukotriene receptor antagonists, Montelukast, Zafirlukast, and Pranlukast, and a 5-lipoxygenase inhibitor, Zileuton, has been launched in the market. Both categories of molecules have shown efficacy in clinical trials of bronchial asthma. Inhibitors of 5-lipoxygenase exhibit greater potential to exhibit efficacy in COPD as well because of their inhibitory effect on LTB4 mediated processes. However, commercially available 5-lipoxygenase inhibitor is associated with poor pharmacokinetic property and adverse events, such as elevation of hepatic transaminases. Thus, there remains a need for novel inhibitors of 5-lipoxygenase having improved pharmacokinetic profiles and reduced adverse effects.

SUMMARY OF THE INVENTION

Provided herein are 5-lipoxygenase inhibitors, which can be useful in the treatment of bronchial asthma, chronic obstructive pulmonary disorder, arthritis, type I diabetes, multiple sclerosis, allograft rejection, psoriasis, inflammatory bowel disease, ulcerative colitis, acne, atherosclerosis, cancer, pruritus, urticaria, atopic dermatitis, allergic rhinitis, other inflammatory and autoimmune diseases. Pharmaceutical compositions comprising compounds described herein can also be used in treating such conditions.

Pharmaceutically acceptable salts, pharmaceutically acceptable solvates, stereoisomers, tautomers, racemates, regioisomers, prodrugs, metabolites, polymorphs or N-oxides of the compounds described herein having the same type of activity are also provided.

In accordance with one aspect, there are provided compounds having the structure of Formula I,

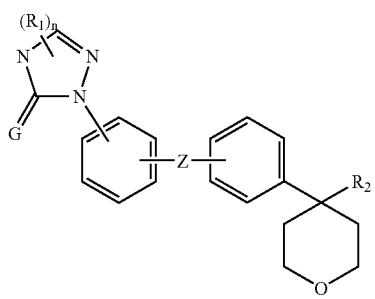

Formula I or pharmaceutically acceptable salts, pharmaceutically acceptable solvates, stereoisomers, tautomers, racemates, regioisomers, prodrugs, metabolites, polymorphs or N-oxides thereof, wherein G can be O or S, Z can be —(CH$_2$)$_n$—X— or —X—(CH$_2$)$_n$—, X can be —NR$_1$, —O—, —S—, n can be 0, 1 or 2, R$_1$ can be hydrogen, alkyl, alkenyl, alkynyl, cycloalkyl, (cycloalkyl)alkyl, aryl, aralkyl, heteroaryl, heterocyclyl, (heteroaryl)alkyl, or (heterocyclyl)alkyl, R$_2$ can be —CN, —COR$_3$, 5-membered heteroaryl or heterocyclyl, and R$_3$ can be hydrogen, alkyl, alkenyl, alkynyl, cycloalkyl, (cycloalkyl)alkyl, aryl, aralkyl, heteroaryl, heterocyclyl, (heteroaryl)alkyl, (heterocyclyl)alkyl, —OR$_1$, —SR$_1$ and —N(R$_1$)$_2$.

The following definitions apply to terms as used herein.

The term "alkyl," unless otherwise specified, refers to a monoradical branched or unbranched saturated hydrocarbon chain having from 1 to 20 carbon atoms. This term can be exemplified by groups such as methyl, ethyl, n-propyl, iso-propyl, n-butyl, iso-butyl, sec-butyl, t-butyl, n-pentyl, isopentyl, neopentyl, n-hexyl, n-decyl, tetradecyl, and the like. Alkyl groups may be substituted further with one or more substituents selected from alkenyl, alkynyl, alkoxy, cycloalkyl, cycloalkoxy, acyl, acylamino, acyloxy, alkoxycarbonylamino, azido, cyano, halogen, hydroxy, oxo, thiocarbonyl, carboxy, aryl, heterocyclyl, heteroaryl, arylthio, thiol, alkylthio, aryloxy, nitro, aminosulfonyl, aminocarbonylamino, —C(=O)heteroaryl, —C(=O)heterocyclyl, —NR$_f$R$_q$, —CH=NOH, —(CH$_2$)$_w$C(=O)R$_g$ {wherein w is an integer from 0-4 and R$_g$ is hydrogen, OR$_f$, —NR$_f$R$_q$, —NHOR$_z$ (wherein R$_z$ is alkyl, cycloalkyl, aryl, aralkyl, heteroaryl, heterocyclyl, heteroarylalkyl or heterocyclylalkyl) or —NHOH}, —C(=O)NR$_f$R$_q$, —NHC(=O)NR$_f$R$_q$, —O—C(=O)NR$_f$R$_q$, —O—C(=O)R$_f$, —O—C(=O)OR$_f$ {wherein R$_f$ and R$_q$ are hydrogen, alkyl, alkenyl, cycloalkyl, aryl, aralkyl, heterocyclyl, heteroaryl, (heterocyclyl)alkyl, (heteroaryl)alkyl)}, guanidine or —S(O)$_n$R$_d$ (wherein n is 0, 1 or 2, R$_d$ is alkyl, alkenyl, alkynyl, cycloalkyl, aralkyl, aryl, heterocyclyl, heteroaryl, heteroarylalkyl or heterocyclylalkyl). Unless otherwise constrained by the definition, alkyl substituents may be further substituted by 1-3 substituents selected from alkyl, carboxy, nitro, —NR$_f$R$_q$, —CH=NOH, —(CH$_2$)$_w$C(=O)R$_g$, —C(=O)NR$_f$R$_q$, —NHC(=O)NR$_f$R$_q$, —O—C(=O)NR$_f$R$_q$, —O—C(=O)R$_f$, —O—C(=O)OR$_f$(wherein w, R$_g$, R$_f$ and R$_q$ are the same as defined earlier), hydroxy, alkoxy, halogen, CF$_3$, cyano, guanidine or —S(O)$_n$R$_d$, (wherein n and R$_d$ are the same as defined earlier); or an alkyl group also may be interrupted by 1-5 atoms of groups independently selected from oxygen, sulfur or —NR$_a$— {wherein R$_a$ is selected from hydrogen, alkyl, cycloalkyl, alkenyl, alkynyl, aryl, acyl, aralkyl, —C(=O)OR$_f$(wherein R$_f$ is the same as defined earlier) or —C(=O)NR$_f$R$_q$ (wherein R$_f$ and R$_q$ are as defined earlier)}. Unless otherwise constrained by the definition, all substituents may be substituted further by 1-3 substituents selected from alkyl, carboxy, —NR$_f$R$_q$, —CH=NOH, —(CH$_2$)$_w$C(=O) R$_g$, —C(=O) NR$_f$R$_q$, —NHC(=O)NR$_f$R$_q$, —O—C(=O)NR$_f$R$_q$, —O—C(=O)R$_f$, —O—C(=O)OR$_f$, (wherein w, R$_g$, R$_f$ and R$_q$ are the same as defined earlier), hydroxy, alkoxy, halogen, CF$_3$, cyano, guanidine or S(O)$_n$R$_d$, (wherein n and R$_4$ are the same as defined earlier); or an alkyl group as defined above that has both substituents as defined above and is also interrupted by 1-5 atoms or groups as defined above.

The term "alkenyl," unless otherwise specified, refers to a monoradical of a branched or unbranched unsaturated hydrocarbon group having from 2 to 20 carbon atoms with cis, trans, or geminal geometry. In the event that alkenyl is attached to a heteroatom, the double bond cannot be alpha to the heteroatom. Alkenyl groups may be substituted further with one or more substituents selected from alkyl, alkynyl, alkoxy, cycloalkyl, cycloalkoxy, acyl, acylamino, acyloxy, —NR$_f$R$_q$, —CH=NOH, —(CH$_2$)$_w$C(=O) R$_g$, —C(=O) NR$_f$R$_q$, —NHC(=O)NR$_f$R$_q$, —O—C(=O)NR$_f$R$_q$, —O—C(=O)R$_f$, —O—C(=O)OR$_f$, (wherein w, R$_g$, R$_f$ and R$_q$ are the same as defined earlier), alkoxycarbonylamino, azido, cyano, halogen, hydroxy, oxo, thiocarbonyl, carboxy, arylthio, thiol, alkylthio, aryl, aralkyl, aryloxy, heterocyclyl, heteroaryl, (heterocyclyl)alkyl, (heteroaryl)alkyl, aminosulfonyl, aminocarbonylamino, alkoxyamino, nitro, guanidine or $(SO)_n R_d$ (wherein n and $R_d$ are the same as defined earlier). Unless otherwise constrained by the definition, alkenyl substituents optionally may be substituted further by 1-3 substituents selected from alkyl, carboy, hydroxy, alkoxy, halogen, —$CF_3$, cyano, —$NR_f R_q$, —CH=NOH, —$(CH_2)_w C(=O)R_g$, —$C(=O)NR_f R_q$, —$NHC(=O)NR_f R_q$, —O—C(=O)$NR_f R_q$, —O—C(=O)$R_f$, —O—C(=O)$OR_f$ (wherein w, $R_g$, $R_f$ and $R_q$ are the same as defined earlier) guanidine or $(SO)_n R_d$ (wherein n and $R_d$ are the same as define earlier).

The term "alkynyl," unless otherwise specified, refers to a monoradical of an unsaturated hydrocarbon, having from 2 to 20 carbon atoms. In the event that alkynyl is attached to a heteroatom, the triple bond cannot be alpha to the heteroatom. Alkynyl groups may be substituted further with one or more substituents selected from alkyl, alkenyl, alkoxy, cycloalkyl, cycloalkoxy, acyl, acylamino, acyloxy, alkoxycarbonyl amino, azido, cyano, halogen, hydroxy, oxo, thiocarbonyl, carboxy, arylthio, thiol, alkylthio, aryl, aralkyl, aryloxy, aminosulfonyl, aminocarbonylamino, nitro, heterocyclyl, heteroaryl, (heterocyclyl)alkyl, (heteroaryl)alkyl, —$NR_f R_q$, —CH=NOH, —$(CH_2)_w C(=O)R_g$, —$C(=O)NR_f R_q$, —$NHC(=O)NR_f R_q$, —O—C(=O)$NR_f R_q$, —O—C(=O)$R_f$, —O—C(=O)$OR_f$ (wherein w, $R_g$, $R_f$ and $R_q$ are the same as defined earlier), guanidine or —$(SO)_n R_d$ (wherein n and $R_d$ are the same as defined earlier). Unless otherwise constrained by the definition, alkynyl substituents optionally may be substituted further by 1-3 substituents selected from alkyl, carboxy, hydroxy, alkoxy, halogen, $CF_3$, —$NR_f R_q$, —CH=NOH, —$(CH_2)_w C(=O)$ $R_g$, —$C(=O)NR_f R_q$, —$NHC(=O)NR_f R_q$, —O—C(=O)$NR_f R_q$, —O—C(=O)$R_f$, —O—C(=O)$OR_f$ (wherein w, $R_g$, $R_f$ and $R_q$ are the same as defined earlier), cyano, guanidine or —$(SO)_n R_d$ (where n and $R_d$ are the same as defined earlier).

The term "cycloalkyl," unless otherwise specified, refers to cyclic alkyl groups of from 3 to 20 carbon atoms having a single cyclic ring or multiple condensed rings, which may optionally contain one or more olefinic bonds, unless otherwise constrained by the definition. Such cycloalkyl groups can include, for example, single ring structures, including cyclopropyl, cyclobutyl, cyclopentyl, cyclohexyl, cycloheptyl, cyclooctyl, cyclopentenyl, and the like, or multiple ring structures, including adamantanyl, and bicyclo [2.2.1] heptane, or cyclic alkyl groups to which is fused an aryl group, for example, indane, tetrahydroquinoline and the like. Spiro and fused ring structures can also be included. Cycloalkyl groups may be substituted further with one or more substituents selected from alkyl, alkenyl, alkynyl, alkoxy, cycloalkyl, cycloalkoxy, acyl, acylamino, acyloxy, alkoxycarbonylamino, azido, cyano, halogen, hydroxy, oxo, thiocarbonyl, carboxy, arylthio, thiol, alkylthio, aryl, aralkyl, aryloxy, aminosulfonyl, aminocarbonylamino, —$NR_f R_q$, —CH=NOH, —$(CH_2)_w C(=O)R_g$, —$C(=O)NR_f R_q$, —$NHC(=O)NR_f R_q$, —O—C(=O)$NR_f R_q$, —O—C(=O)$R_f$, —O—C(=O)$OR_f$ (wherein w, $R_g$, $R_f$ and $R_q$ are the same as defined earlier), nitro, heterocyclyl, heteroaryl, (heterocyclyl)alkyl, (heteroaryl)alkyl, guanidine or $(SO)_n R_d$ (wherein n and $R_4$ are the same as defined earlier). Unless otherwise constrained by the definition, cycloalkyl substituents optionally may be substituted further by 1-3 substituents selected from alkyl, carboxy, hydroxy, alkoxy, halogen, $CF_3$, —$NR_f R_q$, —CH=NOH, —$(CH_2)_w C(=O)R_g$, —$C(=O)NR_f R_q$, —$NHC(=O)NR_f R_q$, —O—C(=O)$NR_f R_q$, —O—C(=O)$R_f$, —O—C(=O)$OR_f$ (wherein w, $R_g$, $R_f$ and $R_q$ are the same as defined earlier), cyano, guanidine or $(SO)_n R_d$ (wherein n and $R_d$ are the same as defined earlier).

The term "(cycloalkyl)alkyl" refers to alkyl-cycloalkyl group linked through alkyl portion, wherein the alkyl and cycloalkyl are as defined earlier.

The term "alkoxy" denotes the group O-alkyl wherein alkyl is the same as defined above.

The term "aryl," unless otherwise specified, refers to carbocyclic aromatic groups, for example, phenyl, biphenyl or naphthyl ring and the like, optionally substituted with 1 to 3 substituents selected from halogen (e.g., F, Cl, Br, I), hydroxy, alkyl, alkenyl, alkynyl, cycloalkyl, cycloalkoxy, alkoxy, acyl, aryloxy, $CF_3$, cyano, nitro, —$NR_f R_q$, —CH=NOH, —$(CH_2)_w C(=O)R_g$, —$C(=O)NR_f R_q$, —$NHC(=O)NR_f R_q$, —O—C(=O)$NR_f R_q$, —O—C(=O)$R_f$, —O—C(=O)$OR_f$ (wherein w, $R_g$, $R_f$ and $R_q$ are the same as defined earlier), guanidine, —$(SO)_n R_d$ (wherein n and $R_d$ are the same as defined earlier), carboxy, heterocyclyl, heteroaryl, (heterocyclyl)alkyl, (heteroaryl)alkyl or aminocarbonylamino. The aryl group optionally may be fused with a cycloalkyl group, wherein the cycloalkyl group may optionally contain heteroatoms selected from O, N or S.

The term "aralkyl," unless otherwise specified, refers to alkyl-aryl linked through an alkyl portion (wherein alkyl is as defined above) and the alkyl portion contains 1-6 carbon atoms and aryl is as defined above. Examples of aralkyl groups include benzyl, phenyl ethyl, phenylpropyl and the like.

The term "aryloxy" denotes the group O-aryl, wherein aryl is as defined above.

The term "cycloalkoxy" denotes the group O-cycloalkyl, wherein cycloalkyl is as defined above.

The term "carboxy," as defined herein, refers to —C(=O)$OR_f$ wherein $R_f$ is the same as defined above.

The term "heteroaryl," unless otherwise specified, refers to an aromatic ring structure containing 5 or 6 ring atoms, or a bicyclic aromatic group having from 8 to 10 ring atoms, with one or more heteroatom(s) independently selected from N, O or S optionally substituted with 1 to 4 substituent(s) selected from halogen (e.g., F, Cl, Br, I), hydroxy, alkyl, alkenyl, alkynyl, cycloalkyl, cycloalkoxy, acyl, carboxy, aryl, alkoxy, oxo, aralkyl, cyano, nitro, heterocyclyl, heteroaryl, —$NR_f R_q$, —CH=NOH, —$(CH_2)_w C(=O)R_g$, —$C(=O)NR_f R_q$, —$NHC(=O)NR_f R_q$, —O—C(=O)$NR_f R_q$, —O—C(=O)$R_f$, —O—C(=O)$OR_f$ (wherein w, $R_g$, $R_f$ and $R_q$ are the same as defined earlier) or guanidine. Unless otherwise constrained by the definition, the substituents are attached to a ring atom, i.e., carbon or heteroatom in the ring.

The term "heterocyclyl," unless otherwise specified, refers to a non-aromatic monocyclic or bicyclic cycloalkyl group having 5 to 10 atoms wherein 1 to 4 carbon atoms in a ring are replaced by heteroatoms selected from O, S or N, and optionally are benzofused or fused heteroaryl having 5-6 ring members and/or optionally are substituted, wherein the substituents are selected from halogen (e.g., F, Cl, Br, I), hydroxy, alkyl, alkenyl, alkynyl, cycloalkyl, cycloalkoxy, acyl, aryl, alkoxy, aralkyl, cyano, nitro, oxo, carboxy, heterocyclyl, heteroaryl, —$NR_f R_q$, —CH=NOH, —$(CH_2)_w C(=O)R_g$, —$C(=O)NR_f R_q$, —$NHC(=O)NR_f R_q$, —O—C(=O)$NR_f R_q$, —O—C(=O)$R_f$, —O—C(=O)$OR_f$ (wherein w, $R_g$, $R_f$ and $R_q$ are the same as defined earlier) or guanidine. Heterocyclyl can optionally include rings having one or more double bonds. Unless otherwise constrained by the definition, the substituents are attached to the ring atom, i.e., carbon or heteroatom in the ring. Also, unless otherwise constrained by the definition, the heterocyclyl ring optionally may contain one or more olefinic bond(s).

Examples of heteroaryl and heterocyclyl groups include oxazolyl, imidazolyl, pyrrolyl, 1,2,3-triazolyl, 1,2,4-triazolyl, tetrazolyl, thiazolyl, oxadiazolyl, oxazolidinyl, thiadiazolyl, thiazolyl, thiazolinyl, thienothiazolyl, triazolone, imidazolone, thioimidazolone, thienooxazolyl, thienoimidazolyl, pyridinyl, pyridazinyl, pyrimidinyl, pyrazinyl, thienyl, isoxazolyl, triazinyl, furanyl, benzofuranyl, benzooxathiolone, oxathiazole, oxathiadiazole, thiotriazolone, indolyl, benzthiazolyl, oxathiazinyl, benzoxazolyl, benzimidazolyl, oxazolidinyl, tetrahydrofuranyl, dihydrofuranyl, morpholinyl, dihydropyridinyl, isothiazolidinyl, dihydroisoxazolyl, dihydrobenzofuryl, azabicyclohexyl, dihydroindolyl, isoindole 1,3-dione, piperidinyl or piperazinyl and the like.

The term "(heteroaryl)alkyl" refers to alkyl-heteroaryl group linked through alkyl portion, wherein the alkyl and heteroaryl are as defined earlier.

The term "(heterocyclyl)alkyl" refers to alkyl-heterocyclyl group linked through alkyl portion, wherein the alkyl and heterocyclyl are as defined earlier.

The term "acyl" refers to —C(=O)$R_z$ wherein $R_z$ is same as defined earlier.

The term "thiocarbonyl" refers to —C(=S)R''', wherein ''' is selected from hydrogen, alkyl, cycloalkyl, aryl, aralkyl, heteroaryl, heterocyclyl, heteroarylalkyl, heterocyclylalkyl, amine or substituted amine. Unless otherwise constrained by the definition, all substituents optionally may be substituted further by 1-3 substituents selected fro alkyl, aralkyl, cycloalkyl, aryl, heteroaryl, heterocyclyl, carboxy, hydroxy, alkoxy, halogen, $CF_3$, cyano, —C(=O)$NR_fR_q$, —O(C=O)$NR_fR_q$ (wherein $R_f$ and $R_q$ are the same as defined earlier), —(SO)$_nR_d$ (wherein n and $R_d$ are the same as defined earlier).

The term "amine," unless otherwise specified, refers to —$NH_2$. "Substituted amine," unless otherwise specified, refers to —$N(R_k)_2$, wherein each $R_k$ independently is selected from hydrogen {provided that both $R_k$ groups are not hydrogen (defined as "amino")}, alkyl, alkenyl, alkynyl, aralkyl, cycloalkyl, aryl, heteroaryl, heterocyclyl, heterocyclylalkyl, heteroarylalkyl, acyl, —C(=O)$NR_fR_q$, —NHC(=O)$NR_fR_q$, or —NHC(=O)$OR_f$ (wherein $R_f$ and $R_q$ are as defined earlier).

The term "halogen" refers to fluorine, chlorine, bromine or iodine.

Compounds described herein can be used for treating bronchial asthma, chronic obstructive pulmonary disorder, arthritis, type I diabetes, multiple sclerosis, allograft rejection, psoriasis, inflammatory bowel disease, ulcerative colitis, acne, atherosclerosis, cancer, pruritis, urticaria, atopic dermatitis, allergic rhinitis, other inflammatory and autoimmune diseases.

In accordance with yet another aspect, there are provided processes for the preparation of compounds described herein.

DETAILED DESCRIPTION OF THE INVENTION

Compounds described herein may be prepared by techniques known in the art. In addition, compounds described herein may be prepared by the following reaction sequences as depicted in Schemes I, II and III.

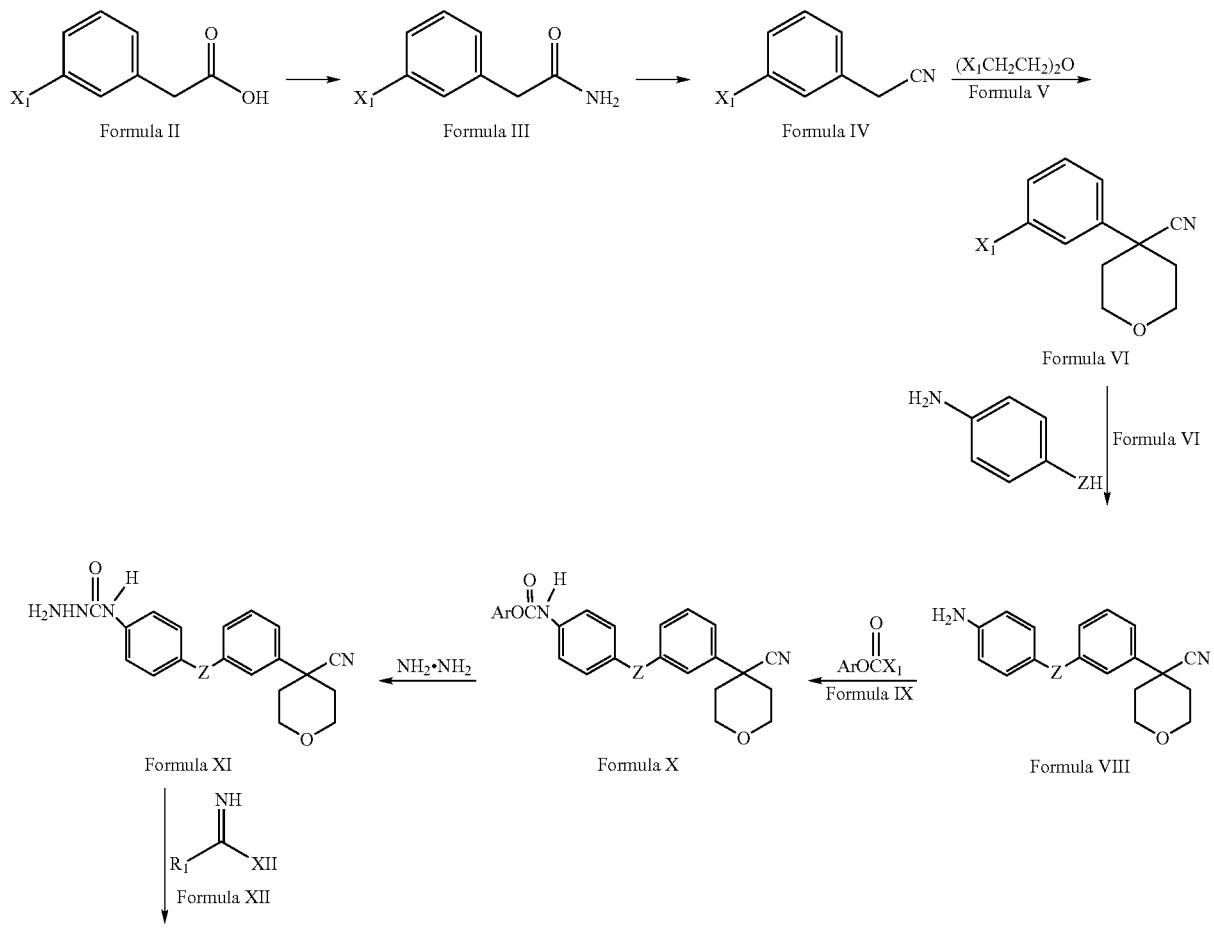

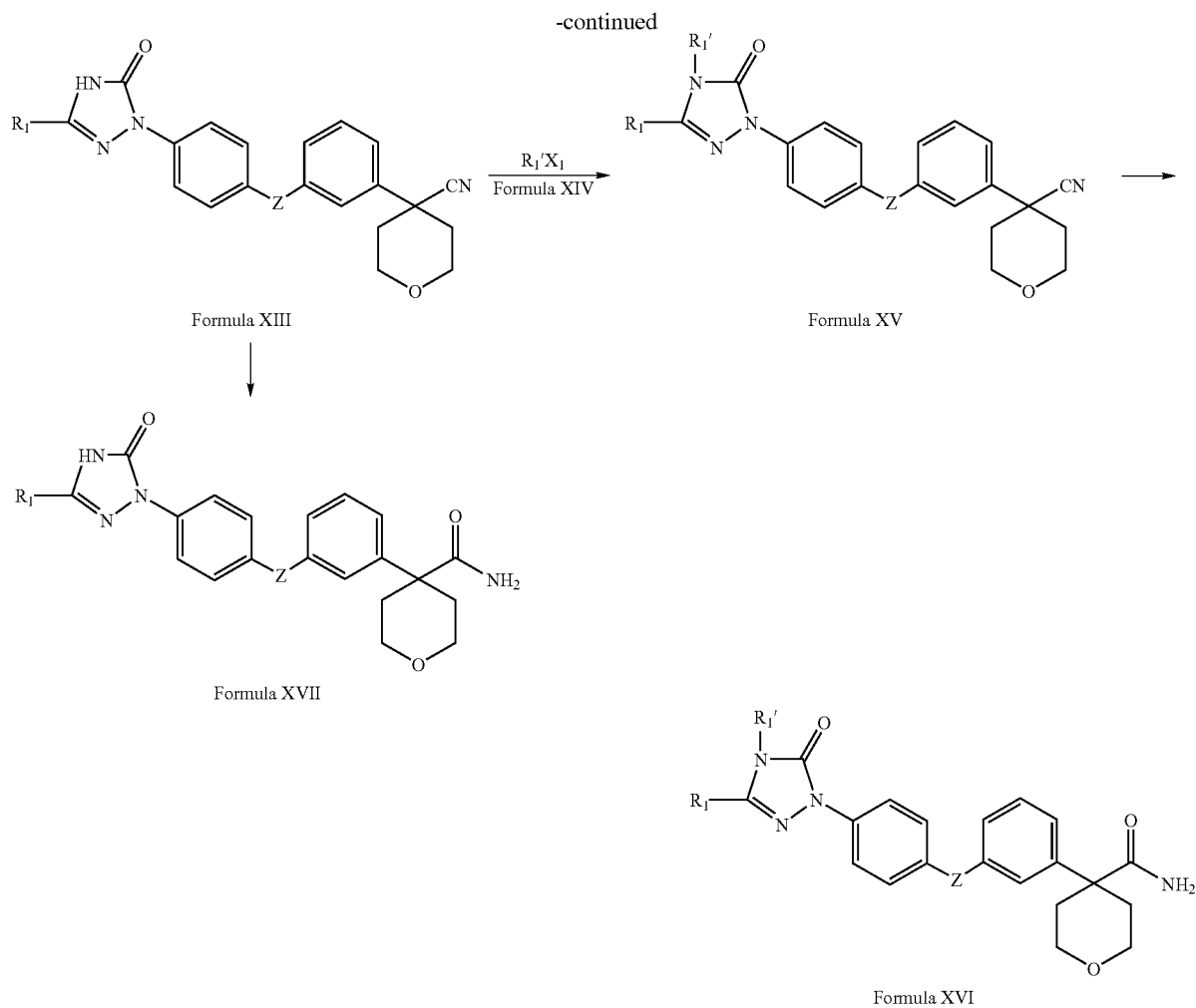

Compounds of Formula XVI and XVII can be prepared by following Scheme I. Accordingly, compounds of Formula II can be coupled with ammonium carbonate to form compounds of Formula III (wherein $X_1$ can be halogen). Compounds of Formula III can be dehydrated to form compounds of Formula IV. Compounds of Formula IV can be reacted with compounds of Formula V (wherein $X_1$ can be halogen) to form compounds of Formula VI. Compounds of Formula VI can be reacted with compounds of Formula VII to form compounds of Formula VIII (wherein Z can be the same as defined earlier). Compounds of Formula VIII can be reacted with compounds of Formula IX (wherein $X_1$ can be halogen) to form compounds of Formula X (wherein Ar can be aryl). Compounds of Formula X can be reacted with hydrazine to form compounds of Formula XI. Compounds of Formula XI can be reacted with compounds of Formula XII to form compounds of Formula XIII (wherein $R_1$ can be the same as defined earlier). Compounds of Formula XIII can be:

(i) reacted with compounds of Formula XIV (wherein $X_1$ can be halogen) to form compounds of Formula XV (wherein $R_1'$ can be alkyl, alkenyl, alkynyl, cycloalkyl, (cycloalkyl)alkyl, aryl, aralkyl, heteroaryl, heterocyclyl, (heteroaryl)alkyl, (heterocyclyl)alkyl) and compounds of Formula XV can be hydrolyzed to form compounds of Formula XVI; or (ii) hydrolyzed to form compounds of Formula XVII.

Compounds of Formula II can be coupled with ammonium carbonate to form compounds of Formula III in the presence of one or more coupling agents. Suitable coupling agents include, for example, 1-(3-dimethylaminopropyl)-3-ethylcarbodimide, N,N'-dicyclohexylcarbodiimide, 2-(1-H-benzotriazol-1-yl)-1,1,3,3-tetramethyluronium hexafluorophosphate (HBTU), O-(7-azabenzotriazol-1-yl)-N,N,N',N'-tetramethyluronium hexafluorophosphate (HATU), (benzotriazol-1-yloxy)tris-(dimethylamino)phosphonium hexafluorophosphate (BOP), propane phosphonic acid anhydride (T3P), O-(benzotriazol-1-yl)-N,N,N',N'-tetramethyluronium tetrafluoroborate (TBTU), S-(1-oxido-2-pyridinyl)-1,1,3,3-tetramethylthiouronium tetrafluoroborate (TOTT), N,N,N',N'-tetramethyl-O-(3,4-dihydro-4-oxo-1,2,3-benzotriazin-3-yl)uronium tetrafluoroborate (TDBTU), O-((ethoxycarbonyl) cyanomethyleneamino)-N,N,N',N'-tetramethyluronium tetrafluoroborate (TOTU), chlortripyrrolidino phosphoniumhexafluorophosphate (PyClop), benzotriazol-1-yl-oxy-tris-pyrrolidino-phosphonium hexafluorophosphate (PyBOP), chlorodipyrrolidinocarbenium hexafluorophosphate (PyClU), benzotriazol-1-yloxy) dipiperidinocarbenium hexafluorophosphate (HBPipU) or mixtures thereof.

Compounds of Formula II can also be coupled with ammonium carbonate in the presence of one or more of additives or activating agents. Suitable additives or activating agents include, for example, 1-hydroxybenzotriazole, acetone oxime, 2-hydroxypyridine, N-hydroxysuccinimide, pentafluorophenol or mixtures thereof.

Compounds of Formula II can be couple with ammonium carbonate in the presence of one or more of organic bases. Suitable organic bases include, for example, N-methylmorpholine, N-methylmorpholine oxide, 1-methylpiperidine, triethylamine, tribenzylamine, piperidine, N-ethyldiisopropylamine, N-ethylmorpholine, 2,6-lutidine or mixtures thereof.

Compounds of Formula II can also be coupled with ammonium carbonate in one or more of solvents. Suitable solvents include, for example, polar aprotic solvents, for example, dimethylformamide, dimethyl acetamide or dimethylsulphoxide, ethers, for example, tetrahydrofuran, dioxane or diethyl ether, nitriles, for example, acetonitrile or dimethoxyacetonitrile or mixtures thereof.

Compounds of Formula III can be dehydrated to form compounds of Formula IV in the presence of one or more of dehydrating agents. Suitable dehydrating agents include, for example, trifluoroacetic anhydride, trifluromethanesulfonic anhydride or mixtures thereof.

Compounds of Formula III can also be dehydrated in the presence of one or more of organic bases. Suitable organic bases include, for example, morpholine, N-methylmorpholine, 1-methylpiperidine, trimethylamine, triethylamine, tribenzylamine, N-ethyltriisopropylamine, piperidine or mixtures thereof.

Compounds of Formula III can be dehydrated in one or more of solvents. Suitable solvents include, for example, polar aprotic solvents, for example, dimethylformamide or dimethylsulphoxide, ethers, for example, tetrahydrofuran, dioxane or diethyl ether, nitriles, for example, acetonitrile or dimethoxyacetonitrile or mixtures thereof.

Compounds of Formula IV can be reacted with compounds of Formula V to form compounds of Formula VI in the presence of one or more of phase transfer catalysts. Suitable phase transfer catalysts include, for example, 15-crown-5 (15-c-5), cetyltrimethylammonium bromide (CTMAB), dibenzo-18-crown-6 (DB-18-c-6), dicyclohexano-18-crown-6 (DC-18-c-6), 18-crown-6 (18-c-6), N-dodecyl-N-methylephedrinium bromide (DMCOH), hexamethyl phosphoric triamide (HMPT), cetylpyridinium bromide (NCPB), N-benzylquininium chloride (QUIBEC), tetra-n-butylammonium bromide (TBAB), tetra-n-butylammonium chloride (TBAC), tetra-n-butylammonium hydroxide (TBAH), tetra-n-butylammonium hydrogen sulfate (TBAHS), tetra-n-butylammonium iodide (TBAI), tetraethylammonium chloride hydrate (TEAC), tri-n-butylamine (TBA), benzyltributylammonium bromide (TBBAB), hexadecyltributylphosphonium bromide (TBHDPB), benzyltriethylammonium bromide (TEBAB), benzyltriethylammonium chloride (TEBA), hexadecyltriethylammonium chloride (TEHDAC), tetramethylammonium chloride (TMAC), hexadecyltrimethylammonium chloride (TMHDAC), octyltrimethylammonium chloride (TMOAC) or mixtures thereof.

Compounds of Formula IV can be reacted with compounds of Formula V in the presence of one or more of iodinating reagents. Suitable iodinating reagents include, for example, alkali metal iodides, for example, sodium iodide, potassium iodide, lithium iodide or mixtures thereof.

Compounds of Formula IV can also be reacted with compounds of Formula V in the presence of one or more of bases. Suitable bases include, for example, alkali metal hydrides, for example, sodium hydride or potassium hydride, alkali metal amides (e.g., sodium amide, potassium amide or lithium amide), alkali metal alkoxides (e.g., sodium methoxide, sodium ethoxide, sodium tert-butoxide or potassium tert-butoxide), alkali metal hydroxides (e.g., sodium hydroxide or potassium hydroxide) or mixtures thereof.

Compounds of Formula IV can be reacted with compounds of Formula V in one or more of solvents. Suitable solvents include, for example, alcohols, for example, methanol, ethanol or propanol, polar aprotic solvents (e.g., dimethylformamide or dimethylsulphoxide), ethers (e.g., tetrahydrofuran, dioxane or diethyl ether) or mixtures thereof.

Compounds of Formula VI can be reacted with compounds of Formula VII to form compounds of Formula VIII in the presence of one or more of bases. Suitable bases include, for example, amines (e.g., N-ethyldiisopropylamine, triethylamine or dimethylaminopyridine), lithium methoxide, potassium methoxide, cesium methoxide or sodium ethoxide), alkali metal hydroxides (e.g., sodium hydroxide, lithium hydroxide, potassium hydroxide or cesium hydroxide), alkali metal halides (e.g., potassium fluoride or cesium fluoride), alkali metal carbonates (e.g., sodium carbonate, potassium carbonate or cesium carbonate) or mixtures thereof.

Compounds of Formula VI can be reacted with compounds of Formula VII in one or more of solvents. Suitable solvents include, for example, ethers (e.g., dibutyl ether, methyl tert-butyl ether, dioxane, cyclopentylmethylether or tetrahydrofuran), hydrocarbons (e.g., toluene or xylene), polar aprotic solvents (e.g., dimethylformamide, dimethyl sulphoxide or N-methylpyrrolidone) or mixtures thereof.

Compounds of Formula VIII can be reacted with compounds of Formula IX to form compounds of Formula X in the presence of one or more of organic bases. Suitable organic bases include, for example, pyridine, ethylamine, triethylamine, N-ethyldiisopropyl amine, piperidine or mixtures thereof.

Compounds of Formula VIII can be reacted with compounds of Formula IX in one or more of solvents. Suitable solvents include, for example, ethers (e.g., dibutyl ether, methyl tert-butyl ether, dioxane, cyclopentylmethylether or tetrahydrofuran), hydrocarbons (e.g., toluene or xylene), halogenated solvents (e.g., dichloromethane, dichloroethane, carbon tetrachloride or chloroform) or mixtures thereof.

Compounds of Formula X can be reacted with hydrazine to form compounds of Formula XI in one or more of solvents. Suitable solvents include, for example, ethers (e.g., dibutyl ether, methyl tert-butyl ether, dioxane, cyclopentylmethyl ether or tetrahydrofuran), alcohols (e.g., ethanol, propanol, isopropanol or cyclohexanol) or mixtures thereof.

Compounds of Formula XI can be reacted with compounds of Formula XII to form compounds of Formula XIII in the optional presence of one or more organic acids. Suitable organic acids include, for example, acetic acid, inorganic acids (e.g., hydrochloric acid) or mixtures thereof.

Compounds of Formula XI can be reacted with compounds of Formula XII in one or more of solvents. Suitable solvents include, for example, ethers (e.g., dibutyl ether, methyl tert-butyl ether, dioxane, cyclopentylmethyl ether or tetrahydrofuran), hydrocarbons (e.g., toluene, or xylene), polar aprotic solvents (e.g., dimethylformamide, dimethyl sulphoxide or N-methylpyrrolidone) or mixtures thereof.

Compounds of Formula XIII can be reacted with compounds of Formula XIV to form compounds of Formula XV in the presence of one or more of bases. Suitable bases include, for example, amines (e.g., N-ethyldiisopropylamine, triethylamine or dimethylaminopyridine), alkali metal alkoxides (e.g., sodium tert-butoxide, potassium tert-butoxide, sodium methoxide, lithium methoxide, potassium methoxide, cesium methoxide or sodium ethoxide), alkali metal hydroxides (e.g., sodium hydroxide, lithium hydroxide, potassium hydroxide or cesium hydroxide), alkali metal halides (e.g., potassium fluoride or cesium fluoride), alkali metal carbonates (e.g., sodium carbonate, potassium carbonate or cesium carbonate) or mixtures thereof.

Compounds of Formula XIII can be reacted with compounds of Formula XIV in one or more of solvents. Suitable solvents include, for example, ethers (e.g., dibutyl ether, methyl tert-butyl ether, dioxane, cyclopentylmethyl ether or tetrahydrofuran), hydrocarbons (e.g., toluene or xylene), polar aprotic solvents (e.g., dimethylformamide, dimethyl sulphoxide or N-methylpyrrolidone) or mixtures thereof.

Compounds of Formula XIII or compounds of Formula XV can be hydrolyzed to form compounds of Formula XVII or compounds of Formula XVI, respectively in the presence of one or more of bases. Suitable bases include, for example, alkali metal hydroxides (e.g., sodium hydroxide, lithium hydroxide, potassium hydroxide or cesium hydroxide), alkali metal halides (e.g., potassium fluoride or cesium fluoride), alkali metal carbonates (e.g., sodium carbonate, potassium carbonate or cesium carbonate) or mixtures thereof.

Compounds of Formula XIII or compounds of Formula XV can be also be hydrolyzed in one or more of solvents. Suitable solvents include, for example, alcohols (e.g., methanol, ethanol, propanol or isopropanol), polar aprotic solvents (e.g., dimethylformamide or dimethylsulphoxide), ethers (e.g., tetrahydrofuran, dioxane or diethyl ether) or mixtures thereof.

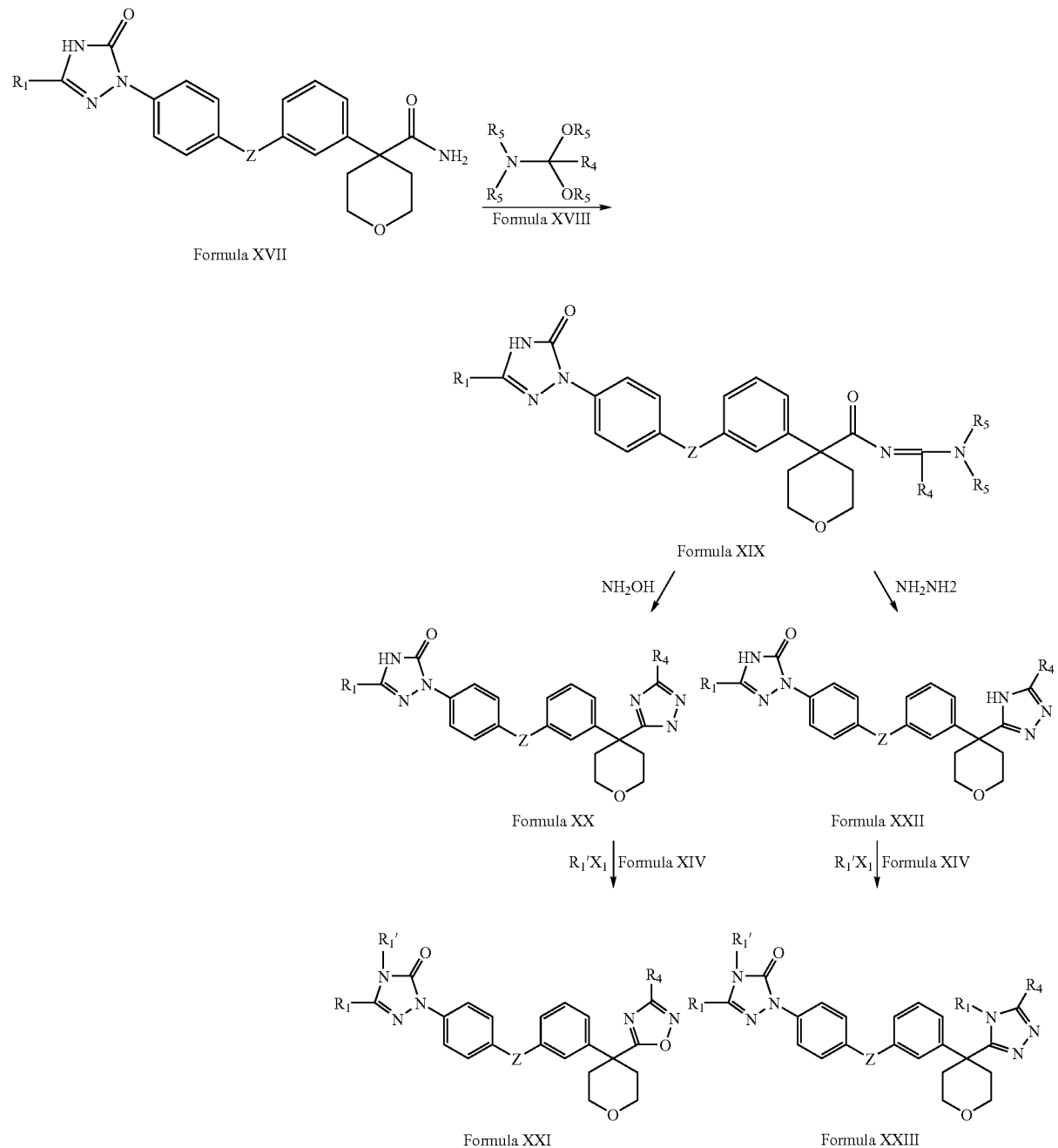

Scheme II

Compounds of Formula XXI and XXIII can be prepared by following Scheme II. Accordingly, compounds of Formula XVII can be reacted with compounds of Formula XVIII to form compounds of Formula XIX (wherein $R_4$ can be hydrogen or alkyl, $R_5$ can be alkyl and $R_1$ and Z can be same as defined earlier). Compounds of Formula XIX can be:

(i) reacted with hydroxylamine to form compounds of Formula XX; compounds of Formula XX can be reacted with compounds of Formula XIV (wherein $X_1$ can be halogen) to form compounds of Formula XXI (wherein $R_1'$ can be the same as defined earlier); or (ii) reacted with hydrazine to form compounds of Formula XXII; compounds of Formula XXII can be reacted with compounds of Formula XIV (wherein $X_1$ can be halogen) to form compounds of Formula XXIII (wherein $R_1'$ can be the same as defined earlier.

Compounds of Formula XVII can be reacted with compounds of Formula XVIII to form compounds of Formula XIX under reflux.

Compounds of Formula XIX can be reacted with hydroxylamine or hydrazine to form compounds of Formula XX or compounds of Formula XXII respectively in the presence of one or more of bases. Suitable bases include, for example, alkali metal hydroxides (e.g., sodium hydroxide or potassium hydroxide), alkali metal carbonates (e.g., sodium carbonate, potassium carbonate, lithium carbonate or cesium carbonate), alkali metal bicarbonates (e.g., sodium bicarbonate, potassium bicarbonate, lithium bicarbonate or cesium bicarbonate) or mixtures thereof.

Compounds of Formula XIX can be reacted with hydroxylamine or hydrazine in the presence of one or more of acids. Suitable acids include, for example, organic acids (e.g., acetic acid or formic acid) or inorganic acids (e.g., hydrochloric acid), or mixtures thereof.

Compounds of Formula XIX can be reacted with hydroxylamine or hydrazine in one or more of solvents. Suitable solvents include, for example, ethers (e.g., dibutyl ether, methyl tert-butyl ether, dioxane, cyclopentylmethyl ether or tetrahydrofuran), alcohols (e.g., methanol, ethanol, propanol or isopropanol) or mixtures thereof.

Compounds of Formula XX or compounds of Formula XXII can be reacted with compounds of Formula XIV to form compounds of Formula XXI or compounds of Formula XXIII respectively in the presence of one or more of bases. Suitable bases include, for example, amines (e.g., N-ethyldiisopropylamine, triethylamine or dimethylamino pyridine), alkali metal alkoxides (e.g., sodium tert-butoxide, potassium tert-butoxide, sodium methoxide, lithium methoxide, potassium methoxide, cesium methoxide or sodium ethoxide), alkali metal hydroxides (e.g., sodium hydroxide, lithium hydroxide, potassium hydroxide or cesium hydroxide), alkali metal halides (e.g., potassium fluoride or cesium fluoride), alkali metal carbonates (e.g., sodium carbonate, potassium carbonate or cesium carbonate), alkali metal hydrides (e.g., sodium hydride or potassium hydride) or mixtures thereof.

Compounds of Formula XX or compounds of Formula XXII can be reacted with compounds of Formula XIV in one or more of solvents. Suitable solvents include, for example, ethers (e.g., dibutyl ether, methyl tert-butyl ether, dioxane, cyclopentylmethyl ether or tetrahydrofuran), hydrocarbons (e.g., toluene or xylene), polar aprotic solvents (e.g., dimethylformamide, dimethyl sulphoxide or N-methylpyrrolidone), alcohols (e.g., ethanol or isopropanol) or mixtures thereof.

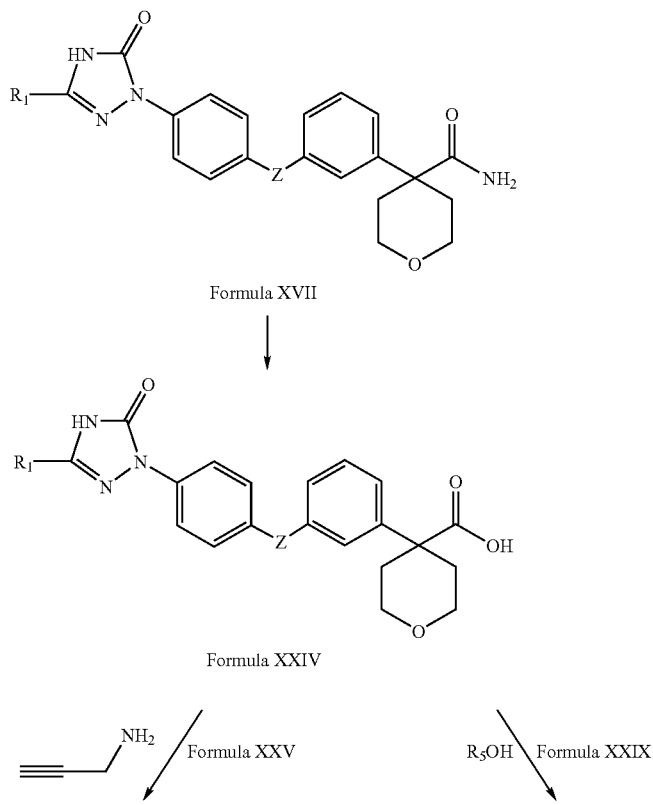

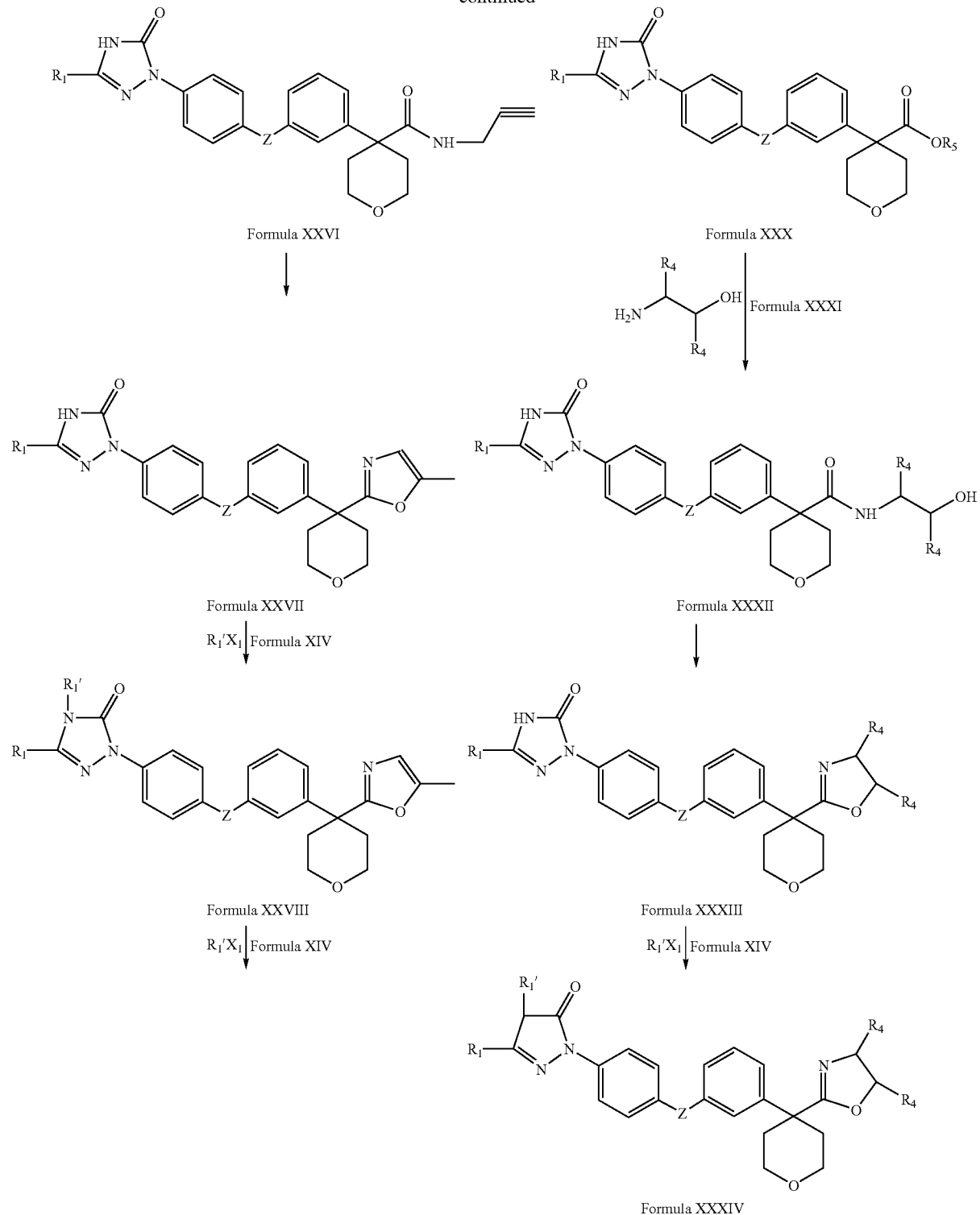

Compounds of Formula XXVIII and XXXIV can be prepared by following Scheme III. Accordingly, compounds of Formula XVII can be hydrolyzed to form compounds of Formula XXIV (wherein $R_1$ and Z can be same as defined earlier). Compounds of Formula XXIV can be:

(i) reacted with compounds of Formula XXV to form compounds of Formula XXVI; compounds of Formula XXVI can be cyclized to form compounds of Formula XXVII; and compounds of Formula XXVII can be reacted with compounds of Formula XIV (wherein $X_1$ can be halogen) to form compounds of Formula XXVIII (wherein $R_1'$ can be the same as defined earlier); or (ii) esterified with compounds of Formula XXIX to form compounds of Formula XXX (wherein $R_5$ can be alkyl); compounds of Formula XXX can be reacted with compounds of Formula XXXI to form compounds of Formula XXXII (wherein $R_4$ can be hydrogen or alkyl); compounds of Formula XXXII can be cyclized to form compounds of Formula XXXIII; and compounds of Formula XXXIII can be reacted with compounds of Formula XIV (wherein $X_1$ can be halogen) to form compounds of Formula XXXIV (wherein $R_1'$ can be the same as defined earlier).

Compounds of Formula XVII can be hydrolyzed to form compounds of Formula XXIV in the presence of one or more of bases. Suitable bases include, for example, alkali metal alkoxides (e.g., sodium tert-butoxide, potassium tert-butoxide, sodium methoxide, lithium methoxide, potassium methoxide, sodium ethoxide or cesium methoxide), alkali metal hydroxides (e.g., sodium hydroxide, lithium hydroxide, potassium hydroxide or cesium hydroxide), alkali metal halides (e.g., potassium fluoride or cesium fluoride), alkali metal carbonates (e.g., sodium carbonate, potassium carbonate or cesium carbonate) or mixtures thereof.

Compounds of Formula XVII can also be hydrolyzed in one or more of solvents. Suitable solvents include, for example, alcohols (e.g., methanol, ethanol, propanol or isopropanol), polar aprotic solvents (e.g., dimethylformamide or dimethylsulphoxide), ethers (e.g., tetrahydrofuran, dioxane or diethyl ether) or mixtures thereof.

Compounds of Formula XXIV can be reacted with compounds of Formula XXV to form compounds of Formula XXVI in the presence of one or more of coupling agents. Suitable coupling agents include, for example, 1-(3-dimethylaminopropyl)-3-ethyl-carbodimide, N,N'-dicyclohexylcarbodiimide, 2-(1-H-benzotriazol-1-yl)-1,1,3,3-tetramethyluronium hexafluorophosphate (HBTU), O-(7-azabenzotriazol-1-yl)-N,N,N',N'-tetramethyluronium hexafluorophosphate (HATU), (benzotriazol-1-yloxy) tris-(dimethylamino) phosphonium hexafluorophosphate (BOP), propane phosphonic acid anhydride (T3P), O-(benzotriazol-1-yl)-N,N,N',N'-tetramethyluronium tetrafluoroborate (TBTU), S-(1-oxido-2-pyridinyl)-1,1,3,3-tetramethylthiouronium tetrafluoroborate (TOTT), N,N,N',N'-tetramethyl-O-(3,4-dihydro-4-oxo-1,2,3-benzotriazin-3-yl)uronium tetrafluoroborate (TDBTU), O-(1,2-dihydro-2-oxo-pyridyl]-N,N,N',N'-tetramethyluronium tetrafluoroborate (TPTU), O-((ethoxycarbonyl) cyanomethylenamino)-N,N,N',N'-tetramethyluronium tetrafluoroborate (TOTU), chlortripyrrolidino phosphoniumhexafluorophosphate (PyClop), benzotriazol-1-yl-oxy-tris-pyrrolidino-phosphonium hexafluorophosphate (PyBOP), chlorodipyrrolidinocarbenium hexafluorophosphate (PyC1U), benzotriazol-1-yloxy) dipiperidinocarbenium hexafluorophosphate (HBPipU) or mixtures thereof.

Compounds of Formula XXIV can be reacted with compounds of Formula XXV in the presence of one or more of additives or activating agents. Suitable additives or activating agents include, for example, 1-hydroxybenzotriazole, acetone oxime, 2-hydroxypyridine, N-hydroxysuccinimide, pentafluorophenol or mixtures thereof.

Compounds of Formula XXIV can be reacted with compounds of Formula XXV in the presence of one or more of organic bases. Suitable organic bases include, for example, N-methylmorpholine, N-methylmorpholine oxide, N-ethyl-morpholine, 1-methylpiperidine, triethylamine, tribenzylamine, piperidine, N-ethyldiisopropylamine, 2,6-lutidine or mixtures thereof.

Compounds of Formula XXIV can be reacted with compounds of Formula XXV in one or more of solvents. Suitable solvents include, for example, polar aprotic solvents (e.g., dimethylformamide or dimethylsulphoxide), ethers (e.g., tetrahydrofuran, dioxane or diethyl ether), halogenated solvents (e.g., dichloromethane, dichloroethane, carbon tetrachloride or chloroform) or mixtures thereof.

Compounds of Formula XXVI can be cyclized to form compounds of Formula XXVII in the presence of one or more of cyclizing agents. Suitable cyclizing agents include, for example, mercuric acetate, tri-n-butyltin hydride or mixtures thereof.

Compounds of Formula XXVI can also be cyclized in one or more of acids. Suitable acids include, for example, acetic acid.

Compounds of Formula XXVI can be cyclized in one or more of solvents. Suitable solvents include, for example, polar aprotic solvents (e.g., dimethylformamide or dimethylsulphoxide) or ethers (e.g., tetrahydrofuran, dioxane or diethyl ether, hydrocarbons, for example, toluene or xylene) or mixtures thereof.

Compounds of Formula XXVII can be reacted with compounds of Formula XIV to form compounds of Formula XXVIII in the presence of one or more of bases. Suitable bases include, for example, amines (e.g., N-ethyldiisopropylamine, triethylamine or dimethylamino pyridine), alkali metal alkoxides (e.g., sodium tert-butoxide, potassium tert-butoxide, sodium ethoxide, sodium methoxide, lithium methoxide, potassium methoxide or cesium methoxide), alkali metal hydroxides (e.g., sodium hydroxide, lithium hydroxide, potassium hydroxide or cesium hydroxide), alkali metal halides (e.g., potassium fluoride or cesium fluoride), alkali metal carbonates (e.g., sodium carbonate, potassium carbonate or cesium carbonate), alkali metal hydrides (e.g., sodium hydride, calcium hydride or potassium hydride) or mixtures thereof.

Compounds of Formula XXVII can be reacted with compounds of Formula XIV in one or more of solvents. Suitable solvents include, for example, ethers (e.g., dibutyl ether, diethylether, methyl tert-butyl ether, dioxane, cyclopentylmethyl ether or tetrahydrofuran), hydrocarbons (e.g., toluene or xylene), polar aprotic solvents (e.g., dimethylformamide, dimethylsulphoxide, dimethylacetamide or N-methylpyrrolidone), alcohols (e.g., methanol, ethanol, propanol or isopropanol) or mixtures thereof.

Compounds of Formula XXIV can be esterified with compounds of Formula XXIX to form compounds of Formula XXX in the presence of one or more of halogenating agents. Suitable halogenating agents include, for example, phosphorous pentachloride, phosphorous pentabromide, phosphorous trichloride, phosphorous tribromide, thionyl chloride, oxalyl chloride or mixtures thereof.

Compounds of Formula XXX can be reacted with compounds of Formula XXXI to form compounds of Formula XXXII in one or more of alcohols. Suitable alcohols include, for example, methanol, ethanol, propanol or mixtures thereof.

Compounds of Formula XXXII can be cyclized to form compound of Formula XXXIII in the presence of cyclizing agents. Suitable cyclizing agents include, for example, triphenylphosphine.

Compounds of Formula XXXII can be cyclized in one or more of organic bases. Suitable organic bases include, for example, N-methylmorpholine, N-methylmorpholine oxide, N-ethylmorpholine, 1-methylpiperidine, triethylamine, tribenzylamine, piperidine, N-ethyldiisopropylamine, 2,6-lutidine or mixtures thereof.

Compounds of Formula XXXII can also be cyclized in one or more of solvents. Suitable solvents include, for example, halogenated solvents (e.g., dichloromethane, dichloroethane, carbon tetrachloride or chloroform), nitriles (e.g., acetonitrile or dimethoxyacetonitrile) or mixtures thereof.

Compounds of Formula XXXIII can be reacted with compounds of Formula XIV to form compounds of Formula XXXIV in the presence of one or more of bases. Suitable bases include, for example, amines (e.g., N-ethyldiisopropylamine, triethylamine or dimethylamino pyridine), alkali metal alkoxides (e.g., sodium tert-butoxide, potassium tert-butoxide, sodium ethoxide, sodium methoxide, lithium methoxide, potassium methoxide or cesium methoxide), alkali metal hydroxides (e.g., sodium hydroxide, lithium hydroxide, potassium hydroxide or cesium hydroxide), alkali metal halides (e.g., potassium fluoride or cesium fluoride), alkali metal carbonates (e.g., sodium carbonate, potassium carbonate or cesium carbonate), alkali metal hydrides (e.g., sodium hydride, calcium hydride or potassium hydride) or mixtures thereof.

Compounds of Formula XXXIII can be reacted with compounds of Formula XIV in one or more of solvents. Suitable solvents include, for example, ethers (e.g., dibutyl ether, diethylether, methyl tert-butyl ether, dioxane, cyclopentylmethyl ether or tetrahydrofuran), hydrocarbons (e.g., toluene or xylene), polar aprotic solvents (e.g., dimethylformamide, dimethylsulphoxide, dimethylacetamide or N-methylpyrrolidone), alcohols (e.g., methanol, ethanol, propanol or isopropanol) or mixtures thereof.

In the above schemes, where the specific reactants, for example, solvents, bases, acids, iodinating agents, coupling agents, additives or activating agents, dehydrating agents, phase transfer catalysts, cyclizing agents etc., are mentioned, it is to be understood that other reactants, e.g., solvents, bases, acids, iodinating agents, coupling agents, additives or activating agents, dehydrating agents, phase transfer catalysts, cyclizing agents etc., known to those skilled in the art may be used. Similarly, reaction conditions, for example, temperature and duration, may be adjusted accordingly.

Examples of compounds prepared by Schemes I, II and III include:

4-(3-{[4-(4-Ethyl-3-methyl-5-oxo-4,5-dihydro-1H-1,2,4-triazol-1-yl)phenyl]thio}phenyl)tetrahydro-2H-pyran-4-carboxamide (Compound No. 1), 4-(3-{[4-(4-Isobutyl-3-methyl-5-oxo-4,5-dihydro-1H-1,2,4-triazol-1-yl)phenyl]thio}phenyl)tetrahydro-2H-pyran-4-carboxamide (Compound No. 2), 4-(3-{[4-(4-Cyclopentyl-3-methyl-5-oxo-4,5-dihydro-1H-1,2,4-triazol-1-yl)phenyl]thio}phenyl)tetrahydro-2H-pyran-4-carboxamide (Compound No. 3), 4-(3-{[4-(3-Methyl-5-oxo-4-propyl-4,5-dihydro-1H-1,2,4-triazol-1-yl)phenyl]thio}phenyl)tetrahydro-2H-pyran-4-carboxamide (Compound No. 4), 4-(3-{[4-(4-Isopropyl-3-methyl-5-oxo-4,5-dihydro-1H-1,2,4-triazol-1-yl)phenyl]thio}phenyl)tetrahydro-2H-pyran-4-carboxamide (Compound No. 5), 4-(3-{[4-(4-Butyl-3-methyl-5-oxo-4,5-dihydro-1H-1,2,4-triazol-1-yl)phenyl]thio}phenyl)tetrahydro-2H-pyran-4-carboxamide (Compound No. 6), 4-(3-{[4-(3-Methyl-5-oxo-4,5-dihydro-1H-1,2,4-triazol-1-yl)phenyl]thio}phenyl)tetrahydro-2H-pyran-4-carboxamide (Compound No. 7), 4-(3-{[4-(4-Allyl-3-methyl-5-oxo-4,5-dihydro-1H-1,2,4-triazol-1-yl)phenyl]thio}phenyl)tetrahydro-2H-pyran-4-carboxamide (Compound No. 8), 4-[3-({4-[3-Methyl-4-(2-morpholin-4-ylethyl)-5-oxo-4,5-dihydro-1H-1,2,4-triazol-1-yl]phenyl}thio)phenyl]tetrahydro-2H-pyran-4-carboxamide (Compound No. 9), 4-[3-({4-[4-(2-Chloroethyl)-3-methyl-5-oxo-4,5-dihydro-1H-1,2,4-triazol-1-yl]phenyl}thio)phenyl]tetrahydro-2H-pyran-4-carboxamide (Compound No. 10), 4-[3-({4-[4-(Cyclohexylmethyl)-3-methyl-5-oxo-4,5-dihydro-1H-1,2,4-triazol-1-yl]phenyl}thio)phenyl]tetrahydro-2H-pyran-4-carboxamide (Compound No. 11), 4-[3-({4-[4-(2-Hydroxyethyl)-3-methyl-5-oxo-4,5-dihydro-1H-1,2,4-triazol-1-yl]phenyl}thio)phenyl]tetrahydro-2H-pyran-4-carboxamide (Compound No. 12), 4-(3-{[4-(4-Cyclohexyl-3-methyl-5-oxo-4,5-dihydro-1H-1,2,4-triazol-1-yl)phenyl]thio}phenyl)tetrahydro-2H-pyran-4-carboxamide (Compound No. 13), 4-(3-{[4-(4-Methyl-5-oxo-4,5-dihydro-1H-1,2,4-triazol-1-yl)phenyl]thio}phenyl)tetrahydro-2H-pyran-4-carboxamide (Compound No. 14), 4-(3-{[4-(4-Ethyl-5-oxo-4,5-dihydro-1H-1,2,4-triazol-1-yl)phenyl]thio}phenyl)tetrahydro-2H-pyran-4-carboxamide (Compound No. 15), 4-(3-{[4-(5-Oxo-4-propyl-4,5-dihydro-1H-1,2,4-triazol-1-yl)phenyl]thio}phenyl)tetrahydro-2H-pyran-4-carboxamide (Compound No. 16), 4-[3-({4-[4-(Cyclopropylmethyl)-5-oxo-4,5-dihydro-1H-1,2,4-triazol-1-yl]phenyl}thio)phenyl]tetrahydro-2H-pyran-4-carboxamide (Compound No. 17), 4-(3-{[4-(4-Isopropyl-5-oxo-4,5-dihydro-1H-1,2,4-triazol-1-yl)phenyl]thio}phenyl)tetrahydro-2H-pyran-4-carboxamide (Compound No. 18), 4-(3-{[4-(4-Butyl-5-oxo-4,5-dihydro-1H-1,2,4-triazol-1-yl)phenyl]thio}phenyl)tetrahydro-2H-pyran-4-carboxamide (Compound No. 19), 4-(3-{[4-(4-Cyclopentyl-5-oxo-4,5-dihydro-1H-1,2,4-triazol-1-yl)phenyl]thio}phenyl)tetrahydro-2H-pyran-4-carboxamide (Compound No. 20), 4-(3-{[4-(4-Isobutyl-5-oxo-4,5-dihydro-1H-1,2,4-triazol-1-yl)phenyl]thio}phenyl)tetrahydro-2H-pyran-4-carboxamide (Compound No. 21), 4-(3-{[4-(4-Cyclohexyl-5-oxo-4,5-dihydro-1H-1,2,4-triazol-1-yl)phenyl]thio}phenyl)tetrahydro-2H-pyran-4-carboxamide (Compound No. 22), 4-[3-({4- [4-(Cyclohexylmethyl)-5-oxo-4,5-dihydro-1H-1,2,4-triazol-1-yl]phenyl}thio)phenyl]tetrahydro-2H-pyran-4-carboxamide (Compound No. 23), 4-(3-{[4-(4-Cycloheptyl-5-oxo-4,5-dihydro-1H-1,2,4-triazol-1-yl)phenyl]thio}phenyl)tetrahydro-2H-pyran-4-carboxamide (Compound No. 24), 4-(3-{[4-(4-Allyl-5-oxo-4,5-dihydro-1H-1,2,4-triazol-1-yl)phenyl]thio}phenyl)tetrahydro-2H-pyran-4-carboxamide (Compound No. 25), 4-[3-({4-[4-(2-Hydroxyethyl)-5-oxo-4,5-dihydro-1H-1,2,4-triazol-1-yl]phenyl}thio)phenyl]tetrahydro-2H-pyran-4-carboxamide (Compound No. 26), 4-(3-{[4-(3,4-Dimethyl-5-oxo-4,5-dihydro-1H-1,2,4-triazol-1-yl)phenyl]thio}phenyl)tetrahydro-2H-pyran-4-carbonitrile (Compound No. 27), 4-(3-{[4-(4-Ethyl-3-methyl-5-oxo-4,5-dihydro-1H-1,2,4-triazol-1-yl)phenyl]thio}phenyl)tetrahydro-2H-pyran-4-carbonitrile (Compound No. 28), 4-(3-{[4-(4-Isopropyl-3-methyl-5-oxo-4,5-dihydro-1H-1,2,4-triazol-1-yl)phenyl]thio}phenyl)tetrahydro-2H-pyran-4-carbonitrile (Compound No. 29), 4-(3-{[4-(3-Methyl-5-oxo-4-propyl-4,5-dihydro-1H-1,2,4-triazol-1-yl)phenyl]thio}phenyl)tetrahydro-2H-pyran-4-carbonitrile (Compound No. 30), 4-(3-{[4-(4-Cyclohexyl-3-methyl-5-oxo-4,5-dihydro-1H-1,2,4-triazol-1-yl)phenyl]thio}phenyl)tetrahydro-2H-pyran-4-carbonitrile (Compound No. 31), 4-(3-{[4-(4-Isobutyl-3-methyl-5-oxo-4,5-dihydro-1H-1,2,4-triazol-1-yl)phenyl]thio}phenyl)tetrahydro-2H-pyran-4-carbonitrile (Compound No. 32), 4-(3-{[4-(4-Butyl-3-methyl-5-oxo-4,5-dihydro-1H-1,2,4-triazol-1-yl)phenyl]thio}phenyl)tetrahydro-2H-pyran-4-carbonitrile (Compound No. 33), 4-[3-({4-[4-(Cyclopropylmethyl)-3-methyl-5-oxo-4,5-dihydro-1H-1,2,4-triazol-1-yl]phenyl}thio)phenyl]tetrahydro-2H-pyran-4-carbonitrile (Compound No. 34), 4-[3-({4-[4-(Cyclohexylmethyl)-3-methyl-5-oxo-4,5-dihydro-1H-1,2,4-triazol-1-yl]phenyl}thio)phenyl]tetrahydro-2H-pyran-4-carbonitrile (Compound No. 35), 4-(3-{[4-(4-Cyclopentyl-3-methyl-5-oxo-4,5-dihydro-1H-1,2,4-triazol-1-yl)phenyl]thio}phenyl)tetrahydro-2H-pyran-4-carbonitrile (Compound No. 36), 4-[3-({4-[4-(2-Chloroethyl)-3-methyl-5-oxo-4,5-dihydro-1H-1,2,4-triazol-1-yl]phenyl}thio)phenyl]tetrahydro-2H-pyran-4-carbonitrile (Compound No. 37), 4-[3-({4-[4-(2-Hydroxyethyl)-3-methyl-5-oxo-4,5-dihydro-1H-1,2,4-triazol-1-yl]phenyl}thio)phenyl]tetrahydro-2H-pyran-4-carbonitrile (Compound No. 38), 4-(3-{[4-(4-Allyl-3-methyl-5-oxo-4,5-dihydro-1H-1,2,4-triazol-1-yl)phenyl]thio}phenyl)tetrahydro-2H-pyran-4-carbonitrile (Compound No. 39), 4-[3-({4-[3-Methyl-4-(2-morpholin-4-ylethyl)-5-oxo-4,5-dihydro-1H-1,2,4-triazol-1-yl]phenyl}thio)phenyl]tetrahydro-2H-pyran-4-carbonitrile (Compound No. 40), 4-[3-({4-[4-(Cyanomethyl)-3-methyl-5-oxo-4,5-dihydro-1H-1,2,4-triazol-1-yl]phenyl}thio)phenyl]tetrahydro-2H-pyran-4-carbonitrile (Compound No. 41), 4-(3-{[4-(4-Cycloheptyl-3-methyl-5-oxo-4,5-dihydro-1H-1,2,4-triazol-1-yl)phenyl]thio}phenyl)tetrahydro-2H-pyran-4-carbonitrile (Compound No. 42), 4-(3-{[4-(4-Methyl-5-oxo-4,5-dihydro-1H-1,2,4-triazol-1-yl)phenyl]thio}phenyl)tetrahydro-2H-pyran-4-carbonitrile (Compound No. 43), 4-(3-{[4-(4-Ethyl-5-oxo-4,5-dihydro-1H-1,2,4-triazol-1-yl)phenyl]thio}phenyl)tetrahydro-2H-pyran-4-carbonitrile (Compound No. 44), 4-(3-{[4-(5-Oxo-4-propyl-4,5-dihydro-1H-1,2,4-triazol-1-yl)phenyl]thio}phenyl)tetrahydro-2H-pyran-4-carbonitrile (Compound No. 45), 4-(3-{[4-(4-Isopropyl-5-oxo-4,5-dihydro-1H-1,2,4-triazol-1-yl)phenyl]thio}phenyl)tetrahydro-2H-pyran-4-carbonitrile (Compound No. 46), 4-(3-{[4-(4-Butyl-5-oxo-4,5-dihydro-1H-1,2,4-triazol-1-yl)phenyl]thio}phenyl)tetrahydro-2H-pyran-4-carbonitrile (Compound No. 47), 4-(3-{[4-(4-Isobutyl-5-oxo-4,5-dihydro-1H-1,2,4-triazol-1-yl)phenyl]thio}phenyl)tetrahydro-2H-pyran-4-carbonitrile (Compound No. 48), 4-(3-{[4-(4-Cyclopropyl-5-oxo-4,5-dihydro-1H-1,2,4-triazol-1-yl)phenyl]thio}phenyl)tetrahydro-2H-pyran-4-carbonitrile (Compound No. 49), 4-[3-({4-[4-(Cyclopropylmethyl)-5-oxo-4,5-dihydro-1H-1,2,4-triazol-1-yl]phenyl}thio)phenyl]tetrahydro-2H-pyran-4-carbonitrile (Compound No. 50), 4-(3-{[4-(4-Cyclopentyl-5-oxo-4,5-dihydro-1H-1,2,4-triazol-1-yl)phenyl]thio}phenyl)tetrahydro-2H-pyran-4-carbonitrile (Compound No. 51), 4-(3-{[4-(4-Cyclohexyl-5-oxo-4,5-dihydro-1H-1,2,4-triazol-1-yl)phenyl]thio}phenyl)tetrahydro-2H-pyran-4-carbonitrile (Compound No. 52), 4-[3-({4-[4-(Cyclohexylmethyl)-5-oxo-4,5-dihydro-1H-1,2,4-triazol-1-yl]phenyl}thio)phenyl]tetrahydro-2H-pyran-4-carbonitrile (Compound No. 53), 4-(3-{[4-(4-Cycloheptyl-5-oxo-4,5-dihydro-1H-1,2,4-triazol-1-yl)phenyl]thio}phenyl)tetrahydro-2H-pyran-4-carbonitrile (Compound No. 54), 4-(3-{[4-(4-Allyl-5-oxo-4,5-dihydro-1H-1,2,4-triazol-1-yl)phenyl]thio}phenyl)tetrahydro-2H-pyran-4-carbonitrile (Compound No. 55), 4-(3-{[4-(5-Oxo-4-prop-2-yn-1-yl-4,5-dihydro-1H-1,2,4-triazol-1-yl)phenyl]thio}phenyl)tetrahydro-2H-pyran-4-carbonitrile (Compound No. 56), 4-[3-({4-[4-(2-Hydroxyethyl)-5-oxo-4,5-dihydro-1H-1,2,4-triazol-1-yl]phenyl}thio)phenyl]tetrahydro-2H-pyran-4-carbonitrile (Compound No. 57), 4,5-Dimethyl-2-[4-({3-[4-(4-methyl-4H-1,2,4-triazol-3-yl)tetrahydro-2H-pyran-4-yl]phenyl}thio)phenyl]-2,4-dihydro-3H-1,2,4-triazol-3-one (Compound No. 58), 4-Ethyl-2-[4-({3-[4-(4-ethyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 59), 5-Methyl-4-propyl-2-[4-({3-[4-(4-propyl-4H-1,2,4-triazol-3-yl)tetrahydro-2H-pyran-4-yl]phenyl}thio)phenyl]-2,4-dihydro-3H-1,2,4-triazol-3-one (Compound No. 60), 4-Isopropyl-2-[4-({3-[4-(4-isopropyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 61), 4-Butyl-2-[4-({3-[4-(4-butyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 62), 4-Isobutyl-2-[4-({3-[4-(4-isobutyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 63), 4-Cyclopentyl-2-[4-({3-[4-(4-cyclopentyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 64), 4-Cyclohexyl-2-[4-({3-[4-(4-cyclohexyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 65), 4-Cycloheptyl-2-[4-({3-[4-(4-cycloheptyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 66), 4-Allyl-2-[4-({3-[4-(4-allyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 67), 5-Methyl-2-[4-({3-[4-(4H-1,2,4-triazol-3-yl)tetrahydro-2H-pyran-4-yl]phenyl}thio)phenyl]-2,4-dihydro-3H-1,2,4-triazol-3-one (Compound No. 68), 4,5-Dimethyl-2-[4-({3-[4-(3-methyl-1,2,4-oxadiazol-5-yl)tetrahydro-2H-pyran-4-yl]phenyl}thio)phenyl]-2,4-dihydro-3H-1,2,4-triazol-3-one (Compound No. 69), 5-Methyl-2-[4-({3-[4-(5-methyl-1,3-oxazol-2-yl)tetrahydro-2H-pyran-4-yl]phenyl}thio)phenyl]-2,4-dihydro-3H-1,2,4-triazol-3-one (Compound No. 70), 4,5-Dimethyl-2-[4-({3-[4-(5-methyl-1,3-oxazol-2-yl)tetrahydro-2H-pyran-4-yl]phenyl}thio)phenyl]-2,4-dihydro-3H-1,2,4-triazol-3-one (Compound No. 71), 2-[4-({3-[4-(4,5-Dimethyl-4,5-dihydro-1,3-oxazol-2-yl)tetrahydro-2H-pyran-4-yl]phenyl}thio)phenyl]-5-methyl-2,4-dihydro-3H-1,2,4-triazol-3-one (Compound No. 72), 2-[4-({3-[4-(4,5-Dimethyl-4,5-dihydro-1,3-oxazol-2-yl) tetrahydro-2H-pyran-4-yl]phenyl}thio)phenyl]-4,5-dimethyl-2,4-dihydro-3H-1,2,4-triazol-3-one (Compound No. 73), or a pharmaceutically acceptable salt, pharmaceutically acceptable solvate, stereoisomer, tautomer, racemate, regioisomer, prodrug, metabolite, polymorph or N-oxide thereof.

The term "pharmaceutically acceptable" means approved by regulatory agency of the federal or a state government or listed in the U.S. Pharmacopoeia or other generally recognized pharmacopoeia for use in animals, and more particularly in humans.

The term "pharmaceutically acceptable salts" refers to derivatives of compounds that can be modified by forming their corresponding acid or base salts. Examples of pharmaceutically acceptable salts include, but are not limited to, mineral or organic acids salts of basic residues (such as amines), or alkali or organic salts of acidic residues (such as carboxylic acids), and the like.

Salt forms differ from the compound in certain physical properties such as solubility, but the salts are otherwise equivalent for purposes of this disclosure.

The term "pharmaceutically acceptable solvates" refers to solvates with water (i.e., hydrates, hemihydrate or sesquihydrate) or pharmaceutically acceptable solvents, for example solvates with common organic solvents as ethanol and the like. Such solvates are also encompassed within the scope of the disclosure.

Also encompassed herein are prodrugs of compounds described herein. In general, such prodrugs will be functional derivatives of these compounds, which are readily convertible in vivo into the required compound. Conventional procedures for the selection and preparation of prodrugs are known.

The compounds described herein may be metabolized in vivo and such metabolites are also encompassed herein.

The term "polymorphs" includes all crystalline forms, as well as amorphous form, of compounds described herein and as such are encompassed herein.

All isomers of compounds described herein are encompassed herein, either in admixture or in pure or substantially pure form.

Compounds described herein can have asymmetric carbon centers including in the substituents. Consequently, compounds of present invention can exist in enantiomeric or diastereomeric forms or in mixture thereof. The processes for the preparation can utilize racemates, enantiomers, or diastereomers as starting materials. When diastereomeric or enantiomeric products are prepared, they can be separated by conventional methods, for example, chromatographic or fractional crystallization.

The term "tautomer" includes one of two or more structural isomers that exist in equilibrium and are readily converted from one isomeric form to another. Certain compounds of the general Formula (I) may furthermore be present in tautomeric forms.

The term "regioisomers" refers to compounds, which have the same molecular formula but differ in the connectivity of the atoms.

The term "compounds of the invention" and equivalent expressions, as well as "compounds described herein" are meant to embrace compounds of Formula (I) as described herein, including pharmaceutically acceptable salts, pharmaceutically acceptable solvates, stereoisomers, tautomers, racemates, regioisomers, prodrugs, metabolites, polymorphs or N-oxides thereof, where the context so permits. In general and preferably, the compounds of the invention and the formulas designating the compounds of the invention are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits.

The term "stable compound" refers to a compound that is sufficiently robust to survive isolation to a useful degree of purity from a reaction mixture, and formulation into an efficacious therapeutic or diagnostic agent. For example, a compound, which would have a "dangling valency" or is a "carbanion" is not a compound contemplated by the invention.

The term "racemate" includes a mixture of equal amounts of left- and right-handed stereoisomers of chiral molecules.

When a bond to a substituent is shown to cross a bond connecting two atoms in a ring, then such substituent may be bonded to any atom on the ring.

The present disclosure includes all isotopes of atoms occurring in the present compounds. Isotopes include those atoms having the same atomic number but different mass numbers. By way of general example, and without limitation, isotopes of hydrogen include tritium and deuterium. Isotopes of carbon include C-13 and C-14.

The compounds described herein can be administered in conventional dosage forms prepared by combining active ingredient in an amount sufficient to produce 5-lipoxygenase pathway inhibiting activity with one or more non-toxic pharmaceutically acceptable carriers, adjuvants, diluents or vehicles, which are collectively referred to herein as carriers, according to conventional procedures. These procedures may involve mixing, granulating and compressing or dissolving the ingredients as appropriate to the desired preparation.

The pharmaceutical carrier employed may be, for example, either a solid or liquid. Exemplary of solid carriers include, for example, lactose, terra alba, sucrose, talc, gelatin, agar, pectin, acacia, magnesium stearate, stearic acid and the like. Exemplary of liquid carriers include, for example, syrup, peanut oil, olive oil, water and the like. Similarly, the carriers may include time delay material well known to the art for sustained-release or extended release, such as glyceryl monostearate or glyceryl distearate alone or with a wax.

A wide variety of pharmaceutical dosage forms can be employed. Thus, if a solid carrier is used, the preparation can be, for example, tableted, placed in a hard gelatin capsule in powder or pellet form or in the form of a troche or lozenge. When a liquid carrier is used, the preparation can be, for example, in the form of a syrup, emulsion, soft gelatin capsule, and sterile injectable liquid such as an ampule or non-aqueous liquid suspension.

Pharmaceutical compositions can be administered by any route of administration, including for example, orally, rectally, parenterally (intravenously, intramuscularly or subcutaneously), intracisternally, intravaginally, intraperitoneally, topically or by inhalation.

Solid dosage forms for oral administration may be presented in discrete units, for example, capsules, cachets, lozenges, tablets, pills, powders, dragees or granules, each containing a predetermined amount of the active compound. In such solid dosage forms, the active compound can be admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms can be prepared with coatings and shells, such as enteric coatings and others well known in this art. They may contain opacifying agents, and can also be formulated to release the active compound(s) in a certain part of the intestinal tract in a delayed manner. Examples of embedding compositions include, for example, polymeric substances and waxes.

Active compounds can also be in micro-encapsulated form, if appropriate, with one or more excipients or carriers.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

In addition to such inert diluents, dosage forms can also include adjuvants, for example, wetting agents, emulsifying and suspending agents, sweetening, flavoring and perfuming agents, colorants or dyes.

Suspensions, in addition to the active compounds, may contain suspending agents, as for example, ethoxylated isostearyl alcohols, polyoxyethylene sorbitol and sorbitan esters, microcrystalline cellulose, aluminium metahydroxide, bentonite, agar-agar and tragacanth, or mixtures of these substances, and the like.

Dosage forms for topical administration of compounds described herein include powder, spray, inhalant, ointment, creams, salve, jelly, lotion, paste, gel, aerosol, or oil. The active component can be admixed under sterile conditions with a pharmaceutically acceptable carrier and any needed preservatives, buffers or propellants as may be required. Ophthalmic formulations, eye ointments, powders and solutions are also encompassed herein.

Compositions suitable for parenteral injection may comprise pharmaceutically acceptable sterile aqueous or non-aqueous solutions, dispersions, suspensions or emulsions and sterile powders for reconstitution into sterile injectable solutions or dispersions. These preparations may contain antioxidants, buffers, bacteriostats and solutes, which render the compositions isotonic with the blood of the intended recipient. Aqueous and non-aqueous sterile suspensions may include suspending agents and thickening agents. The compositions may be presented in unit-dose or multi-dose containers, for example sealed ampoules and vials, and may be stored in a freeze-dried or lyophilized condition requiring only the addition of the sterile liquid carrier, for example, saline or water-for-injection immediately prior to use. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients. The compositions can be administered by the nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered nasally from devices which deliver the formulation in an appropriate manner.

Suppositories for rectal administration of a compound described herein can be prepared by mixing the drug with a suitable nonirritating excipient such as cocoa butter and polyethylene glycols or a suppository wax, which are solid at ordinary temperatures but liquid at body temperature and which therefore melt in the rectum or vaginal cavity and release the drug.

If desired, and for more effective distribution, compounds described herein can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions, which can be dissolved in sterile water, or some other sterile injectable medium immediately before use.

Actual dosage levels of active ingredient in pharmaceutical compositions described herein and spacing of individual dosages may be varied so as to obtain an amount of active ingredient that is effective to obtain a desired therapeutic response for a particular composition and method of administration. It will be understood, however, that the specific dose level for any particular patient will depend upon a variety of factors including the compound chosen, the body weight, general health, sex, diet, route of administration, the desired duration of treatment, rates of absorption and excretion, combination with other drugs and the severity of the particular disease being treated and is ultimately at the discretion of the physician.

Where desired, compounds described herein and/or their pharmaceutically acceptable salts, pharmaceutically acceptable solvates, stereoisomers, tautomers, racemates, regioisomers, prodrugs, metabolites, polymorphs or N-oxides may be advantageously used in combination with one or more other therapeutic agents. Examples of other therapeutic agents include but are not limited to, muscarinic receptor antagonists, PDE$_4$ inhibitors/PDE$_{3/4}$ inhibitors/PDE$_{4B}$ inhibitors/PDE$_7$ inhibitors, MMP9/12 inhibitors, caspase-1 inhibitors, beta 2 adrenoreceptor agonists, corticosteroids, p38 mitogen activated protein kinases, nuclear factor kappa B inhibitors, I kappa kinase inhibitors, VLA4 antagonists, thromboxane A2 antagonists, COX inhibitors, neutrophil elastase inhibitors, tachykinin receptor antagonists, secretory leukoprotease inhibitors, prostaglandin E analogues, adhesion molecule inhibitors, lipoxin agonists, tumour necrosis factor (TNF) inhibitors and other inflammatory cytokine inhibitors, chemokine inhibitors and chemokine receptor inhibitors, adenosine receptor antagonists, platelet activating factor antagonists, histamine release inhibitors, histamine receptor antagonists, nitric oxide synthase inhibitors, neurokinin antagonists or syk tyrosine kinase inhibitors.

While the present invention has been described in terms of its specific embodiments, certain modifications and equivalents will be apparent to those skilled in the art and are included within the scope of the present invention. The examples are provided to illustrate particular aspects of the disclosure and do not limit the scope of the present invention as defined by the claims.

EXAMPLES

Example 1

Synthesis of 2-(3-bromophenyl)acetamide

1-Hydroxybenzotriazole (HOBT, 13.82 g, 102.3 mmol), N-ethyldiisopropyl amine (Hunig's base, 13.22 g, 102.3 mmol) and ammonium carbonate (27.0 g, 279.0 mmol) were added to a solution of (3-bromophenyl)acetic acid (20.0 g, 93.0 mmol) in freshly dried and distilled tetrahydrofuran (80 mL) under a nitrogen atmosphere. The reaction mixture was stirred at room temperature for about 5 minutes and then cooled to 0° C. and stirred at the same temperature for about 1 hour. 1-(3-Dimethylaminopropyl)-3-ethylcarbodiimide hydrochloride (EDCLHCl, 19.61 g, 102.3 mmol) was added at 0° C. under nitrogen atmosphere. The reaction mixture was stirred at room temperature for about 12 hours. The solvent was evaporated under vacuum and water was added. A white solid was obtained which was filtered, washed with water and dried. Yield: 12.69 g.

$^1$H NMR (400 MHz, DMSO-d$_6$): δ7.52 (brs, 1H, —NH), 7.46 (s, 1H, Ar-H), 7.43-7.40 (m, 2H, Ar-H), 7.25-7.18 (m, 2H, Ar-H), 6.95 (brs, 1H, —NH) and 3.34 (s, 2H, —CH$_2$).

Mass Spectrum (m/z, +ve ion mode): 214 [M$^+$+1]

Example 2

Synthesis of (3-bromophenyl)acetonitrile 2-(3-Bromophenyl)acetamide (10.0 g, 46.73 mmol) (example 1) in dry 1,4-dioxane (100 mL) was cooled to 0° C. Triethylamine (18.91 g, 187.92 mmol) was added and the reaction mixture was stirred for about 10 minutes. Trifluoroacetic anhydride (39.26 g, 186.92 mmol) was added dropwise at 0° C. and the reaction mixture was stirred at room temperature for about 12 hours. The reaction mixture was poured into cold water, extracted with ethyl acetate, washed with water, dried over anhydrous sodium sulphate, filtered and the solvent evaporated under vacuum. An oily residue was obtained which was purified by column chromatography over silica gel using ethyl acetate and hexane (1:49) to afford the title compound as light yellow colored oil. Yield: 8.4 g.

$^1$H NMR (300 MHz, CDCl$_3$): δ7.49-7.46 (m, 2H, Ar-H), 7.27-7.23 (m, 2H, Ar-H) and 3.73 (s, 2H, —CH$_2$CN).

Mass Spectrum (m/z, +ve ion mode): 197 [M$^+$+1]

Example 3

Synthesis of 4-(3-bromophenyl)tetrahydro-2H-pyran-4-carbonitrile (3-Bromophenyl)acetonitrile (10.0 g, 51.02 mmol) (example 2) was added dropwise to a cold solution (0° C.) of sodium hydride (60% dispersion in mineral oil) (4.49 g, 112.24 mmol) in dry distilled dimethylformamide (80 mL) under nitrogen atmosphere. The reaction mixture was stirred for about 30 minutes. 15-Crown-5 (1.01 g, 5.10 mmol) was added and the reaction mixture was stirred at 0° C. for about 30 minutes. Bis-(2-choroethyl)ether (7.17 mL, 61.22 mmol) and sodium iodide (7.65 g, 51.02 mmol) were added at 0° C. The reaction mixture was stirred overnight, quenched with water, extracted with ethyl acetate and the combined extracts were washed with water and brine. The organic layer was dried over anhydrous sodium sulphate, filtered and the solvent evaporated under reduced pressure to form an orange colored residue. The residue was purified by column chromatography over silica gel using ethyl acetate and hexane (1:4) to afford the title compound as light yellow crystalline solid. Yield: 11.20 g $^1$H NMR (300 MHz, CDCl$_3$): δ7.63 (s, 1H, Ar-H), 7.54-7.42 (m, 2H, Ar-H), 7.35-7.27 (m, 1H, Ar-H), 4.11 (m, 2H, —OCH$_2$), 3.93-3.85 (m, 2H, —OCH$_2$) and 2.16-2.02 (m, 4H, (2x-CH$_2$).

Example 4

Synthesis of 4-{3-[(4-aminophenyl)thio]phenyl}tetrahydro-2H-pyran-4-carbonitrile A mixture of 4-(3-bromophenyl)tetrahydro-2H-pyran-4-carbonitrile (5.0 g, 18.79 mmol) (example 3), sodium carbonate (13.94 g, 131.58 mmol) and cesium carbonate (9.18 g, 28.19 mmol) was evacuated under vacuum for about 15 minutes. N-methyl pyrrolidinone (35 mL) and 4-aminothiophenol (2.8 g, 22.57 mmol) were added to this mixture under nitrogen atmosphere and heated at about 130° C. for about 15 hours. The reaction mixture was cooled to room temperature, poured over ice water and stirred. The mixture was extracted with ethyl acetate, washed with water, dried over anhydrous sodium sulphate, filtered and the solvent evaporated under vacuum to afford a brownish residue. Column chromatography over silica gel using ethyl acetate and hexane (3:2) yielded the title compound as a light yellow solid. Yield: 6.2 g.

$^1$H NMR (400 MHz, CDCl$_3$): δ7.34-7.20 (m, 5H, Ar-H), 7.03-7.00 (m, 1H, Ar-H), 6.72-6.70 (m, 2H, Ar-H), 4.07-3.90 (m, 2H, —OCH$_2$), 3.90-3.84 (m, 4H, —OCH$_2$ & 2x-NH) and 2.09-1.97 (m, 4H, 2x-CH$_2$).

Mass Spectrum (m/z, +ve ion mode): 311 [M$^+$+1]

Example 5

Synthesis of phenyl(4-{[3-(4-cyanotetrahydro-2H-pyran-4-yl)phenyl]thio}phenyl)carbamate A mixture of 4-{3-[(4-aminophenyl)thio]phenyl}tetrahydro-2H-pyran-4-carbonitrile (2.50 g, 8.06 mmol) (example 4) in 1,2-dichloroethane (20 mL) and pyridine (0.95 g, 12.097 mmol) was cooled to 0° C. Phenyl chloroformate (1.89 g, 12.097 mmol) was added dropwise to the reaction mixture at 0° C. The reaction mixture was stirred at room temperature for about 1 hour. The solvent was evaporated under vacuum, toluene was added to remove traces of pyridine, then hexane was added and the solid so obtained was filtered and dried. Yield:4.30 g.

$^1$H NMR (400 MHz, CDCl$_3$): δ7.50-7.39 (m, 6H, Ar-H), 7.36-7.27 (m, 4H, Ar-H), 7.21-7.16 (m, 3H, Ar-H), 7.00 (brs, 1H, —NH), 4.09-4.06 (m, 2H, —OCH$_2$), 3.92-3.85 (m, 2H, —OCH$_2$) and 2.12-2.00 (m, 4H, 2x-CH$_2$).

Mass Spectrum (m/z, +ve ion mode): 431 [M$^+$+1]

Example 6

Synthesis of N-(4-{[3-(4-cyanotetrahydro-2H-pyran-4-yl)phenyl]thio}phenyl)hydrazinecarboxamide Hydrazine hydrate (99%, 0.44 g, 8.72 mmol) was added to a solution of phenyl(4-{[3-(4-cyanotetrahydro-2H-pyran-4-yl)phenyl]thio}phenyl)carbamate (1.50 g, 3.49 mmol) (example 5) in 1,4-dioxane (10 mL). The reaction mixture was refluxed at 110° C. for about 4 hours. The solvent was evaporated under vacuum and water was added. The white solid so obtained was filtered under vacuum and dried to obtain the title compound. Yield: 1.0 g $^1$H NMR (300 MHz, DMSO-d$_6$): δ8.86 (s, 1H, —NH), 7.66-7.63 (m, 2H, Ar-H), 7.53 (s, 1H, —NH), 7.39-7.35 (m, 2H, Ar-H), 7.04 (s, 1H, —NH), 4.39 (s, 1H, Ar-H), 4.00-3.96 (m, 2H, —OCH$_2$), 3.65-3.57 (m, 2H, —OCH$_2$) and 2.03-1.96 (m, 4H, 2x-CH$_2$).

Mass Spectrum (m/z, +ve ion mode): 369 [M$^+$+1]

Example 7

Synthesis of 4-(3-{[4-(3-methyl-5-oxo-4,5-dihydro-1H-1,2,4-triazol-1-yl)phenyl]thio}phenyl)tetrahydro-2H-pyran-4-carbonitrile A mixture of N-(4-{[3-(4-cyanotetrahydro-2H-pyran-4-yl)phenyl]thio}phenyl) hydrazinecarboxamide (1.0 g, 2.72 mmol) (example 6) and acetamidine hydrochloride (1.16 g, 12.22 mmol) was evacuated for about 15 minutes. Dry dimethylformamide (10 mL) was added under nitrogen atmosphere and the mixture was heated at about 120° C. for about 7-8 hours. The solvent was evaporated under vacuum and a saturated solution of potassium carbonate was added until the mixture became basic. The resulting mixture was extracted with ethyl acetate, washed with water, dried over anhydrous sodium sulphate, filtered and the solvent evaporated under vacuum to afford a colorless oily residue, which was purified by column chromatography over silica gel using ethyl acetate and hexane (4:1) to yield the title product as a white fluffy solid. Yield: 0.500 g.

$^1$H NMR (300 MHz, CDCl$_3$): δ9.78 (brs, 1H, Ar-H), 7.57 (s, 1H, Ar-H), 7.44-7.39 (m, 4H, Ar-H), 7.32-7.24 (m, 3H, Ar-H), 4.10-4.07 (m, 2H, —OCH$_2$), 3.93-3.86 (m, 2H, —OCH$_2$), 2.16 (s, 3H, —CH$_3$) and 2.13-1.97 (m, 4H, 2x-CH$_2$)

Mass Spectrum (m/z, +ve ion mode): 393 [M$^+$+1]

Example 8

Synthesis of 4-(3-{[4-(5-oxo-4,5-dihydro-1H-1,2,4-triazol-1-yl)phenyl]thio}phenyl)tetrahydro-2H-pyran-4-carbonitrile A mixture of N-(4-{[3-(4-cyanotetrahydro-2H-pyran-4-yl)phenyl]thio}phenyl) hydrazinecarboxamide (2.0 g, 5.43 mmol) (example 6) and formamidine acetate (2.54 g, 24.45 mmol) was evacuated for about 15 minutes. Dry dimethylformamide (15 mL) was added under nitrogen atmosphere and the mixture was cooled to 0° C. Glacial acetic acid (5 mL) was added at 0° C. under nitrogen atmosphere and the mixture was stirred at room temperature for about 30 minutes. The reaction mixture was then heated at about 120° C. for about 7-8 hours. The solvent was evaporated under vacuum and a saturated solution of sodium bicarbonate was added until the solution became basic. A white semisolid separated out. The mixture was extracted with ethyl acetate, washed with water, dried over anhydrous sodium sulphate, filtered and the solvent evaporated under vacuum to afford a light yellow solid, which upon crystallization in ethyl acetate and methanol gave the title compound as a light yellow solid. Yield: 1.60 g $^1$H NMR (400 MHz, DMSO-d$_6$): δ12.33 (brs, 1H, —NH), 9.87 (s, 1H, Ar-H), 7.77-7.75 (m, 2H, Ar-H), 7.56-7.35 (m, 5H, Ar-H), 7.27-7.25 (m, 1H, Ar-H), 4.02-3.98 (m, 2H, —OCH$_2$), 3.67-3.60 (m, 2H, —OCH$_2$) and 2.11-2.98 (m, 4H, 2x-CH$_2$).

Mass Spectrum (m/z, +ve ion mode): 379 [M$^+$+1].

Example 9

Synthesis of 4-(3-{[4-(4-ethyl-3-methyl-5-oxo-4,5-dihydro-1H-1,2,4-triazol-1-yl)phenyl]thio}phenyl) tetrahydro-2H-pyran-4-carbonitrile (Compound No. 28)

Solid potassium carbonate (0.158 g, 1.14 mmol) was added to a solution of 4-(3-{[4-(3-methyl-5-oxo-4,5-dihydro-1H-1,2,4-triazol-1-yl)phenyl]thio}phenyl)tetrahydro-2H-pyran-4-carbonitrile (0.100 g, 0.2544 mmol) (example 7) in dry dimethylformamide (2 mL). The reaction mixture was stirred at room temperature for about 5 minutes. Ethyl iodide (0.105 g, 0.763 mmol) was added and the mixture was heated at about 90-100° C. for about 12 hours. The solvent was evaporated under vacuum, water was added and the mixture extracted with ethyl acetate. The organic layer was washed with water, dried over anhydrous sodium sulphate, filtered and the solvent evaporated under vacuum to afford a brown residue. The product was purified by preparative thin layer chromatography over silica gel using ethyl acetate and hexane (3:2) as the eluant. Yield: 0.080 g.

$^1$H NMR (300 MHz, CDCl$_3$): δ7.55 (s, 1H, Ar-H), 7.43-7.39 (m, 4H, Ar-H), 7.26-7.24 (m, 3H, Ar-H), 4.11-4.06 (m, 2H, —OCH$_2$), 3.94-3.83 (m, 4H, —OCH$_2$ & —NCH$_2$), 2.17-2.02 (m, 7H, Ar-CH$_3$ & 2x-CH$_2$) and 1.37 (t, 3H, 6.0 Hz, —CH$_3$).

Mass Spectrum (m/z, +ve ion mode): 421[M$^+$+1].

The following compounds were prepared similarly 4-(3-{[4-(3,4-Dimethyl-5-oxo-4,5-dihydro-1H-1,2,4-triazol-1-yl)phenyl]thio}phenyl)tetrahydro-2H-pyran-4-carbonitrile (Compound No. 27), Yield: 60 mg, $^1$H NMR (300 MHz, CDCl$_3$): 7.56 (s, 1H, Ar-H), 7.41-7.06 (m, 7H, Ar-H), 4.11-4.07 (m, 2H, —OCH$_2$), 3.93-3.86 (m, 2H, —OCH$_2$), 3.49 (s, 3H, —NCH$_3$), 2.16 (s, 3H, Ar-CH$_3$) and 2.13-2.03 (m, 4H, 2x-CH$_2$), 4-(3-{[4-(4-Isopropyl-3-methyl-5-oxo-4,5-dihydro-1H-1,2,4-triazol-1-yl)phenyl]thio}phenyl)tetrahydro-2H-pyran-4-carbonitrile (Compound No. 29), Yield: 100 mg, Mass Spectrum (m/z, +ve ion mode): 435 [M$^+$+1], 4-(3-{[4-(3-Methyl-5-oxo-4-propyl-4,5-dihydro-1H-1,2,4-triazol-1-yl)phenyl]thio}phenyl)tetrahydro-2H-pyran-4-carbonitrile (Compound No. 30), Yield: 100 mg, Mass Spectrum (m/z, +ve ion mode): 435 [M$^+$+1], 4-(3-{[4-(4-Cyclohexyl-3-methyl-5-oxo-4,5-dihydro-1H-1,2,4-triazol-1-yl)phenyl]thio}phenyl)tetrahydro-2H-pyran-4-carbonitrile (Compound No. 31), Yield: 80 mg, Mass Spectrum (m/z, +ve ion mode): 475 [M$^+$+1], 4-(3-{[4-(4-Isobutyl-3-methyl-5-oxo-4,5-dihydro-1H-1,2,4-triazol-1-yl)phenyl]thio}phenyl)tetrahydro-2H-pyran-4-carbonitrile (Compound No. 32), Yield: 90 mg, Mass Spectrum (m/z, +ve ion mode): 449 [M$^+$+1], 4-(3-{[4-(4-Butyl-3-methyl-5-oxo-4,5-dihydro-1H-1,2,4-triazol-1-yl)phenyl]thio}phenyl)tetrahydro-2H-pyran-4-carbonitrile (Compound No. 33), Yield: 100 mg, Mass Spectrum (m/z, +ve ion mode): 449 [M$^+$+1], 4-[3-({4-[4-(Cyclopropylmethyl)-3-methyl-5-oxo-4,5-dihydro-1H-1,2,4-triazol-1-yl]phenyl}thio)phenyl]tetrahydro-2H-pyran-4-carbonitrile (Compound No. 34), Yield: 95 mg, Mass Spectrum (m/z, +ve ion mode): 447 [M$^+$+1], 4-[3-({4-[4-(Cyclohexylmethyl)-3-methyl-5-oxo-4,5-dihydro-1H-1,2,4-triazol-1-yl]phenyl}thio)phenyl]tetrahydro-2H-pyran-4-carbonitrile (Compound No. 35), Yield: 80 mg, Mass Spectrum (m/z, +ve ion mode): 489 [M$^+$+1], 4-(3-{[4-(4-Cyclopentyl-3-methyl-5-oxo-4,5-dihydro-1H-1,2,4-triazol-1-yl)phenyl]thio}phenyl)tetrahydro-2H-pyran-4-carbonitrile (Compound No. 36), Yield: 100 mg, Mass Spectrum (m/z, +ve ion mode): 461 [M$^+$+1], 4-[3-({4-[4-(2-Chloroethyl)-3-methyl-5-oxo-4,5-dihydro-1H-1,2,4-triazol-1-yl]phenyl}thio)phenyl]tetrahydro-2H-pyran-4-carbonitrile (Compound No. 37), Yield: 80 mg, Mass Spectrum (m/z, +ve ion mode): 455 [M$^+$+1], 4-[3-({4-[4-(2-Hydroxyethyl)-3-methyl-5-oxo-4,5-dihydro-1H-1,2,4-triazol-1-yl]phenyl}thio)phenyl]tetrahydro-2H-pyran-4-carbonitrile (Compound No. 38), Yield: 80 mg, Mass Spectrum (m/z, +ve ion mode): 437 [M$^+$+1], 4-(3-{[4-(4-Allyl-3-methyl-5-oxo-4,5-dihydro-1H-1,2,4-triazol-1-yl)phenyl]thio}phenyl)tetrahydro-2H-pyran-4-carbonitrile (Compound No. 39), Yield: 120 mg, Mass Spectrum (m/z, +ve ion mode): 433 [M$^+$+1], 4-[3-({4-[3-Methyl-4-(2-morpholin-4-ylethyl)-5-oxo-4,5-dihydro-1H-1,2,4-triazol-1-yl]phenyl}thio)phenyl]tetrahydro-2H-pyran-4-carbonitrile (Compound No. 40), Yield: 100 mg, Mass Spectrum (m/z, +ve ion mode): 506 [M$^+$+1], 4-[3-({4-[4-(Cyanomethyl)-3-methyl-5-oxo-4,5-dihydro-1H-1,2,4-triazol-1-yl]phenyl}thio)phenyl]tetrahydro-2H-pyran-4-carbonitrile (Compound No. 41), Yield: 90 mg, Mass Spectrum (m/z, +ve ion mode): 454 [M$^+$+23], 4-(3-{[4-(4-Cycloheptyl-3-methyl-5-oxo-4,5-dihydro-1H-1,2,4-triazol-1-yl)phenyl]thio}phenyl)tetrahydro-2H-pyran-4-carbonitrile (Compound No. 42), Yield: 50 mg, $^1$H NMR (300 MHz, CDCl$_3$): δ7.46-7.38 (m, 4H, Ar-H), 7.32-7.28 (m, 3H, Ar-H), 7.13-7.12 (m, 1H, Ar-H), 4.10-4.05 (m, 2H, —OCH$_2$), 3.93-3.84 (m, 2H, —OCH$_2$), 3.07 (s, 3H, Ar-CH$_3$), 2.97-2.90 (m, 1H, —NCH) and 2.12-1.64 (brm, 16H, 8x-CH$_2$), The following compounds were prepared by following procedure of Example 9 by using 4-(3-{[4-(5-oxo-4,5-dihydro-1H-1,2,4-triazol-1-yl)phenyl]thio}phenyl)tetrahydro-2H-pyran-4-carbonitrile (example 8).

4-(3-{[4-(4-Methyl-5-oxo-4,5-dihydro-1H-1,2,4-triazol-1-yl)phenyl]thio}phenyl)tetrahydro-2H-pyran-4-carbonitrile (Compound No. 43), Yield: 90 mg, Mass Spectrum (m/z, +ve ion mode): 393 [M$^+$+1], 4-(3-{[4-(4-Ethyl-5-oxo-4,5-dihydro-1H-1,2,4-triazol-1-yl)phenyl]thio}phenyl)tetrahydro-2H-pyran-4-carbonitrile (Compound No. 44), Yield: 85 mg, Mass Spectrum (m/z, +ve ion mode): 407 [M$^+$+1], 4-(3-{[4-(5-Oxo-4-propyl-4,5-dihydro-1H-1,2,4-triazol-1-yl)phenyl]thio}phenyl)tetrahydro-2H-pyran-4-carbonitrile (Compound No. 45), Yield: 95 mg, $^1$H NMR (400 MHz, CDCl$_3$): δ7.96 (s, 1H, Ar-H), 7.70-7.55 (m, 2H, Ar-H), 7.49-7.37 (m, 5H, Ar-H), 7.29-7.26 (m, 1H, Ar-H), 4.10-4.07 (m, 2H, —OCH$_2$), 3.92-3.81 (m, 4H, —OCH$_2$ & —NCH$_2$), 2.11-2.05 (m, 4H, 2x-CH$_2$), 1.86-1.80 (m, 2H, —CH$_2$) and 0.98 (t, 3H, J=8.00 Hz, —CH$_3$), Mass Spectrum (m/z, +ve ion mode): 421 [M$^+$+1], 4-(3-{[4-(4-Isopropyl-5-oxo-4,5-dihydro-1H-1,2,4-triazol-1-yl)phenyl]thio}phenyl)tetrahydro-2H-pyran-4-carbonitrile (Compound No. 46), Yield: 70 mg, Mass Spectrum (m/z, +ve ion mode): 421 [M$^+$+1], 4-(3-{[4-(4-Butyl-5-oxo-4,5-dihydro-1H-1,2,4-triazol-1-yl)phenyl]thio}phenyl)tetrahydro-2H-pyran-4-carbonitrile (Compound No. 47), Yield: 70 mg, Mass Spectrum (m/z, +ve ion mode): 433 [M$^+$+1], 4-(3-{[4-(4-Isobutyl-5-oxo-4,5-dihydro-1H-1,2,4-triazol-1-yl)phenyl]thio}phenyl)tetrahydro-2H-pyran-4-carbonitrile (Compound No. 48), Yield: 87 mg, Mass Spectrum (m/z, +ve ion mode): 435 [M$^+$+1], 4-(3-{[4-(4-Cyclopropyl-5-oxo-4,5-dihydro-1H-1,2,4-triazol-1-yl)phenyl]thio}phenyl)tetrahydro-2H-pyran-4-carbonitrile (Compound No. 49), Yield: 60 mg, Mass Spectrum (m/z, +ve ion mode): 419 [M$^+$+1], 4-[3-({4-[4-(Cyclopropylmethyl)-5-oxo-4,5-dihydro-1H-1,2,4-triazol-1-yl]phenyl}thio)phenyl]tetrahydro-2H-pyran-4-carbonitrile (Compound No. 50), Yield: 60 mg, Mass Spectrum (m/z, +ve ion mode): 433 [M$^+$+1], 4-(3-{[4-(4-Cyclopentyl-5-oxo-4,5-dihydro-1H-1,2,4-triazol-1-yl)phenyl]thio}phenyl)tetrahydro-2H-pyran-4-carbonitrile (Compound No. 51), Yield: 80 mg, $^1$H NMR (400 MHz, CDCl$_3$): δ7.68 (s, 1H, Ar-H), 7.56-7.54 (m, 2H, Ar-H), 7.49-7.46 (m, 6H, Ar-H), 4.70 (m, 1H, —NCH), 4.10-4.06 (m, 2H, —OCH$_2$), 3.92-3.85 (m, 2H, —OCH$_2$), 2.10-2.02 (m, 6H, 3x-CH$_2$) and 1.93-1.88 (brm, 6H, 3x-CH$_2$), 4-(3-{[4-(4-Cyclohexyl-5-oxo-4,5-dihydro-1H-1,2,4-triazol-1-yl)phenyl]thio}phenyl)tetrahydro-2H-pyran-4-carbonitrile (Compound No. 52), Yield: 95 mg, Mass Spectrum (m/z, +ve ion mode): 461 [M$^+$+1], 4-[3-({4-[4-(Cyclohexylmethyl)-5-oxo-4,5-dihydro-1H-1,2,4-triazol-1-yl]phenyl}thio)phenyl]tetrahydro-2H-pyran-4-carbonitrile (Compound No. 53), Yield: 90 mg, Mass Spectrum (m/z, +ve ion mode): 475 [M$^+$+1], 4-(3-{[4-(4-Cycloheptyl-5-oxo-4,5-dihydro-1H-1,2,4-triazol-1-yl)phenyl]thio}phenyl)tetrahydro-2H-pyran-4-carbonitrile (Compound No. 54),
Yield: 85 mg,
Mass Spectrum (m/z, +ve ion mode): 475 [M$^+$+1],
4-(3-{[4-(4-Allyl-5-oxo-4,5-dihydro-1H-1,2,4-triazol-1-yl)phenyl]thio}phenyl)tetrahydro-2H-pyran-4-carbonitrile (Compound No. 55),
Yield: 65 mg,
Mass Spectrum (m/z, +ve ion mode): 419 [M$^+$+1],
4-(3-{[4-(5-Oxo-4-prop-2-yn-1-yl-4,5-dihydro-1H-1,2,4-triazol-1-yl)phenyl]thio}phenyl)tetrahydro-2H-pyran-4-carbonitrile (Compound No. 56),
Yield: 78 mg,
Mass Spectrum (m/z, +ve ion mode): 417 [M$^+$+1],
4-[3-({4-[4-(2-Hydroxyethyl)-5-oxo-4,5-dihydro-1H-1,2,4-triazol-1-yl]phenyl}thio)phenyl]tetrahydro-2H-pyran-4-carbonitrile (Compound No. 57),
Yield: 75 mg,
Mass Spectrum (m/z, +ve ion mode): 423 [M$^+$+1].

Example 10

Synthesis of 4-(3-{[4-(4-ethyl-3-methyl-5-oxo-4,5-dihydro-1H-1,2,4-triazol-1-yl)phenyl]thio}phenyl)tetrahydro-2H-pyran-4-carboxamide (Compound No. 1)

Solid potassium hydroxide (0.035 g, 0.6333 mmol) was added to a solution of 4-(3-{[4-(4-ethyl-3-methyl-5-oxo-4,5-dihydro-1H-1,2,4-triazol-1-yl)phenyl]thio}phenyl)tetrahydro-2H-pyran-4-carbonitrile (0.070 g, 0.166 mmol) (example 9) in isopropyl alcohol and methanol mixture (3 mL). The reaction mixture was heated at about 90-100° C. for about 12-15 hours. The solvent was evaporated under vacuum and water was added. A white solid separated out, which was filtered and dried under vacuum to afford the title compound. Yield: 0.045 g.
$^1$H NMR (300 MHz, CDCl$_3$): δ7.40-7.29 (m, 10H, Ar-H & 2x-NH), 3.88-3.75 (m, 6H, 2x-OCH$_2$ & —NCH$_2$), 2.36-2.32 (m, 2H, —CH$_2$), 2.16 (s, 3H, Ar-CH$_3$), 2.10-2.05 (m, 2H, —CH$_2$) and 1.37 (t, 3H, J=6.0 Hz, —CH$_3$).
Mass Spectrum (m/z, +ve ion mode): 439 [M$^+$+1]
The following compounds were prepared similarly:
4-(3-{[4-(4-Isobutyl-3-methyl-5-oxo-4,5-dihydro-1H-1,2,4-triazol-1-yl)phenyl]thio}phenyl)tetrahydro-2H-pyran-4-carboxamide (Compound No. 2),
Yield: 55 mg,
Mass Spectrum (m/z, +ve ion mode): 467 [M$^+$+1],
4-(3-{[4-(4-Cyclopentyl-3-methyl-5-oxo-4,5-dihydro-1H-1,2,4-triazol-1-yl)phenyl]thio}phenyl)tetrahydro-2H-pyran-4-carboxamide (Compound No. 3),
Yield: 40 mg,
Mass Spectrum (m/z, +ve ion mode): 479 [M$^+$+1],
4-(3-{[4-(3-Methyl-5-oxo-4-propyl-4,5-dihydro-1H-1,2,4-triazol-1-yl)phenyl]thio}phenyl)tetrahydro-2H-pyran-4-carboxamide (Compound No. 4),
Yield: 40 mg,
Mass Spectrum (m/z, +ve ion mode): 453 [M$^+$+1],
4-(3-{[4-(4-Isopropyl-3-methyl-5-oxo-4,5-dihydro-1H-1,2,4-triazol-1-yl)phenyl]thio}phenyl)tetrahydro-2H-pyran-4-carboxamide (Compound No. 5),
Yield: 40 mg,
Mass Spectrum (m/z, +ve ion mode): 453 [M$^+$+1],
4-(3-{[4-(4-Butyl-3-methyl-5-oxo-4,5-dihydro-1H-1,2,4-triazol-1-yl)phenyl]thio}phenyl)tetrahydro-2H-pyran-4-carboxamide (Compound No. 6),
Yield: 40 mg,
Mass Spectrum (m/z, +ve ion mode): 467 [M$^+$+1],
4-(3-{[4-(4-Allyl-3-methyl-5-oxo-4,5-dihydro-1H-1,2,4-triazol-1-yl)phenyl]thio}phenyl)tetrahydro-2H-pyran-4-carboxamide (Compound No. 8),
Yield: 30 mg,
Mass Spectrum (m/z, +ve ion mode): 451 [M$^+$+1],
4-[3-({4-[3-Methyl-4-(2-morpholin-4-ylethyl)-5-oxo-4,5-dihydro-1H-1,2,4-triazol-1-yl]phenyl}thio)phenyl]tetrahydro-2H-pyran-4-carboxamide (Compound No. 9),
Yield: 40 mg,
Mass Spectrum (m/z, +ve ion mode): 524 [M$^+$+1],
4-[3-({4-[4-(2-Chloroethyl)-3-methyl-5-oxo-4,5-dihydro-1H-1,2,4-triazol-1-yl]phenyl}thio)phenyl]tetrahydro-2H-pyran-4-carboxamide (Compound No. 10),
Yield: 12 mg,
Mass Spectrum (m/z, +ve ion mode): 473 [M$^+$+1],
4-[3-({4-[4-(Cyclohexylmethyl)-3-methyl-5-oxo-4,5-dihydro-1H-1,2,4-triazol-1-yl]phenyl}thio)phenyl]tetrahydro-2H-pyran-4-carboxamide (Compound No. 11),
Yield: 40 mg,
Mass Spectrum (m/z, +ve ion mode): 507 [M$^+$+1],
4-[3-({4-[4-(2-Hydroxyethyl)-3-methyl-5-oxo-4,5-dihydro-1H-1,2,4-triazol-1-yl]phenyl}thio)phenyl]tetrahydro-2H-pyran-4-carboxamide (Compound No. 12),
Yield: 10 mg,
Mass Spectrum (m/z, +ve ion mode): 455 [M$^+$+1],
4-(3-{[4-(4-Cyclohexyl-3-methyl-5-oxo-4,5-dihydro-1H-1,2,4-triazol-1-yl)phenyl]thio}phenyl)tetrahydro-2H-pyran-4-carboxamide (Compound No. 13),
Yield: 10 mg,
Mass Spectrum (m/z, +ve ion mode): 493 [M$^+$+1],
4-(3-{[4-(4-Methyl-5-oxo-4,5-dihydro-1H-1,2,4-triazol-1-yl)phenyl]thio}phenyl)tetrahydro-2H-pyran-4-carboxamide (Compound No. 14),
Yield: 30 mg,
Mass Spectrum (m/z, +ve ion mode): 411 [M$^+$+1],
4-(3-{[4-(4-Ethyl-5-oxo-4,5-dihydro-1H-1,2,4-triazol-1-yl)phenyl]thio}phenyl)tetrahydro-2H-pyran-4-carboxamide (Compound No. 15),
Yield: 32 mg,
Mass Spectrum (m/z, +ve ion mode): 425 [M$^+$+1],
4-(3-{[4-(5-Oxo-4-propyl-4,5-dihydro-1H-1,2,4-triazol-1-yl)phenyl]thio}phenyl)tetrahydro-2H-pyran-4-carboxamide (Compound No. 16),
Yield: 30 mg,
$^1$H NMR (400 MHz, CDCl$_3$+CD$_3$OD): δ8.12 (s, 1H, Ar-H) 7.5-7.14 (m, 8H, Ar-H), 7.14 (brs, 1H, —NH), 3.85-3.81 (m, 4H, 2x-OCH$_2$), 3.75-3.70 (m, 2H, —NCH$_2$), 2.42-2.39 (m, 2H, —CH$_2$), 2.07-2.00 (m, 2H, —CH$_2$), 1.88-1.79 (m, 2H, —CH$_2$) and 0.99 (t, 3H, J=8.00 Hz, —CH$_3$),
Mass Spectrum (m/z, +ve ion mode): 439 [M$^+$+1],
4-[3-({4-[4-(Cyclopropylmethyl)-5-oxo-4,5-dihydro-1H-1,2,4-triazol-1-yl]phenyl}thio)phenyl]tetrahydro-2H-pyran-4-carboxamide (Compound No. 17),
Yield: 30 mg,
Mass Spectrum (m/z, +ve ion mode): 451 [M$^+$+1],
4-(3-{[4-(4-Isopropyl-5-oxo-4,5-dihydro-1H-1,2,4-triazol-1-yl)phenyl]thio}phenyl)tetrahydro-2H-pyran-4-carboxamide (Compound No. 18),
Yield: 30 mg,
Mass Spectrum (m/z, +ve ion mode): 439 [M$^+$+1],
4-(3-{[4-(4-Butyl-5-oxo-4,5-dihydro-1H-1,2,4-triazol-1-yl)phenyl]thio}phenyl)tetrahydro-2H-pyran-4-carboxamide (Compound No. 19),
Yield: 33 mg,
Mass Spectrum (m/z, +ve ion mode): 453 [M$^+$+1], 4-(3-{[4-(4-Cyclopentyl-5-oxo-4,5-dihydro-1H-1,2,4-triazol-1-yl)phenyl]thio}phenyl)tetrahydro-2H-pyran-4-carboxamide (Compound No. 20), Yield: 25 mg, Mass Spectrum (m/z, +ve ion mode): 465 [M$^+$+1], 4-(3-{[4-(4-Isobutyl-5-oxo-4,5-dihydro-1H-1,2,4-triazol-1-yl)phenyl]thio}phenyl)tetrahydro-2H-pyran-4-carboxamide (Compound No. 21), Yield: 35 mg, Mass Spectrum (m/z, +ve ion mode): 453 [M$^+$+1], 4-(3-{[4-(4-Cyclohexyl-5-oxo-4,5-dihydro-1H-1,2,4-triazol-1-yl)phenyl]thio}phenyl)tetrahydro-2H-pyran-4-carboxamide (Compound No. 22), Yield: 15 mg, Mass Spectrum (m/z, +ve ion mode): 479 [M$^+$+1], 4-[3-({4- [4-(Cyclohexylmethyl)-5-oxo-4,5-dihydro-1H-1,2,4-triazol-1-yl]phenyl}thio)phenyl]tetrahydro-2H-pyran-4-carboxamide (Compound No. 23), Yield: 27 mg, Mass Spectrum (m/z, +ve ion mode): 493 [M$^+$+1], 4-(3-{[4-(4-Cycloheptyl-5-oxo-4,5-dihydro-1H-1,2,4-triazol-1-yl)phenyl]thio}phenyl)tetrahydro-2H-pyran-4-carboxamide (Compound No. 24), Yield: 23 mg, Mass Spectrum (m/z, +ve ion mode): 493 [M$^+$+1], 4-(3-{[4-(4-Allyl-5-oxo-4,5-dihydro-1H-1,2,4-triazol-1-yl)phenyl]thio}phenyl)tetrahydro-2H-pyran-4-carboxamide (Compound No. 25), Yield: 32 mg, Mass Spectrum (m/z, +ve ion mode): 437 [M$^+$+1], 4-[3-({4-[4-(2-Hydroxyethyl)-5-oxo-4,5-dihydro-1H-1,2,4-triazol-1-yl]phenyl}thio)phenyl]tetrahydro-2H-pyran-4-carboxamide (Compound No. 26), Yield: 30 mg, Mass Spectrum (m/z, +ve ion mode): 441 [M$^+$+1].

The following compound was prepared by following the procedure of example 10 by using 4-(3-{[4-(3-methyl-5-oxo-4,5-dihydro-1H-1,2,4-triazol-1-yl)phenyl]thio}phenyl)tetrahydro-2H-pyran-4-carbonitrile (example 7).

4-(3-{[4-(3-Methyl-5-oxo-4,5-dihydro-1H-1,2,4-triazol-1-yl)phenyl]thio}phenyl)tetrahydro-2H-pyran-4-carboxamide (Compound No. 7), Yield: 30 mg, Mass Spectrum (m/z, +ve ion mode): 411 [M$^+$+1].

Example 11

Synthesis of N-[(1E)-(dimethylamino)methylene]-4-(3-{[4-(3-methyl-5-oxo-4,5-dihydro-1H-1,2,4-triazol-1-yl)phenyl]thio}phenyl)tetrahydro-2H-pyran-4-carboxamide N,N-Dimethylformamide dimethyl acetal (15 mL) was added to 4-(3-{[4-(3-methyl-5-oxo-4,5-dihydro-1H-1,2,4-triazol-1-yl)phenyl]thio}phenyl)tetrahydro-2H-pyran-4-carboxamide (2.0 g, 4.88 mmol) (example 10) and the reaction mixture was refluxed for about 2 hours. The solvent was evaporated under reduced pressure to obtain a light brown paste. Yield: 3.0 g.

The following compound was prepared similarly by using N,N-dimethylacetamide dimethyl acetal.

N-[(1E)-1-(Dimethylamino)ethylidene]-4-(3-{[4-(3-methyl-5-oxo-4,5-dihydro-1H-1,2,4-traizol-1-yl)phenyl]thio}phenyl)tetrahydro-2H-pyran-4-carboxamide Yield: 1.20 g.

Example 12

Synthesis of 5-methyl-2-[4-({3-[4-(4H-1,2,4-triazol-3-yl)tetrahydro-2H-pyran-4-yl]phenyl}thio)phenyl]-2,4-dihydro-3H-1,2,4-triazol-3-one (Compound No. 68)

Hydrazine dihydrochloride (1.13 g, 10.75 mmol) in sodium hydroxide solution (5N, 3 mL) was added to a solution of N-[(1E)-(dimethylamino)methylene]-4-(3-{[4-(3-methyl-5-oxo-4,5-dihydro-1H-1,2,4-triazol-1-yl)phenyl]thio}phenyl)tetrahydro-2H-pyran-4-carboxamide (3.0 g, 2.15 mmol) (example 11) in 1,4-dioxane. Glacial acetic acid (30 mL, 70%) was added and the reaction mixture was stirred at room temperature for about 30 minutes and then at 90° C. for about 5 hours. The solvent was evaporated under vacuum and a saturated mixture was extracted with ethyl acetate, washed with water, dried over anhydrous sodium sulphate, filtered and the solvent evaporated under vacuum to afford a thick oily residue, which upon column chromatography over silica gel using methanol and ethyl acetate (1:19) afforded the title compound as white crystalline solid. Yield: 1.10 g $^1$H NMR (400 MHz, CDCl$_3$): δ10.55 (s, 1H, —NH), 8.23 (s, 1H, Ar-H), 7.40-7.34 (m, 4H, Ar-H), 7.29-7.18 (m, 4H, Ar-H), 6.58 (s, 1H, —NH), 3.91-3.89 (m, 2H, —OCH$_2$), 3.51-3.46 (m, 2H, —OCH$_2$), 2.60-2.57 (m, 2H, —CH$_2$), 2.27-2.20 (m, 2H, —OCH$_2$) and 2.06 (s, 3H, Ar-CH$_3$).

Mass Spectrum (m/z, +ve ion mode): 435 [M$^+$+1]

Example 13

Synthesis of 4,5-dimethyl-2-[4-({3-[4-(3-methyl-1,2,4-oxadiazol-5-yl)tetrahydro-2H-pyran-4-yl]phenyl}thio)phenyl]-2,4-dihydro-3H-1,2,4-triazol-3-one (Compound No. 69)

A solution of hydroxylamine hydrochloride (0.522 g, 7.52 mmol) in sodium hydroxide (1 M, 10 mL) was added to N-[(1E)-1-(dimethylamino)ethylidene]-4-(3-{[4-(3-methyl-5-oxo-4,5-dihydro-1H-1,2,4-triazol-1-yl)phenyl]thio}phenyl)tetrahydro-2H-pyran-4-carboxamide (1.20 g, 2.51 mmol) (example 11). 1,4-dioxane (7.5 mL) followed by glacial acetic acid (10 mL) were added to the mixture, the reaction mixture stirred for about 30 minutes at room temperature and then heated at 90° C. for about 10 hours. The solvent was evaporated under vacuum and a saturated solution of potassium carbonate was added until the solution became basic. The reaction mixture was extracted with ethyl acetate, washed with water, dried over anhydrous sodium sulphate, filtered and the solvent evaporated under vacuum to afford a thick oil residue which upon column chromatography over silica gel using ethyl acetate and hexane (4:1) gave the title compound as a thick oil. Yield: 0.60 g $^1$H NMR (300 MHz, CDCl$_3$): δ7.45 (s, 1H, Ar-H), 7.35-7.31 (m, 6H, Ar-H), 7.22-7.19 (m, 1H, Ar-H), 3.99-3.95 (m, 2H, —OCH$_2$), 3.68-3.51 (m, 2H, —OCH$_2$), 3.48 (s, 3H, Ar-CH$_3$), 2.73-2.68 (m, 2H, —CH$_2$), 2.31 (s, 3H, Ar-CH$_3$), 2.30-2.21 (m, 2H, —CH$_2$) and 2.15 (s, 3H, Ar-CH$_3$).

Mass Spectrum (m/z, +ve ion mode): 464 [M$^+$+1]

Example 14

Synthesis of 5-methyl-4-propyl-2-[4-({3-[4-(4-propyl-4H-1,2,4-triazol-3-yl)tetrahydro-2H-pyran-4-yl]phenyl}thio)phenyl]-2,4-dihydro-3H-1,2,4-triazol-3-one (Compound No. 60)

Solid potassium carbonate (0.127 g, 0.9216 mmol) was added to a solution of 5-methyl-2-[4-({3-[4-(4H-1,2,4-triazol-3-yl)tetrahydro-2H-pyran-4-yl]phenyl}thio)phenyl]-2, 4-dihydro-3H-1,2,4-triazol-3-one (0.100 g, 0.2304 mmol) (example 12) in dry dimethylformamide (3 mL). The reaction mixture was stirred at room temperature for about 5 minutes. N-Propyl bromide (0.113 g, 0.9216 mmol) was added and the mixture was heated at 90-100° C. for about 12 hours. The solvent was evaporated under vacuum, water was added and the mixture was extracted with ethyl acetate. The. organic layer was washed with water, dried over anhydrous sodium sulphate, filtered and the solvent evaporated under vacuum to afford an oily residue. The product was purified by preparative thin layer chromatography using ethyl acetate and hexane (1:1) as the eluant to yield the title compound as white solid. Yield: 70 mg.

$^1$H NMR (CDCl$_3$, 400 MHz): δ8.08 (s, 1H, Ar-H), 7.42-7.16 (m, 8H, Ar-H), 4.10-4.07 (t, 2H, J=7.00 Hz, —NCH$_2$), 3.90-3.78 (m, 2H, —OCH$_2$), 3.76-3.74 (m, 4H, —OCH$_2$ & —NCH$_2$), 2.68 (m, 2H, —CH$_2$), 2.16-2.14 (m, 5H, —CH$_2$ & Ar-CH$_3$), 1.89-1.78 (m, 4H, 2x-CH$_2$), 0.97 (t, 3H, J=8.00 Hz, —CH$_3$) and 0.89 (t, 3H, J=8.00 Hz, —CH$_3$).

Mass Spectrum (m/z, +ve ion mode): 519 [M$^+$+1].

The following compounds were prepared similarly
4,5-Dimethyl-2-[4-({3-[4-(4-methyl-4H-1,2,4-triazol-3-yl)tetrahydro-2H-pyran-4-yl]phenyl}thio)phenyl]-2,4-dihydro-3H-1,2,4-triazol-3-one (Compound No. 58), Mass Spectrum (m/z, +ve ion mode): 463 [M$^+$+1],
4-Ethyl-2-[4-({3-[4-(4-ethyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 59), Mass Spectrum (m/z, +ve ion mode): 491 [M$^+$+1],
4-Isopropyl-2-[4-({3-[4-(4-isopropyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 61), Mass Spectrum (m/z, +ve ion mode): 519 [M$^+$+1],
4-Butyl-2-[4-({3-[4-(4-butyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 62), Mass Spectrum (m/z, +ve ion mode): 547 [M$^+$+1],
4-Isobutyl-2-[4-({3-[4-(4-isobutyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 63), Mass Spectrum (m/z, +ve ion mode): 547 [M$^+$+1],
4-Cyclopentyl-2-[4-({3-[4-(4-cyclopentyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 64), Mass Spectrum (m/z, +ve ion mode): 571 [M$^+$+1],
4-Cyclohexyl-2-[4-({3-[4-(4-cyclohexyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 65), Mass Spectrum (m/z, +ve ion mode): 599 [M$^+$+1],
4-Cycloheptyl-2-[4-({3-[4-(4-cycloheptyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 66), Mass Spectrum (m/z, +ve ion mode): 627 [M$^+$+1],
4-Allyl-2-[4-({3-[4-(4-allyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 67), Mass Spectrum (m/z, +ve ion mode): 515 [M$^+$+1].

Example 15

Synthesis of 4-(3-{[4-(3-methyl-5-oxo-4,5-dihydro-1H-1,2,4-triazol-1-yl)phenyl]thio}phenyl)tetrahydro-2H-pyran-4-carboxylic acid Potassium hydroxide (3.0 mmol) is added to a solution of 4-(3-{[4-(3-methyl-5-oxo-4,5-dihydro-1H-1,2,4-triazol-1-yl)phenyl]thio}phenyl)tetrahydro-2H-pyran-4-carboxamide (1.0 mmol) (example 10) in methanol and tetrahydrofuran (1:2) and the reaction mixture is refluxed for about 18 hours. The solvent is evaporated under vacuum. A small amount of water and concentrated hydrochloric acid are added to the residue to separate out the title compound.

Example 16

Synthesis of 4-(3-{[4-(3-methyl-5-oxo-4,5-dihydro-1H-1,2,4-triazol-1-yl)phenyl]thio}phenyl)-N-prop-2-yn-1-yltetrahydro-2H-pyran-4-carboxamide 1-(3-Dimethylaminopropyl)-3-ethylcarbodiimide hydrochloride (EDCL HCl) (1.0 mmol) is added to a mixture of 4-(3-{[4-(3-methyl-5-oxo-4,5-dihydro-1H-1,2,4-triazol-1-yl)phenyl]thio}phenyl)tetrahydro-2H-pyran-4-carboxylic acid (1.0 mmol) (example 15), 1-hydroxybenzotriazole (1.0 mmol), N-methylmorpholine (1.65 mmol) and propargylamine (1.0 mmol) in dichloromethane-dimethylformamide (1:1) at 0° C. The solution is stirred overnight at room temperature, washed with water and the aqueous layer is extracted with dichloromethane. The combined organic extracts are dried with sodium sulphate, filtered and the solvent is evaporated under reduced pressure. The residue is purified by column chromatography over silica gel to yield the title product.

Example 17

Synthesis of 5-methyl-2-[4-({3-[4-(5-methyl-1,3-oxazol-2-yl)tetrahydro-2H-pyran-4-yl]phenyl}thio)phenyl]-2,4-dihydro-3H-1,2,4-triazol-3-one (Compound No. 70)

A solution of 4-(3-{[4-(3-methyl-5-oxo-4,5-dihydro-1H-1,2,4-triazol-1-yl)phenyl]thio}phenyl)-N-prop-2-yn-1-yltetrahydro-2H-pyran-4-carboxamide (1.0 mmol) (example 16) and mercuric acetate (0.11 mmol) in acetic acid is heated at reflux for about 3 hours. All the volatiles are removed under reduced pressure and an aqueous solution of saturated potassium carbonate is added to the residue. The mixture is then extracted with dichloromethane, and the organic layer is dried over anhydrous sodium sulphate, filtered and concentrated under reduced pressure. The residue is then purified by column chromatography over silica gel to yield the title compound.

Example 18

Synthesis of 4,5-dimethyl-2-[4-({3-[4-(5-methyl-1,3-oxazol-2-yl)tetrahydro-2H-pyran-4-yl]phenyl}thio)phenyl]-2,4-dihydro-3H-1,2,4-triazol-3-one Compound No. 71)

Solid potassium carbonate (4.5 mmol) is added to a solution of 5-methyl-2-[4-({3-[4-(5-methyl-1,3-oxazol-2-yl)tetrahydro-2H-pyran-4-yl]phenyl}thio)phenyl]-2,4-dihydro-3H-1,2,4-triazol-3-one (1.0 mmol) (example 17) in dry dimethylformamide. The reaction mixture is stirred a room temperature for about 15 minutes. Methyl iodide (3.0 mmol) is added and the reaction mixture is heated at about 100° C. for about 12 hours. The solvent is evaporated under vacuum, water is added and the reaction mixture is extracted with ethyl acetate. The organic layer is washed with water, dried over anhydrous sodium sulphate, filtered and the solvent is evaporated to afford the residue. Column chromatography of the reside over silica gel affords the title compound.

Example 19

Synthesis of ethyl 4-(3-{[4-(3-methyl-5-oxo-4,5-dihydro-1H-1,2,4-traizol-1-yl)phenyl]thio}phenyl)tetrahydro-2H-pyran-4-carboxylate Ethanol is added to a solution of 4-(3-{[4-(3-methyl-5-oxo-4,5-dihydro-1H-1,2,4-traizol-1-yl)phenyl]thio}phenyl)tetrahydro-2H-pyran-4-carboxylic acid (1.0 mmol) (example 15) and the reaction mixture is cooled to 0° C. The mixture is stirred for about 15 minutes. Thionyl chloride (1.2 mmol) is added dropwise at 0° C. and the reaction mixture is stirred at room temperature for about 2 hours. The solvent is evaporated under vacuum, dichloromethane is added and the mixture is washed with a cold solution of sodium bicarbonate. The organic layer is dried over sodium sulphate, filtered and the solvent is evaporated to afford the title compound.

Example 20

Synthesis of N-(2-hydroxyethyl)-4-(3-{[4-(3-methyl-5-oxo-4,5-dihydro-1H-1,2,4-triazol-1-yl)phenyl]thio}phenyl)tetrahydro-2H-pyran-4-carboxamide 2-Ethanolamine (6.0 mmol) is added to a solution of ethyl 4-(3-{[4-(3-methyl-5-oxo-4,5-dihydro-1H-1,2,4-triazol-1-yl)phenyl]thio}phenyl)tetrahydro-2H-pyran-4-carboxylate (1.0 mmol) (example 19) in ethanol and the mixture are refluxed. All the volatiles are removed under reduced pressure and the residue is purified by column chromatography over silica gel to afford the title compound.

Example 21

Synthesis of 2-[4-({3-[4-(4,5-dimethyl-4,5-dihydro-1,3-oxazol-2-yl)tetrahydro-2H-pyran-4-yl]phenyl}thio)phenyl]-5-methyl-2,4-dihydro-3H-1,2,4-triazol-3-one (Compound No. 72)

Triethylamine (5.0 mmol) and carbon tetrachloride (5.0 mmol) are added dropwise to a solution of N-(2-hydroxyethyl)-4-(3-{[4-(3-methyl-5-oxo-4,5-dihydro-1H-1,2,4-triazol-1-yl)phenyl]thio}phenyl)tetrahydro-2H-pyran-4-carboxamide (1.0 mmol) (example 20) in acetonitrile. The reaction mixture is stirred at room temperature for about 3 hours. The solution is filtered and the filtrate is concentrated under reduced pressure to afford the residue. Column chromatography of the residue over silica gel affords the title compound.

Example 22

Synthesis of 2-[4-({3-[4-(4,5-dimethyl-4,5-dihydro-1,3-oxazol-2-yl)tetrahydro-2H-pyran-4-yl]phenyl}thio)phenyl]-4,5-dimethyl-2,4-dihydro-3H-1,2,4-triazol-3-one (Compound No. 73)

Solid potassium carbonate (4.5 mmol) is added to a solution of 2-[4-({3-[4-(4,5-dimethyl-4,5-dihydro-1,3-oxazol-2-yl)tetrahydro-2H-pyran-4-yl]phenyl}thio)phenyl]-5-methyl-2,4-dihydro-3H-1,2,4-traizol-3-one (1.0 mmol) (example 21) in dry dimethylformamide. The reaction mixture is stirred a room temperature for about 15 minutes. Methyl iodide (3.0 mmol) is added and the reaction mixture is heated at about 100° C. for about 12 hours. The solvent is evaporated under vacuum, water is added and the reaction mixture is extracted with ethyl acetate. The organic layer is washed with water, dried over anhydrous sodium sulphate, filtered and the solvent is evaporated to afford the residue. Column chromatography of the residue over silica gel affords the title compound.

Example 23

Efficacy of Compounds as 5-Lipoxygenase Inhibitors

5-Lipoxygenase Enzyme Inhibition

The assay was carried out in 96 well UV plate containing 100 μL reaction mixture 1,4-dithiothreitol (DTT) 200 μM; adenosine triphosphate (ATP), 100 μM; and calcium chloride, 100 μM; in a phosphate buffered saline in the absence and presence of different concentrations of test compounds (100 nM-10 μM) and 12 U (3 U μL$^{-1}$) of human recombinant 5-lipoxygenase (Cayman Chemicals Co., USA). The reaction mixture was incubated at 37° C. for 5 minutes, and the reaction initiated by adding 1 μL of 1 mM freshly prepared arachidonic acid. Increase in absorbance was monitored at 234 nm for 10 minutes. (J. Biol. Chem., 261, 11512-11519, 1986). A plot of absorbance vs. time curve was prepared and the area under the curve (AUC) was computed for each well. Percent inhibition of AUC for different treatments was calculated with respect to the difference between the arachidonic acid stimulated and negative control values, to compute $IC_{50}$ values. The assay was repeated with the same protocol in the absence of DTT to mimic non-reducing condition and $IC_{50}$ values were computed.

$IC_{50}$ values for some of the compounds tested were from about 0.2 μM to about >10 μM, from about 0.2 μM to about 3 μM, and even from about 0.2 μM to about 0.65 μM.

Cell Based Assay: A23187 Induced $LTB_4$ Release

Neutrophils were isolated from freshly drawn human blood after dextran sedimentation and ficoll separation (Eur. J. Biochem., 169, 175, 1987). The neutrophil suspension (0.2×10$^6$ cells/mL) was incubated in polystyrene microtitre plates with test compound in a 24 well plate and incubated at 37° C. for 1 hour and 0.25 mM Ca$^{++}$/Mg$^{++}$ was added in the final 3 minutes of incubation period. The reaction was initiated by adding 0.3 μg mL$^{-1}$ A23187 (Sigma-Aldrich Co, USA) and continued for 10 minutes at 37° C. The reaction was stopped by adding 80 μL of cold methanol (J. Pharmacol. Exp. Ther. 297, 267, 2001). The samples were analyzed for $LTB_4$ assay using $LTB_4$ ELISA kits. The amount of $LTB_4$ released was quantified and percent inhibition of $LTB_4$ release was calculated with respect to the difference between the A23187 stimulated and negative control cells, to compute $IC_{50}$ values.

For $IC_{50}$ values for some of the compounds tested were from about 0.7 μM to about >10 μM, from about 0.7 μM to about 3 μM, and even from about 0.7 μM to about 1 μM.

We claim:

1. A compound having the structure of Formula I:

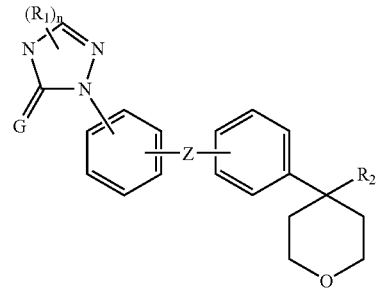

Formula I or a pharmaceutically acceptable salt, pharmaceutically acceptable, stereoisomer, tautomer, racemate, or N-oxide thereof, wherein G is O or S,
Z is —$(CH_2)_{n2}$—X— or —X—$(CH_2)_{n2}$—,
X is —$NR_1$, —O— or —S—,
$n_1$ is 0, 1 or 2,
$n_2$ is 0, 1 or 2
$R_1$ is hydrogen, alkyl, alkenyl, alkynyl, cycloalkyl, (cycloalkyl)alkyl, aryl, aralkyl, heteroaryl, heterocyclyl, (heteroaryl)alkyl, or (heterocyclyl)alkyl,
$R_2$ is —CN, —$COR_3$, or a 5-membered heteroaryl or heterocyclyl, and
$R_3$ is hydrogen, alkyl, alkenyl, alkynyl, cycloalkyl, (cycloalkyl)alkyl, aryl, aralkyl, heteroaryl, heterocyclyl, (heteroaryl)alkyl, (heterocyclyl)alkyl, —$OR_1$, —$SR_1$ or —$N(R_1)_2$.

2. A compound selected from 4-(3-{[4-(4-Ethyl-3-methyl-5-oxo-4,5-dihydro-1H-1,2,4-triazol-1-yl)phenyl]thio}phenyl)tetrahydro-2H-pyran-4-carboxamide (Compound No. 1), 4-(3-{[4-(4-Isobutyl-3-methyl-5-oxo-4,5-dihydro-1H-1,2,4-triazol-1-yl)phenyl]thio}phenyl)tetrahydro-2H-pyran-4-carboxamide (Compound No. 2), 4-(3-{[4-(4-Cyclopentyl-3-methyl-5-oxo-4,5-dihydro-1H-1,2,4-triazol-1-yl)phenyl]thio}phenyl)tetrahydro-2H-pyran-4-carboxamide (Compound No. 3), 4-(3-{[4-(3-Methyl-5-oxo-4-propyl-4,5-dihydro-1H-1,2,4-triazol-1-yl)phenyl]thio}phenyl)tetrahydro-2H-pyran-4-carboxamide (Compound No. 4), 4-(3-{[4-(4-Isopropyl-3-methyl-5-oxo-4,5-dihydro-1H-1,2,4-triazol-1-yl)phenyl]thio}phenyl)tetrahydro-2H-pyran-4-carboxamide (Compound No. 5), 4-(3-{[4-(4-Butyl-3-methyl-5-oxo-4,5-dihydro-1H-1,2,4-triazol-1-yl)phenyl]thio}phenyl)tetrahydro-2H-pyran-4-carboxamide (Compound No. 6), 4-(3-{[4-(3-Methyl-5-oxo-4,5-dihydro-1H-1,2,4-triazol-1-yl)phenyl]thio}phenyl)tetrahydro-2H-pyran-4-carboxamide (Compound No. 7), 4-(3-{[4-(4-Allyl-3-methyl-5-oxo-4,5-dihydro-1H-1,2,4-triazol-1-yl)phenyl]thio}phenyl)tetrahydro-2H-pyran-4-carboxamide (Compound No. 8), 4-[3-({4-[3-Methyl-4-(2-morpholin-4-ylethyl)-5-oxo-4,5-dihydro-1H-1,2,4-triazol-1-yl]phenyl}thio)phenyl]tetrahydro-2H-pyran-4-carboxamide (Compound No. 9), 4-[3-({4-[4-(2-Chloroethyl)-3-methyl-5-oxo-4,5-dihydro-1H-1,2,4-triazol-1-yl]phenyl}thio)phenyl]tetrahydro-2H-pyran-4-carboxamide (Compound No. 10), 4-[3-({4-[4-(Cyclohexylmethyl)-3-methyl-5-oxo-4,5-dihydro-1H-1,2,4-triazol-1-yl]phenyl}thio)phenyl]tetrahydro-2H-pyran-4-carboxamide (Compound No. 11), 4-[3-({4-[4-(2-Hydroxyethyl)-3-methyl-5-oxo-4,5-dihydro-1H-1,2,4-triazol-1-yl]phenyl}thio)phenyl]tetrahydro-2H-pyran-4-carboxamide (Compound No. 12), 4-(3-{[4-(4-Cyclohexyl-3-methyl-5-oxo-4,5-dihydro-1H-1,2,4-triazol-1-yl)phenyl]thio}phenyl)tetrahydro-2H-pyran-4-carboxamide (Compound No. 13), 4-(3-{[4-(4-Methyl-5-oxo-4,5-dihydro-1H-1,2,4-triazol-1-yl)phenyl]thio}phenyl)tetrahydro-2H-pyran-4-carboxamide (Compound No. 14), 4-(3-{[4-(4-Ethyl-5-oxo-4,5-dihydro-1H-1,2,4-triazol-1-yl)phenyl]thio}phenyl)tetrahydro-2H-pyran-4-carboxamide (Compound No. 15), 4-(3-{[4-(5-Oxo-4-propyl-4,5-dihydro-1H-1,2,4-triazol-1-yl)phenyl]thio}phenyl)tetrahydro-2H-pyran-4-carboxamide (Compound No. 16), 4-[3-({4-[4-(Cyclopropylmethyl)-5-oxo-4,5-dihydro-1H-1,2,4-triazol-1-yl]phenyl}thio)phenyl]tetrahydro-2H-pyran-4-carboxamide (Compound No. 17), 4-(3-{[4-(4-Isopropyl-5-oxo-4,5-dihydro-1H-1,2,4-triazol-1-yl)phenyl]thio}phenyl)tetrahydro-2H-pyran-4-carboxamide (Compound No. 18), 4-(3-{[4-(4-Butyl-5-oxo-4,5-dihydro-1H-1,2,4-triazol-1-yl)phenyl]thio}phenyl)tetrahydro-2H-pyran-4-carboxamide (Compound No. 19), 4-(3-{[4-(4-Cyclopentyl-5-oxo-4,5-dihydro-1H-1,2,4-triazol-1-yl)phenyl]thio}phenyl)tetrahydro-2H-pyran-4-carboxamide (Compound No. 20), 4-(3-{[4-(4-Isobutyl-5-oxo-4,5-dihydro-1H-1,2,4-triazol-1-yl)phenyl]thio}phenyl)tetrahydro-2H-pyran-4-carboxamide (Compound No. 21), 4-(3-{[4-(4-Cyclohexyl-5-oxo-4,5-dihydro-1H-1,2,4-triazol-1-yl)phenyl]thio}phenyl)tetrahydro-2H-pyran-4-carboxamide (Compound No. 22), 4-[3-({4- [4-(Cyclohexylmethyl)-5-oxo-4,5-dihydro-1H-1,2,4-triazol-1-yl]phenyl}thio)phenyl]tetrahydro-2H-pyran-4-carboxamide (Compound No. 23), 4-(3-{[4-(4-Cycloheptyl-5-oxo-4,5-dihydro-1H-1,2,4-triazol-1-yl)phenyl]thio}phenyl)tetrahydro-2H-pyran-4-carboxamide (Compound No. 24), 4-(3-{[4-(4-Allyl-5-oxo-4,5-dihydro-1H-1,2,4-triazol-1-yl)phenyl]thio}phenyl)tetrahydro-2H-pyran-4-carboxamide (Compound No. 25), 4-[3-({4-[4-(2-Hydroxyethyl)-5-oxo-4,5-dihydro-1H-1,2,4-triazol-1-yl]phenyl}thio)phenyl]tetrahydro-2H-pyran-4-carboxamide (Compound No. 26), 4-(3-{[4-(3,4-Dimethyl-5-oxo-4,5-dihydro-1H-1,2,4-triazol-1-yl)phenyl]thio}phenyl)tetrahydro-2H-pyran-4-carbonitrile (Compound No. 27), 4-(3-{[4-(4-Ethyl-3-methyl-5-oxo-4,5-dihydro-1H-1,2,4-triazol-1-yl)phenyl]thio}phenyl)tetrahydro-2H-pyran-4-carbonitrile (Compound No. 28), 4-(3-{[4-(4-Isopropyl-3-methyl-5-oxo-4,5-dihydro-1H-1,2,4-triazol-1-yl)phenyl]thio}phenyl)tetrahydro-2H-pyran-4-carbonitrile (Compound No. 29), 4-(3-{[4-(3-Methyl-5-oxo-4-propyl-4,5-dihydro-1H-1,2,4-triazol-1-yl)phenyl]thio}phenyl)tetrahydro-2H-pyran-4-carbonitrile (Compound No. 30), 4-(3-{[4-(4-Cyclohexyl-3-methyl-5-oxo-4,5-dihydro-1H-1,2,4-triazol-1-yl)phenyl]thio}phenyl)tetrahydro-2H-pyran-4-carbonitrile (Compound No. 31), 4-(3-{[4-(4-Isobutyl-3-methyl-5-oxo-4,5-dihydro-1H-1,2,4-triazol-1-yl)phenyl]thio}phenyl)tetrahydro-2H-pyran-4-carbonitrile (Compound No. 32), 4-(3-{[4-(4-Butyl-3-methyl-5-oxo-4,5-dihydro-1H-1,2,4-triazol-1-yl)phenyl]thio}phenyl)tetrahydro-2H-pyran-4-carbonitrile (Compound No. 33), 4-[3-({4-[4-(Cyclopropylmethyl)-3-methyl-5-oxo-4,5-dihydro-1H-1,2,4-triazol-1-yl]phenyl}thio)phenyl]tetrahydro-2H-pyran-4-carbonitrile (Compound No. 34), 4-[3-({4-[4-(Cyclohexylmethyl)-3-methyl-5-oxo-4,5-dihydro-1H-1,2,4-triazol-1-yl]phenyl}thio)phenyl]tetrahydro-2H-pyran-4-carbonitrile (Compound No. 35), 4-(3-{[4-(4-Cyclopentyl-3-methyl-5-oxo-4,5-dihydro-1H-1,2,4-triazol-1-yl)phenyl]thio}phenyl)tetrahydro-2H-pyran-4-carbonitrile (Compound No. 36), 4-[3-({4-[4-(2-Chloroethyl)-3-methyl-5-oxo-4,5-dihydro-1H-1,2,4-triazol-1-yl]phenyl}thio)phenyl]tetrahydro-2H-pyran-4-carbonitrile (Compound No. 37), 4-[3-({4-[4-(2-Hydroxyethyl)-3-methyl-5-oxo-4,5-dihydro-1H-1,2,4-triazol-1-yl]phenyl}thio)phenyl]tetrahydro-2H-pyran-4-carbonitrile (Compound No. 38), 4-(3-{[4-(4-Allyl-3-methyl-5-oxo-4,5-dihydro-1H-1,2,4-triazol-1-yl)phenyl]thio}phenyl)tetrahydro-2H-pyran-4-carbonitrile (Compound No. 39), 4-[3-({4-[3-Methyl-4-(2-morpholin-4-ylethyl)-5-oxo-4,5-dihydro-1H-1,2,4-triazol-1-yl]phenyl}thio)phenyl]tetrahydro-2H-pyran-4-carbonitrile (Compound No. 40), 4-[3-({4-[4-(Cyanomethyl)-3-methyl-5-oxo-4,5-dihydro-1H-1,2,4-triazol-1-yl]phenyl}thio)phenyl]tetrahydro-2H-pyran-4-carbonitrile (Compound No. 41), 4-(3-{[4-(4-Cycloheptyl-3-methyl-5-oxo-4,5-dihydro-1H-1,2,4-triazol-1-yl)phenyl]thio}phenyl)tetrahydro-2H-pyran-4-carbonitrile (Compound No. 42), 4-(3-{[4-(4-Methyl-5-oxo-4,5-dihydro-1H-1,2,4-triazol-1-yl)phenyl]thio}phenyl)tetrahydro-2H-pyran-4-carbonitrile (Compound No. 43), 4-(3-{[4-(4-Ethyl-5-oxo-4,5-dihydro-1H-1,2,4-triazol-1-yl)phenyl]thio}phenyl)tetrahydro-2H-pyran-4-carbonitrile (Compound No. 44), 4-(3-{[4-(5-Oxo-4-propyl-4,5-dihydro-1H-1,2,4-triazol-1-yl)phenyl]thio}phenyl)tetrahydro-2H-pyran-4-carbonitrile (Compound No. 45), 4-(3-{[4-(4-Isopropyl-5-oxo-4,5-dihydro-1H-1,2,4-triazol-1-yl)phenyl]thio}phenyl)tetrahydro-2H-pyran-4-carbonitrile (Compound No. 46), 4-(3-{[4-(4-Butyl-5-oxo-4,5-dihydro-1H-1,2,4-triazol-1-yl)phenyl]thio}phenyl)tetrahydro-2H-pyran-4-carbonitrile (Compound No. 47), 4-(3-{[4-(4-Isobutyl-5-oxo-4,5-dihydro-1H-1,2,4-triazol-1-yl)phenyl]thio}phenyl)tetrahydro-2H-pyran-4-carbonitrile (Compound No. 48), 4-(3-{[4-(4-Cyclopropyl-5-oxo-4,5-dihydro-1H-1,2,4-triazol-1-yl)phenyl]thio}phenyl)tetrahydro-2H-pyran-4-carbonitrile (Compound No. 49), 4-[3-({4-[4-(Cyclopropylmethyl)-5-oxo-4,5-dihydro-1H-1,2,4-triazol-1-yl]phenyl}thio)phenyl]tetrahydro-2H-pyran-4-carbonitrile (Compound No. 50), 4-(3-{[4-(4-Cyclopentyl-5-oxo-4,5-dihydro-1H-1,2,4-triazol-1-yl)phenyl]thio}phenyl)tetrahydro-2H-pyran-4-carbonitrile (Compound No. 51), 4-(3-{[4-(4-Cyclohexyl-5-oxo-4,5-dihydro-1H-1,2,4-triazol-1-yl)phenyl]thio}phenyl)tetrahydro-2H-pyran-4-carbonitrile (Compound No. 52), 4-[3-({4-[4-(Cyclohexylmethyl)-5-oxo-4,5-dihydro-1H-1,2,4-triazol-1-yl]phenyl}thio)phenyl]tetrahydro-2H-pyran-4-carbonitrile (Compound No. 53), 4-(3-{[4-(4-Cycloheptyl-5-oxo-4,5-dihydro-1H-1,2,4-triazol-1-yl)phenyl]thio}phenyl)tetrahydro-2H-pyran-4-carbonitrile (Compound No. 54), 4-(3-{[4-(4-Allyl-5-oxo-4,5-dihydro-1H-1,2,4-triazol-1-yl)phenyl]thio}phenyl)tetrahydro-2H-pyran-4-carbonitrile (Compound No. 55), 4-(3-{[4-(5-Oxo-4-prop-2-yn-1-yl-4,5-dihydro-1H-1,2,4-triazol-1-yl)phenyl]thio}phenyl)tetrahydro-2H-pyran-4-carbonitrile (Compound No. 56), 4-[3-({4-[4-(2-Hydroxyethyl)-5-oxo-4,5-dihydro-1H-1,2,4-triazol-1-yl]phenyl}thio)phenyl]tetrahydro-2H-pyran-4-carbonitrile (Compound No. 57), 4,5-Dimethyl-2-[4-({3-[4-(4-methyl-4H-1,2,4-triazol-3-yl)tetrahydro-2H-pyran-4-yl]phenyl}thio)phenyl]-2,4-dihydro-3H-1,2,4-triazol-3-one (Compound No. 58), 4-Ethyl-2-[4-({3-[4-(4-ethyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 59), 5-Methyl-4-propyl-2-[4-({3-[4-(4-propyl-4H-1,2,4-triazol-3-yl)tetrahydro-2H-pyran-4-yl]phenyl}thio)phenyl]-2,4-dihydro-3H-1,2,4-triazol-3-one (Compound No. 60), 4-Isopropyl-2-[4-({3-[4-(4-isopropyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 61), 4-Butyl-2-[4-({3-[4-(4-butyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 62), 4-Isobutyl-2-[4-({3-[4-(4-isobutyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 63), 4-Cyclopentyl-2-[4-({3-[4-(4-cyclopentyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 64), 4-Cyclohexyl-2-[4-({3-[4-(4-cyclohexyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 65), 4-Cycloheptyl-2-[4-({3-[4-(4-cycloheptyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 66), 4-Allyl-2-[4-({3-[4-(4-allyl-4H-1,2,4-triazol-3-yl)tetrahydro-2H-pyran-4-yl]phenyl}thio)phenyl]-5-methyl-2,4-dihydro-3H-1,2,4-triazol-3-one (Compound No. 67), 5-Methyl-2-[4-({3-[4-(4H-1,2,4-triazol-3-yl)tetrahydro-2H-pyran-4-yl]phenyl}thio)phenyl]-2,4-dihydro-3H-1,2,4-triazol-3-one (Compound No. 68), 4,5-Dimethyl-2-[4-({3-[4-(3-methyl-1,2,4-oxadiazol-5-yl)tetrahydro-2H-pyran-4-yl]phenyl}thio)phenyl]-2,4-dihydro-3H-1,2,4-triazol-3-one (Compound No. 69), 5-Methyl-2-[4-({3-[4-(5-methyl-1,3-oxazol-2-yl)tetrahydro-2H-pyran-4-yl]phenyl}thio)phenyl]-2,4-dihydro-3H-1,2,4-triazol-3-one (Compound No. 70), 4,5-Dimethyl-2-[4-({3-[4-(5-methyl-1,3-oxazol-2-yl)tetrahydro-2H-pyran-4-yl]phenyl}thio)phenyl]-2,4-dihydro-3H-1,2,4-triazol-3-one (Compound No. 71), 2-[4-({3-[4-(4,5-Dimethyl-4,5-dihydro-1,3-oxazol-2-yl)tetrahydro-2H-pyran-4-yl]phenyl}thio)phenyl]-5-methyl-2,4-dihydro-3H-1,2,4-triazol-3-one (Compound No. 72), and 2-[4-({3-[4-(4,5-Dimethyl-4,5-dihydro-1,3-oxazol-2-yl)tetrahydro-2H-pyran-4-yl]phenyl}thio)phenyl]-4,5-dimethyl-2,4-dihydro-3H-1,2,4-triazol-3-one (Compound No. 73), or a pharmaceutically acceptable salt, pharmaceutically acceptable, stereoisomer, tautomer, racemate, or N-oxide thereof.

3. A pharmaceutical composition comprising a therapeutically effective amount of a compound of Formula I or a pharmaceutically acceptable salt, pharmaceutically acceptable stereoisomer, tautomer, racemate, or N-oxide thereof, and one or more pharmaceutically acceptable carriers, excipients or diluents, wherein the compound of Formula I has the structure:

Formula I wherein
G is O or S,
Z is —$(CH_2)_{n2}$—X— or —X—$(CH_2)_{n2}$—,
X is —$NR_1$, —O— or —S—, $n_1$ is 0, 1 or 2, $n_2$ is 0, 1 or 2, $R_1$ is hydrogen, alkyl, alkenyl, alkynyl, cycloalkyl, (cycloalkyl)alkyl, aryl, aralkyl, heteroaryl, heterocyclyl, (heteroaryl)alkyl, or (heterocyclyl)alkyl, $R_2$ is —CN, —COR$_3$, or a 5-membered heteroaryl or heterocyclyl, and $R_3$ is hydrogen, alkyl, alkenyl, alkynyl, cycloalkyl, (cycloalkyl)alkyl, aryl, aralkyl, heteroaryl, heterocyclyl, (heteroaryl)alkyl, (heterocyclyl)alkyl, —OR$_1$, —SR$_1$ or —N(R$_1$)$_2$.

4. A pharmaceutical composition comprising a therapeutically effective amount of:
   a compound of Formula I or a pharmaceutically acceptable salt, pharmaceutically acceptable stereoisomer, tautomer, racemate, or N-oxide thereof and
   at least one active ingredient selected from one or more muscarinic receptor antagonists, PDE$_4$ inhibitors, PDE$_{3/4}$ inhibitors, PDE$_{4B}$ inhibitors, PDE$_7$ inhibitors, MMP9/12 inhibitors, caspase-1 inhibitors, beta 2 adrenoreceptor agonists, corticosteroids, p38 mitogen activated protein kinases, nuclear factor kappa B inhibitors, I kappa kinase inhibitors, VLA4 antagonists, thromboxane A2 antagonists, COX inhibitors, neutrophil elastase inhibitors, tachykinin receptor antagonists, secretory leukoprotease inhibitors, prostaglandin E analogues, adhesion molecule inhibitors, lipoxin agonists, tumour necrosis factor (TNF) inhibitors, inflammatory cytokine inhibitors, chemokine inhibitors, chemokine receptor inhibitors, adenosine receptor antagonists, platelet activating factor antagonists, histamine release inhibitors, histamine receptor antagonists, nitric oxide synthase inhibitors, neurokinin antagonists, syk tyrosine kinase inhibitors or a mixture thereof.

5. A method of treating bronchial asthma and chronic obstructive pulmonary disorder comprising administering to a patient in need thereof a therapeutically effective amount of a compound of Formula I,

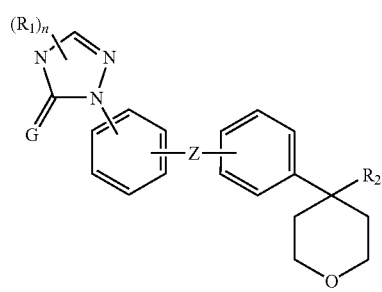

Formula I wherein

G is O or S,

Z is —(CH$_2$)$_n$—X— or —X—(CH$_2$)$_n$—,

X is —NR$_1$, —O— or —S—, n is 0, 1 or 2, $R_1$ is hydrogen, alkyl, alkenyl, alkynyl, cycloalkyl, (cycloalkyl)alkyl, aryl, aralkyl, heteroaryl, heterocyclyl, (heteroaryl)alkyl, or (heterocyclyl)alkyl, $R_2$ is —CN, —COR$_3$, or a 5-membered heteroaryl or heterocyclyl, and $R_3$ is hydrogen, alkyl, alkenyl, alkynyl, cycloalkyl, (cycloalkyl)alkyl, aryl, aralkyl, heteroaryl, heterocyclyl, (heteroaryl)alkyl, (heterocyclyl)alkyl, —OR$_1$, —SR$_1$ or —N(R$_1$)$_2$.

6. A method for preparing a compound of Formula XVI

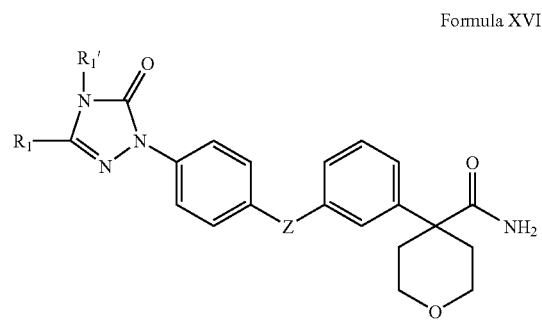

Formula XVI comprising the steps of:
(i) coupling a compound of Formula II with ammonium carbonate to form a compound of Formula III (wherein $X_1$ is halogen),

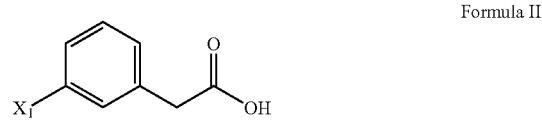

Formula II

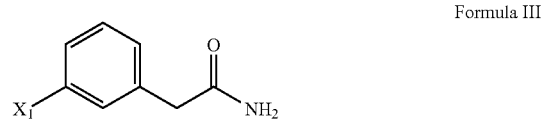

Formula III (ii) dehydrating a compound of Formula III to form a compound of Formula IV,

Formula IV (iii) reacting a compound of Formula IV with a compound of Formula V (wherein $X_1$ is halogen) to form a compound of Formula VI, (X$_1$CH$_2$CH$_2$)$_2$O Formula V

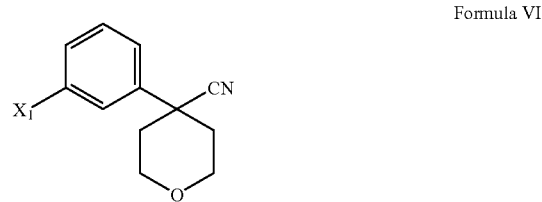

Formula VI (iv) reacting a compound of Formula VI with a compound of Formula VII to form a compound of Formula VIII, Formula VII
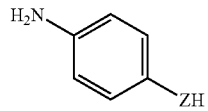

Formula VIII
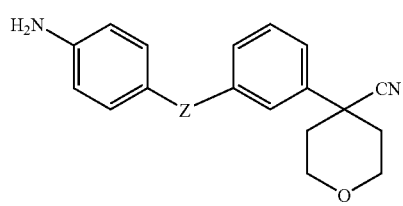

(v) reacting a compound of Formula VIII with a compound of Formula IX (wherein $X_1$ is halogen) to form a compound of Formula X (wherein Ar is aryl), Formula IX

Formula X
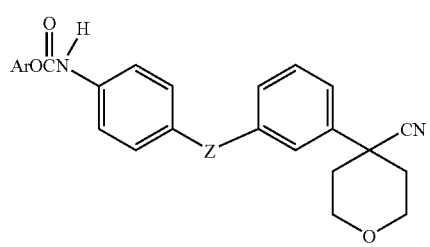

(vi) reacting a compound of Formula X with hydrazine to form a compound of Formula XI, Formula XI
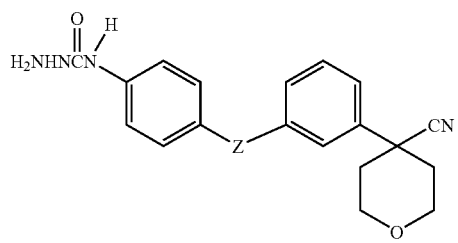

(vii) reacting a compound of Formula XI with a compound of Formula XII to form a compound of Formula XIII, Formula XII
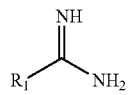

Formula XIII
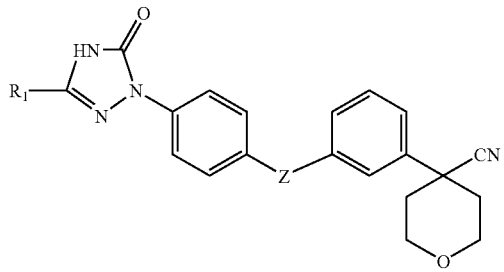

(viii) reacting a compound of Formula XIII with a compound of Formula XIV (wherein $X_1$ is halogen) to form a compound of Formula XV, Formula XIV
$R_1'X_1$ Formula XV
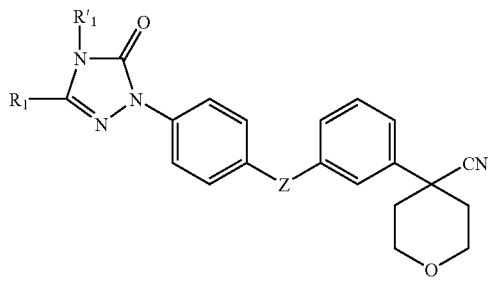

(ix) and hydrolyzing a compound of Formula XV to form a compound of Formula XVI, wherein
Z is —(CH$_2$)$_n$—X— or —X—(CH$_2$)$_n$—,
X is —NR$_1$, —O— or —S—,
n is 0, 1 or 2,
R$_1$ is hydrogen, alkyl, alkenyl, alkynyl, cycloalkyl, (cycloalkyl)alkyl, aryl, aralkyl, heteroaryl, heterocyclyl, (heteroaryl)alkyl or (heterocyclyl)alkyl, and
R$_1$' is alkyl, alkenyl, alkynyl, cycloalkyl, (cycloalkyl)alkyl, aryl, aralkyl, heteroaryl, heterocyclyl, (heteroaryl)alkyl or (heterocyclyl)alkyl).

7. A method for preparing a compound of Formula XVII

Formula XVII
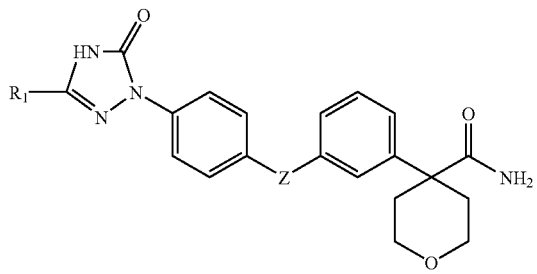

comprising the steps of:
(i) coupling a compound of Formula II with ammonium carbonate to form a compound of Formula III (wherein $X_1$ is halogen), Formula II

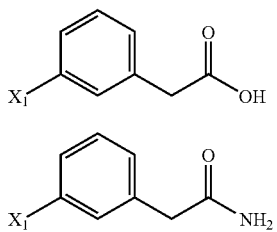

Formula III (ii) dehydrating a compound of Formula III to form a compound of Formula IV, Formula IV

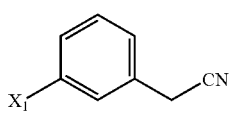

(iii) reacting a compound of Formula IV with a compound of Formula V (wherein $X_1$ is halogen) to form a compound of Formula VI, Formula V $(X_1CH_2CH_2)_2O$ Formula VI

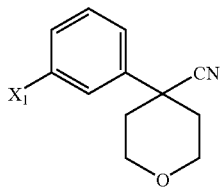

(iv) reacting a compound of Formula VI with a compound of Formula VII to form a compound of Formula VIII, Formula VII

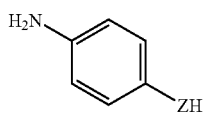

Formula VIII

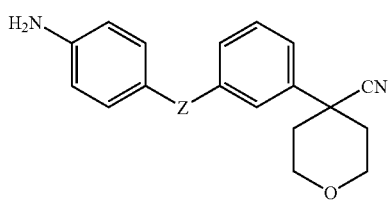

(v) reacting a compound of Formula VIII with a compound of Formula IX (wherein $X_1$ is halogen) to form a compound of Formula X (wherein Ar is aryl), Formula IX

Formula X

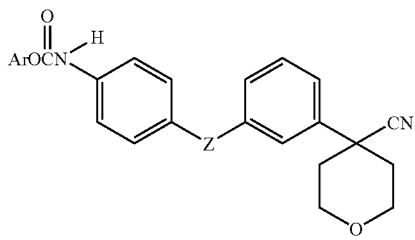

(vi) reacting a compound of Formula X with hydrazine to form a compound of Formula XI, Formula XI

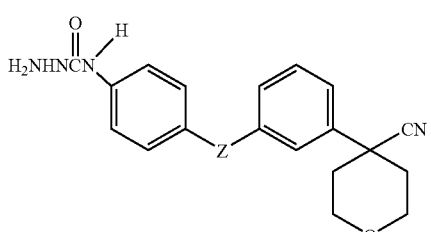

(vii) reacting a compound of Formula XI with a compound of Formula XII to form a compound of Formula XIII, Formula XII

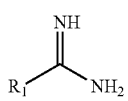

Formula XIII

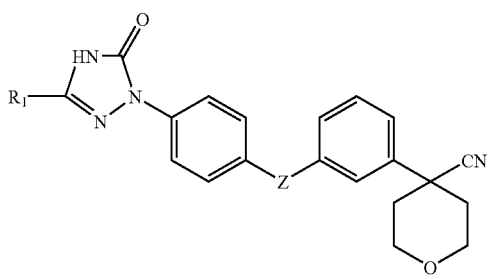

(viii) hydrolyzing a compound of Formula XIII to form a compound of Formula XVII, wherein Z is —$(CH_2)_n$—X— or —X—$(CH_2)_n$—, X is —$NR_1$, —O— or —S—, n is 0, 1 or 2, and $R_1$ is hydrogen, alkyl, alkenyl, alkynyl, cycloalkyl, (cycloalkyl)alkyl, aryl, aralkyl, heteroaryl, heterocyclyl, (heteroaryl)alkyl or (heterocyclyl)alkyl .

8. A method for preparing a compound of Formula XXI,

Formula XXI

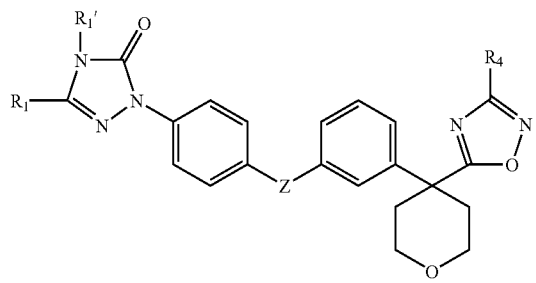

comprising the steps of
(i) reacting a compound of Formula XVII with a compound of Formula XVIII to form a compound of Formula XIX (wherein $R_5$ is alkyl), Formula XVII

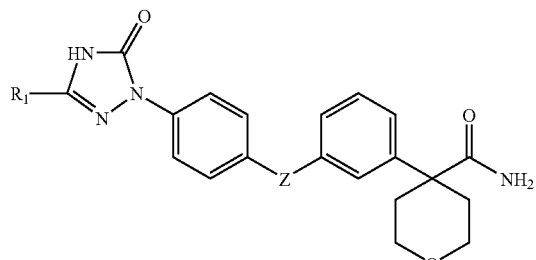

Formula XVIII

Formula XIX

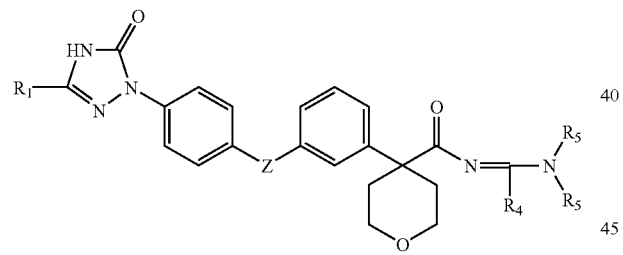

(ii) reacting a compound of Formula XIX with hydroxylamine to form a compound of Formula XX, Formula XX

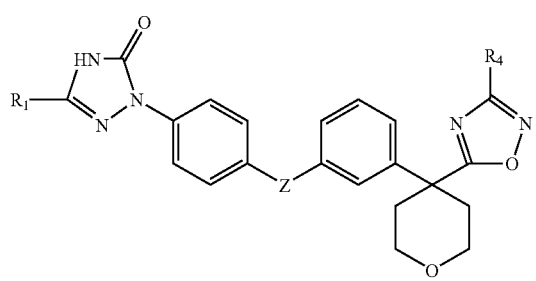

(iii) and reacting a compound of Formula XX with a compound of Formula XIV (wherein $X_1$ is halogen)

$R_1'X_1$

Formula XIV to form a compound of Formula XXI, wherein

Z is —$(CH_2)_n$—X— or —X—$(CH_2)_n$—,

X is —$NR_1$, —O— or —S—, n is 0, 1 or 2, $R_1$ is hydrogen, alkyl, alkenyl, alkynyl, cycloalkyl, (cycloalkyl)alkyl, aryl, aralkyl, heteroaryl, heterocyclyl, (heteroaryl)alkyl, or (heterocyclyl)alkyl, $R_1'$ is alkyl, alkenyl, alkynyl, cycloalkyl, (cycloalkyl)alkyl, aryl, aralkyl, heteroaryl, heterocyclyl, (heteroaryl)alkyl, or (heterocyclyl)alkyl), and $R_4$ is hydrogen or alkyl.

9. A method for preparing a compound of Formula XXIII,

Formula XXIII

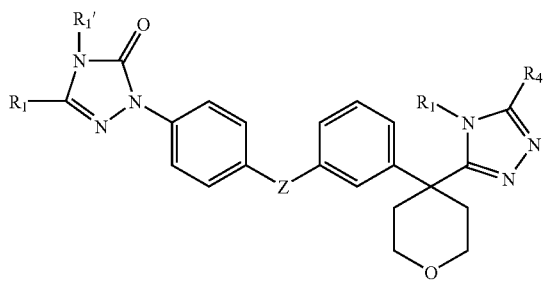

comprising the steps of:
(i) reacting a compound of Formula XVII with a compound of Formula XVIII to form a compound of Formula XIX (wherein $R_5$ is alkyl), Formula XVII

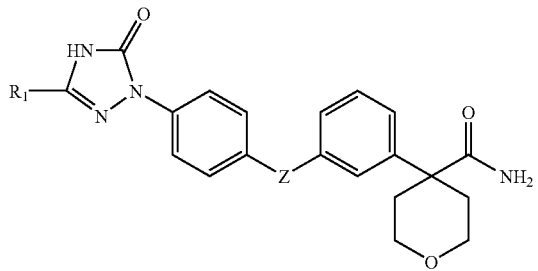

Formula XVIII

Formula XIX (ii) reacting a compound of Formula XIX with hydrazine to form a compound of Formula XXII, and Formula XXII

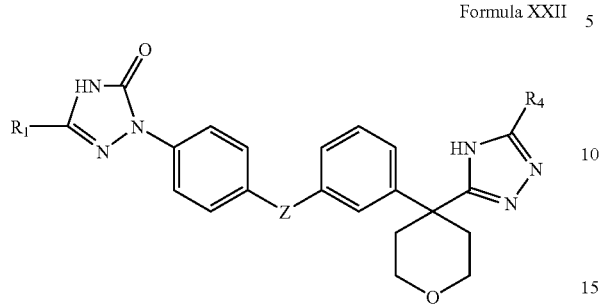

(iii) and reacting a compound of Formula XXII with a compound of Formula XIV (wherein $X_1$ is halogen)

$R_1'X_1$  Formula XIV to form a compound of Formula XXIII,
wherein
Z is —$(CH_2)_n$—X— or —X—$(CH_2)_n$—,
X is —$NR_1$, —O— or —S—,
n is 0, 1 or 2,
$R_1$ is hydrogen, alkyl, alkenyl, alkynyl, cycloalkyl, (cycloalkyl)alkyl, aryl, aralkyl, heteroaryl, heterocyclyl, (heteroaryl)alkyl, or (heterocyclyl)alkyl,
$R_1'$ is alkyl, alkenyl, alkynyl, cycloalkyl, (cycloalkyl)alkyl, aryl, aralkyl, heteroaryl, heterocyclyl, (heteroaryl)alkyl, or (heterocyclyl)alkyl, and
$R_4$ is hydrogen or alkyl.

10. A method for preparing a compound of Formula XXVIII,

Formula XXVIII

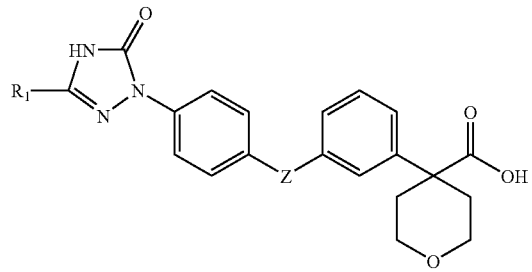

comprising the steps of:
(i) hydrolyzing a compound of Formula XVII to form a compound of Formula XXIV, Formula XVII

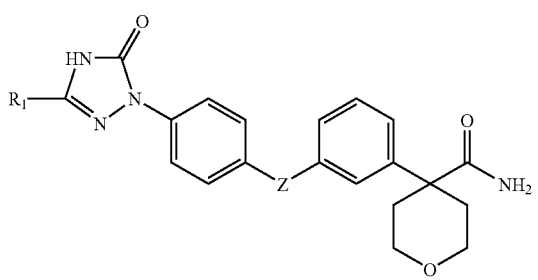

-continued

Formula XXIV

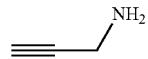

(ii) reacting a compound of Formula XXIV with a compound of Formula XXV to form a compound of Formula XXVI, Formula XXV

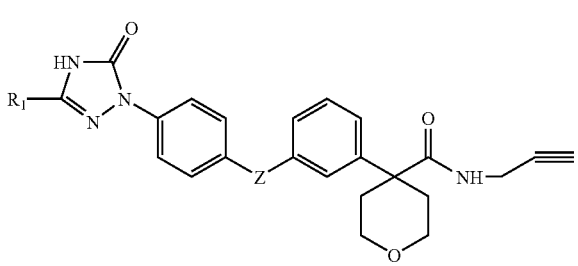

Formula XXVI (iii) cyclizing a compound of Formula XXVI to form a compound of Formula XXVII, and Formula XXVII (iv) reacting a compound of Formula XXVII with a compound of Formula XIV (wherein $X_1$ is halogen)

$R_1'X_1$  Formula XIV to form a compound of Formula XXVIII,
wherein
Z is —$(CH_2)_n$—X— or —X—$(CH_2)_n$—,
X is —$NR_1$, —O— or —S—,
n is 0, 1 or 2,
$R_1$ is hydrogen, alkyl, alkenyl, alkynyl, cycloalkyl, (cycloalkyl)alkyl, aryl, aralkyl, heteroaryl, heterocyclyl, (heteroaryl)alkyl, (heterocyclyl)alkyl, and
$R_1'$ is alkyl, alkenyl, alkynyl, cycloalkyl, (cycloalkyl)alkyl, aryl, aralkyl, heteroaryl, heterocyclyl, (heteroaryl)alkyl, (heterocyclyl)alkyl).

11. A method for preparing a compound of Formula XXXIV,

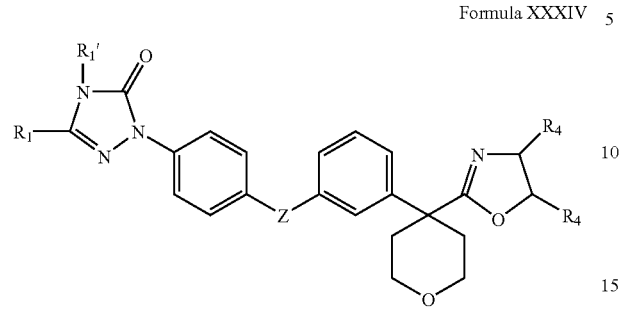
Formula XXXIV comprising the steps of:
(i) hydrolyzing a compound of Formula XVII to form a compound of Formula XXIV,

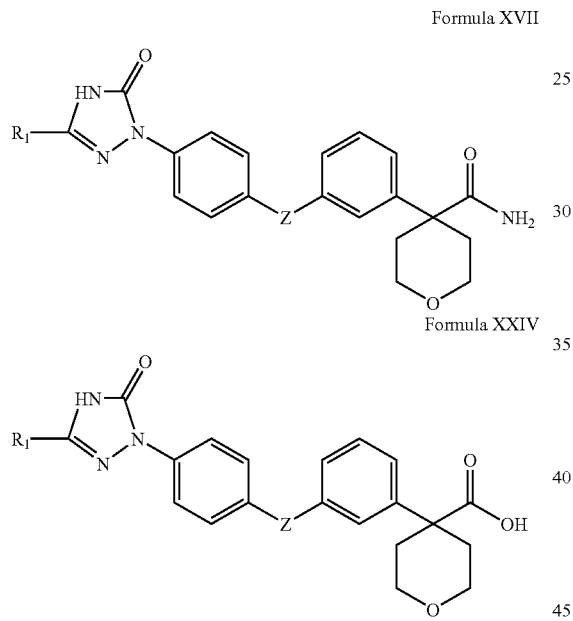
Formula XVII

Formula XXIV (ii) esterifying a compound of Formula XXIV with a compound of Formula XXIX to form a compound of Formula XXX (wherein $R_5$ is alkyl), $R_5OH$  Formula XXIX

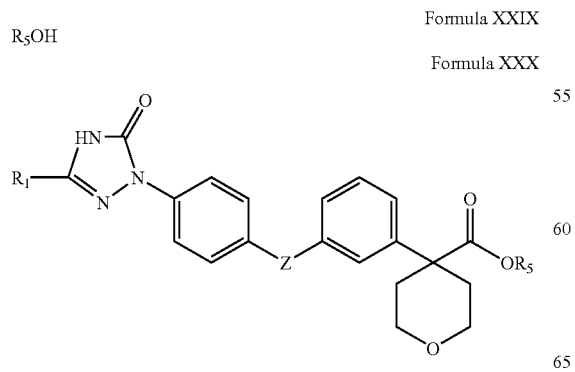
Formula XXX (iii) reacting a compound of Formula XXX with a compound of Formula XXXI to form a compound of Formula XXXII,

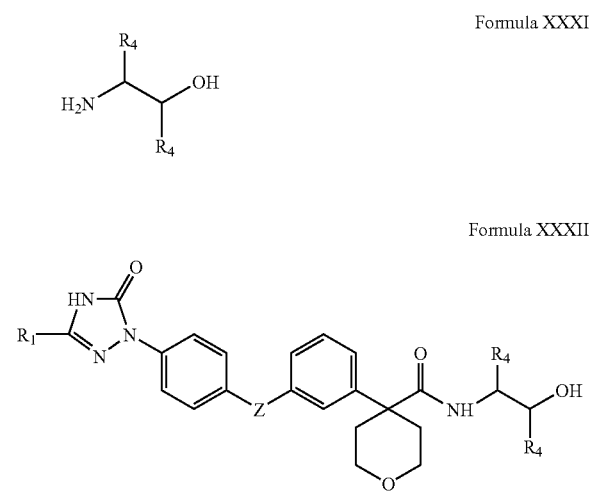
Formula XXXI

Formula XXXII (iv) cyclizing of a compound of Formula XXXII to form a compound of Formula XXXIII,

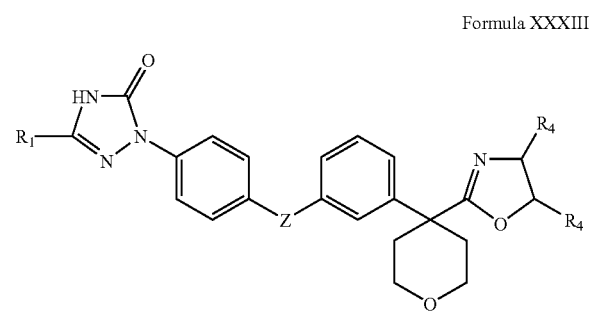
Formula XXXIII (v) reacting a compound of Formula XXXIII with a compound of Formula XIV (wherein $X_1$ is halogen)

$R_1'X_1$  Formula XIV to form a compound of Formula XXXIV,
wherein
Z is —$(CH_2)_n$—X— or —X—$(CH_2)_n$—,
X is —$NR_1$, —O— or —S—,
n is 0, 1 or 2,
$R_1$ is hydrogen, alkyl, alkenyl, alkynyl, cycloalkyl, (cycloalkyl)alkyl, aryl, aralkyl, heteroaryl, heterocyclyl, (heteroaryl)alkyl, or (heterocyclyl)alkyl,
$R_1'$ is alkyl, alkenyl, alkynyl, cycloalkyl, (cycloalkyl)alkyl, aryl, aralkyl, heteroaryl, heterocyclyl, (heteroaryl)alkyl, or (heterocyclyl)alkyl), and
$R_4$ is hydrogen or alkyl.

* * * * *